(12) United States Patent
Benton et al.

(10) Patent No.: US 11,389,481 B2
(45) Date of Patent: *Jul. 19, 2022

(54) ALLOGENEIC CELL THERAPY OF B CELL MALIGNANCIES USING GENETICALLY ENGINEERED T CELLS TARGETING CD19

(71) Applicant: CRISPR Therapeutics AG, Zug (CH)

(72) Inventors: Mark Benton, Cambridge, MA (US); Tony Ho, Cambridge, MA (US); Demetrios Kalaitzidis, Cambridge, MA (US); Ewelina Morawa, Cambridge, MA (US); Jonathan Alexander Terrett, Cambridge, MA (US)

(73) Assignee: CRISPR Therapeutics AG, Zug (CH)

( * ) Notice: Subject to any disclaimer, the term of this patent is extended or adjusted under 35 U.S.C. 154(b) by 0 days.

This patent is subject to a terminal disclaimer.

(21) Appl. No.: 17/237,679

(22) Filed: Apr. 22, 2021

(65) Prior Publication Data

US 2021/0268026 A1 Sep. 2, 2021

Related U.S. Application Data

(63) Continuation of application No. PCT/IB2020/054118, filed on Apr. 30, 2020.

(60) Provisional application No. 62/840,913, filed on Apr. 30, 2019.

(51) Int. Cl.
| | | |
|---|---|---|
| *A61K 35/17* | (2015.01) | |
| *A61P 35/00* | (2006.01) | |
| *C12N 15/85* | (2006.01) | |
| *C07K 16/28* | (2006.01) | |
| *A61K 48/00* | (2006.01) | |
| *C12N 5/0783* | (2010.01) | |
| *A61K 39/00* | (2006.01) | |
| *C07K 14/725* | (2006.01) | |

(52) U.S. Cl.
CPC ............ *A61K 35/17* (2013.01); *A61K 48/005* (2013.01); *A61P 35/00* (2018.01); *C07K 14/7051* (2013.01); *C07K 16/2866* (2013.01); *C12N 5/0636* (2013.01); *C12N 15/85* (2013.01); *A61K 2039/505* (2013.01); *C12N 2510/00* (2013.01)

(58) Field of Classification Search
CPC .............. A61K 35/17; A61K 2039/505; A61K 2039/5156; A61K 2039/5158; A61K 39/001112; A61K 48/00; A61P 35/00; C07K 14/7051; C07K 16/2803; C07K 16/2866; C07K 2317/622; C07K 2319/03; C07K 2319/33; C12N 15/85; C12N 2510/00; C12N 5/0636
USPC .......................................... 424/93.21, 93.71
See application file for complete search history.

(56) References Cited

U.S. PATENT DOCUMENTS

| | | |
|---|---|---|
| 7,083,785 B2 | 8/2006 | Browning et al. |
| 7,435,596 B2 | 10/2008 | Campana et al. |
| 7,446,179 B2 | 11/2008 | Jensen et al. |
| 7,446,190 B2 | 11/2008 | Sadelain et al. |
| 7,452,981 B2 | 11/2008 | Wijdenes et al. |
| 7,491,390 B2 | 2/2009 | Law et al. |
| 7,641,903 B2 | 1/2010 | Law et al. |
| 7,662,387 B2 | 2/2010 | Law et al. |
| 7,700,739 B2 | 4/2010 | Lacy et al. |
| 7,741,465 B1 | 6/2010 | Eshhar et al. |
| 7,771,720 B2 | 8/2010 | Staunton et al. |
| 7,888,121 B2 | 2/2011 | Umov et al. |
| 8,067,546 B2 | 11/2011 | McDonagh et al. |
| 8,124,738 B2 | 2/2012 | Terret et al. |
| 8,337,838 B2 | 12/2012 | Law et al. |
| 8,440,806 B2 | 5/2013 | Wijdenes et al. |
| 8,535,678 B2 | 9/2013 | Law et al. |
| 8,562,987 B2 | 10/2013 | McDonagh et al. |
| 8,609,104 B2 | 12/2013 | Law et al. |
| 8,629,257 B2 | 1/2014 | Lacy et al. |
| 8,647,624 B2 | 2/2014 | Law et al. |
| 8,663,642 B2 | 3/2014 | Law et al. |
| 8,673,304 B2 | 3/2014 | Wijdenes et al. |
| 8,834,882 B2 | 9/2014 | Silence et al. |
| 8,871,908 B2 | 10/2014 | Liu et al. |
| 8,956,828 B2 | 2/2015 | Bonini et al. |
| 9,023,999 B2 | 5/2015 | Mori et al. |
| 9,051,372 B2 | 6/2015 | Law et al. |
| 9,102,737 B2 | 8/2015 | Chen et al. |
| 9,120,854 B2 | 9/2015 | Ryan et al. |
| 9,169,325 B2 | 10/2015 | Keler et al. |
| 9,382,319 B2 | 7/2016 | Tso et al. |
| 9,399,074 B2 | 7/2016 | Liu et al. |
| 9,403,914 B2 | 8/2016 | Kubota |
| 9,428,585 B2 | 8/2016 | McDonagh et al. |
| 9,701,752 B2 | 7/2017 | McDonagh et al. |
| 9,758,581 B2 | 9/2017 | Wijdenes et al. |

(Continued)

FOREIGN PATENT DOCUMENTS

| | | |
|---|---|---|
| WO | WO 2004/073656 A2 | 9/2004 |
| WO | WO 2006/060878 A1 | 6/2006 |
| WO | WO 2006/113909 A2 | 10/2006 |
| WO | WO 2008/121420 A1 | 10/2008 |
| WO | WO 2011/059836 A2 | 5/2011 |

(Continued)

OTHER PUBLICATIONS

Eyquem et al. (2017, Nature. Mar. 2, 2017; 543(7643): 113-117) (Year: 2017).*

(Continued)

*Primary Examiner* — Janet L Epps-Smith
(74) *Attorney, Agent, or Firm* — McDermott Will & Emery LLP

(57) ABSTRACT

A population of genetically engineered immune cells (e.g., T cells), which express a chimeric antigen receptor (CAR) specific to CD19 and contain a disrupted TRAC gene, a disrupted B2M gene, or both, for use in treating a B cell malignancy.

20 Claims, 18 Drawing Sheets

Specification includes a Sequence Listing.

(56) References Cited

U.S. PATENT DOCUMENTS

| | | | |
|---|---|---|---|
| 9,765,148 B2 | 9/2017 | Silence et al. | |
| 9,765,149 B2 | 9/2017 | Silence et al. | |
| 9,889,160 B2 | 2/2018 | Jantz et al. | |
| 9,937,207 B2 | 4/2018 | Gregory et al. | |
| 10,166,255 B2 | 1/2019 | Moriarity et al. | |
| 10,253,086 B2 | 4/2019 | Bitter et al. | |
| 10,442,849 B2 | 10/2019 | Baeuerle et al. | |
| 10,584,352 B2 | 3/2020 | Duchateau et al. | |
| 10,736,919 B2 * | 8/2020 | Terrett | A61K 35/17 |
| 10,857,184 B2 * | 12/2020 | Terrett | C07K 14/70578 |
| 11,013,767 B2 * | 5/2021 | Terrett | C07K 14/70517 |
| 2006/0051346 A1 | 3/2006 | Wijdenes | |
| 2008/0138343 A1 | 6/2008 | Law et al. | |
| 2009/0081239 A1 | 3/2009 | Staunton et al. | |
| 2009/0148942 A1 | 6/2009 | McDonagh et al. | |
| 2009/0208496 A1 | 8/2009 | Wijdenes et al. | |
| 2010/0129362 A1 | 5/2010 | Law et al. | |
| 2010/0215651 A1 * | 8/2010 | Blein | A61P 7/00 424/133.1 |
| 2012/0034159 A1 | 2/2012 | Kindsvogel | |
| 2012/0045436 A1 | 2/2012 | McDonagh et al. | |
| 2012/0213771 A1 | 8/2012 | Keler et al. | |
| 2012/0294863 A1 | 11/2012 | Law et al. | |
| 2013/0039911 A1 | 2/2013 | Bedi et al. | |
| 2013/0122020 A1 | 5/2013 | Liu et al. | |
| 2013/0138586 A1 | 5/2013 | Jung et al. | |
| 2013/0287748 A1 | 10/2013 | June et al. | |
| 2014/0105915 A1 | 4/2014 | Algate et al. | |
| 2014/0112942 A1 | 4/2014 | Van Eenennaam et al. | |
| 2014/0178936 A1 | 6/2014 | McDonagh et al. | |
| 2014/0220008 A1 | 8/2014 | Wijdenes et al. | |
| 2014/0349402 A1 | 11/2014 | Cooper et al. | |
| 2014/0357844 A1 | 12/2014 | Liu et al. | |
| 2015/0033473 A1 | 2/2015 | Wu | |
| 2015/0176013 A1 | 6/2015 | Musunuru et al. | |
| 2015/0266963 A1 | 9/2015 | Silence et al. | |
| 2015/0284467 A1 | 10/2015 | Lipp et al. | |
| 2015/0337047 A1 | 11/2015 | Keler et al. | |
| 2015/0368351 A1 | 12/2015 | Vu et al. | |
| 2016/0046724 A1 | 2/2016 | Brogdon et al. | |
| 2016/0289675 A1 | 10/2016 | Ryan et al. | |
| 2016/0348073 A1 * | 12/2016 | Meissner | C12N 15/1138 |
| 2017/0022282 A1 | 1/2017 | McDonagh et al. | |
| 2017/0157176 A1 | 6/2017 | Wang et al. | |
| 2017/0173080 A1 | 6/2017 | Lee et al. | |
| 2017/0183418 A1 | 6/2017 | Galetto | |
| 2017/0226216 A1 | 8/2017 | Morgan et al. | |
| 2017/0233484 A1 | 8/2017 | Sussman et al. | |
| 2017/0246298 A1 * | 8/2017 | Francois | A61K 39/39558 |
| 2017/0267771 A1 | 9/2017 | Van Eenennaam et al. | |
| 2017/0281766 A1 | 10/2017 | Wiltzius | |
| 2017/0313759 A1 | 11/2017 | Batuwangala | |
| 2017/0320957 A1 | 11/2017 | Chen et al. | |
| 2017/0335281 A1 | 11/2017 | Loew et al. | |
| 2017/0342157 A1 | 11/2017 | McDonagh et al. | |
| 2017/0355776 A1 | 12/2017 | Xiao et al. | |
| 2017/0362297 A1 | 12/2017 | Marasco | |
| 2017/0369581 A9 | 12/2017 | Silence et al. | |
| 2018/0002435 A1 | 1/2018 | Sasu et al. | |
| 2018/0186878 A1 | 7/2018 | Rosenthal | |
| 2018/0318435 A1 | 11/2018 | Pastan et al. | |
| 2018/0325955 A1 * | 11/2018 | Terrett | C07K 14/70578 |
| 2020/0085869 A1 | 3/2020 | Schuster et al. | |

FOREIGN PATENT DOCUMENTS

| | | |
|---|---|---|
| WO | WO 2011/130434 A2 | 10/2011 |
| WO | WO 2012/004367 A1 | 1/2012 |
| WO | WO 2012/058460 A2 | 5/2012 |
| WO | WO 2012/079000 A1 | 6/2012 |
| WO | WO 2013/074916 A1 | 5/2013 |
| WO | WO 2013/138586 A1 | 9/2013 |
| WO | WO 2013/154760 A1 | 10/2013 |
| WO | WO 2013/176915 A1 | 11/2013 |
| WO | WO 2014/068079 A1 | 5/2014 |
| WO | WO 2014/122143 A1 | 8/2014 |
| WO | WO 2014/140374 A2 | 9/2014 |
| WO | WO 2014/158821 A1 | 10/2014 |
| WO | WO 2014/165119 A1 | 10/2014 |
| WO | WO 2014/165825 A2 | 10/2014 |
| WO | WO 2014/191128 A1 | 12/2014 |
| WO | WO 2015/120096 A2 | 8/2015 |
| WO | WO 2015/121454 A1 | 8/2015 |
| WO | WO 2015/134877 A1 | 9/2015 |
| WO | WO 2015/136001 A1 | 9/2015 |
| WO | WO 2015/158671 A1 | 10/2015 |
| WO | WO 2015/161276 A2 | 10/2015 |
| WO | WO 2015/164594 A1 | 10/2015 |
| WO | WO 2015/188056 A1 | 12/2015 |
| WO | WO-2015187528 A1 * | 12/2015 ......... C07K 16/2803 |
| WO | WO 2016/014789 A2 | 1/2016 |
| WO | WO 2016/025454 A2 | 2/2016 |
| WO | WO 2016/063264 A1 | 4/2016 |
| WO | WO 2016/069282 A1 | 5/2016 |
| WO | WO 2016/069283 A1 | 5/2016 |
| WO | WO 2016/073955 A2 | 5/2016 |
| WO | WO 2016/090320 A1 | 6/2016 |
| WO | WO 2016/094304 A2 | 6/2016 |
| WO | WO 2016/100985 A2 | 6/2016 |
| WO | WO 2016/120216 A1 | 8/2016 |
| WO | WO 2016/151315 A1 | 9/2016 |
| WO | WO 2016/160721 A1 | 10/2016 |
| WO | WO 2016/164356 A1 | 10/2016 |
| WO | WO 2016/174652 A1 | 11/2016 |
| WO | WO 2016/183041 A2 | 11/2016 |
| WO | WO 2017/058850 A1 | 4/2017 |
| WO | WO 2017/062451 A1 | 4/2017 |
| WO | WO 2017/070429 A1 | 4/2017 |
| WO | WO 2017/075537 A1 | 5/2017 |
| WO | WO-2017/083511 A1 | 5/2017 |
| WO | WO 2017/093969 A1 | 6/2017 |
| WO | WO 2017/100176 A1 | 6/2017 |
| WO | WO 2017/106528 A1 | 6/2017 |
| WO | WO 2017/112859 A2 | 6/2017 |
| WO | WO 2017/130233 A1 | 8/2017 |
| WO | WO 2017/143069 A1 | 8/2017 |
| WO | WO 2017/149515 A1 | 9/2017 |
| WO | WO 2017/156484 A1 | 9/2017 |
| WO | WO 2017/177137 A1 | 10/2017 |
| WO | WO 2017/180993 A1 | 10/2017 |
| WO | WO 2017/186928 A1 | 11/2017 |
| WO | WO 2017/189959 A1 | 11/2017 |
| WO | WO 2017/210617 A2 | 12/2017 |
| WO | WO 2017/211900 A1 | 12/2017 |
| WO | WO 2017/222593 A1 | 12/2017 |
| WO | WO 2018/068257 A1 | 4/2018 |
| WO | WO 2018/073391 A2 | 4/2018 |
| WO | WO 2018/073393 A2 | 4/2018 |
| WO | WO 2018/132479 A1 | 7/2018 |
| WO | WO 2018/193394 A1 | 10/2018 |
| WO | WO 2019/076486 A1 | 4/2019 |
| WO | WO-2019079564 A1 * | 4/2019 ...... A61K 39/001112 |
| WO | WO 2019/089650 A1 | 5/2019 |
| WO | WO 2020/183147 A1 | 9/2020 |

OTHER PUBLICATIONS

Mollanoori et al. (Human Immunology 79 (2018) 876-882) (Year: 2018).*
U.S. Appl. No. 17/607,641, filed Oct. 29, 2021, Benton et al.
U.S. Appl. No. 17/488,215, filed Sep. 28, 2021, Terrett et al.
U.S. Appl. No. 17/359,041, filed Jun. 25, 2021, Terrett et al.
U.S. Appl. No. 17/505,106, filed Oct. 19, 2021, Benton et al.
U.S. Appl. No. 17/559,500, filed Dec. 22, 2021, Terrett et al.
Matas-Cespedes et al., Daratumumab, a Novel Human Anti-CD38 Monoclonal Antibody for the Treatment of Chronic Lymphocytic Leukemia and B-Cell Non-Hodgkin Lymphoma. Blood. Nov. 16, 2012;120(21):3935.
Salles et al., Phase 2 Study of Daratumumab in Relapsed/Refractory Mantle-Cell Lymphoma, Diffuse Large B-Cell Lymphoma, and Follicular Lymphoma. Clin Lymphoma Myeloma Leuk. May 2019;19(5):275-284. Epub Jan. 2, 2019.

(56) References Cited

OTHER PUBLICATIONS

Turtle et al., Anti-CD19 Chimeric Antigen Receptor-Modified T Cell Therapy for B Cell Non-Hodgkin Lymphoma and Chronic Lymphocytic Leukemia: Fludarabine and Cyclophosphamide Lymphodepletion Improves In Vivo Expansion and Persistence of CAR-T Cells and Clinical Outcomes. Blood. Dec. 3, 2015;126(23):184.
Fraiietta et al., Determinants of response and resistance to CD19 chimeric antigen receptor (CAR) T cell therapy of chronic lymphocytic leukemia. Nat Med. 2018;24(5):563-71.
Jaspers et al., Development of CAR T cells designed to improve antitumor efficacy and safety. Pharmacol Ther. Oct. 2017;178:83-91. Epub Mar. 22, 2017.
Liu et al., CRISPR-Cas9-mediated multiplex gene editing in CAR-T cells. Cell Res. Jan. 2017;27(1):154-157. Epub Dec. 2, 2016.
Macleod et al., Integration of a CD19 CAR into the TCR alpha chain locus streamlines production of alleogenic gene-edited CAR T cells. Mol Ther. 2017;25(4):949-61.
Maude et al., Chimeric antigen receptor T cells for sustained remissions in leukemia. N Engl J Med. 2014;371:1507-17.
Osborn et al., Evaluation of TCR gene editing achieved by TALENs, CRISPR/Cas9, and megaTAL nucleases. Mol Ther. 2016;24(3):570-81.
Poirot et al., Multiplex genome-edited T-cell manufacturing platform for "off-the-shelf" adoptive T-cell immunotherapies. Cancer Res. 2015;75(18):3853-64.
Ren et al., A versatile system for rapid multiplex genome-edited CAR T cell generation. Oncotarget. 2017;8(10):17002-11.
Ren et al., Advancing chimeric antigen receptor T cell therapy with CRISPR/Cas9. Protein Cell. Sep. 2017;8(9):634-643. Epub Apr. 22, 2017.
Ren et al., Multiplex Genome Editing to Generate Universal CAR T Cells Resistant to PD1 Inhibition. Clin Cancer Res. May 1, 2017;23(9):2255-2266. Epub Nov. 4, 2016.
Torikai et al., A foundation for universal T-cell based immunotherapy: T cells engineered to express a CD19-specific chimeric-antigen-receptor and eliminate expression of endogenous TCR. Blood. Jun. 14, 2012;119(24):5697-705. Epub Apr. 24, 2012. Erratum in: Blood. Nov. 26, 2015;126(22):2527. Rabinovitch, Brian [corrected to Rabinovich, Brian].
Zah et al., T Cells Expressing CD19/CD20 Bispecific Chimeric Antigen Receptors Prevent Antigen Escape by Malignant B Cells. Cancer Immunol Res. Jun. 2016;4(6):498-508. doi: 10.1158/2326-6066.CIR-15-0231. Epub Apr. 8, 2016.

\* cited by examiner

ALLOGENEIC CELL THERAPY OF B CELL MALIGNANCIES USING GENETICALLY ENGINEERED T CELLS TARGETING CD19

CROSS REFERENCE TO RELATED APPLICATIONS

This application is a continuation of and claims the benefit of and priority to International Application No. PCT/IB2020/054118 filed on Apr. 30, 2020, which claims the benefit of and priority to U.S. Provisional Application No. 62/840,913, filed Apr. 30, 2019, the entire contents of each of which are incorporated by reference herein.

SEQUENCE LISTING

The application contains a Sequence Listing that has been filed electronically in the form of a text file, created Apr. 22, 2021, and named "095136-0323_SequenceListing.txt" (55,123 bytes), the contents of which are incorporated by reference herein in their entirety.

BACKGROUND OF THE INVENTION

Chimeric antigen receptor (CAR) T cell therapies are adoptive T cell therapeutics used to treat human malignancies. Although CAR T cell therapy has led to tremendous clinical success, including durable remission in relapsed/refractory non-Hodgkin lymphoma (NHL) and pediatric acute lymphoblastic leukemia (ALL), the approved products are autologous and require patient-specific cell collection and manufacturing. Because of this, some patients have experienced disease progression or death while awaiting treatment. Accordingly, there remains a need for improved CAR T cell therapeutics.

SUMMARY OF THE INVENTION

The present disclosure is based, at least in part, on the development of allogeneic cell therapy for B cell malignancies such as transformed FL or DLBCL using genetically engineered T cells (e.g., CTX110 cells, a.k.a., TC1 cells) expressing an anti-CD19 chimeric antigen receptor (CAR) and having disrupted TRAC gene and B2M gene. The allogeneic CAR– T cell therapy disclosed herein showed treatment efficacies in human patients having B cell malignancies disclosed herein, including complete responses in certain patients and long durability of responses. Further, the allogeneic CAR-T cell therapy disclosed herein exhibited desired pharmacokinetic features in the human patients, including prolonged CAR-T cell expansion and persistence after infusion.

Accordingly, some aspects of the present disclosure provides a method for treating a B-cell malignancy in a human patient, the method comprising: (i) subjecting a human patient having a B-cell malignancy to a lymphodepletion treatment; and (ii) administering to the human patient a population of genetically engineered T cells after step (i). In some embodiments, step (i) can be performed about 2-7 days prior to step (ii). In some embodiments, the population of genetically engineered T cells is allogeneic.

The population of the genetically engineered T cells may comprise T cells that comprise: (a) a disrupted T cell receptor alpha constant (TRAC) gene, (b) a nucleic acid coding for a chimeric antigen receptor (CAR) that binds CD19, wherein the CAR comprises an anti-CD19 single chain variable fragment (scFv) that comprises a heavy chain variable region set forth in SEQ ID NO: 51, and a light chain variable region set forth in SEQ ID NO: 52, and wherein the nucleic acid is inserted in the disrupted TRAC gene, and (c) a disrupted beta 2-microglobulin (β2M) gene. In some embodiments, the disrupted TRAC gene comprises a deletion of a fragment comprising the nucleotide sequence of SEQ ID NO: 26.

In some embodiments, the population of genetically engineered T cells is administered to the human patient at a dose of about $1 \times 10^7$ to about $1 \times 10^9$ CAR$^+$ T cells. In some examples, the population of genetically engineered T cells is administered to the human patient at a dose of about $1 \times 10^7$ CAR$^+$ T cells. In some examples, the population of genetically engineered T cells is administered to the human patient at a dose of about $3 \times 10^7$ CAR$^+$ T cells. In some examples, the population of genetically engineered T cells is administered to the human patient at a dose of about $1 \times 10^8$ CAR$^+$ T cells. In some examples, the population of genetically engineered T cells is administered to the human patient at a dose of about $3 \times 10^8$ CAR$^+$ T cells. In some examples, the population of genetically engineered T cells is administered to the human patient at a dose of about $1 \times 10^9$ CAR$^+$ T cells. In any event, the population of genetically engineered T cells administered to the human patient per dose contains no more than $7 \times 10^4$ TCR$^+$ T cells/kg.

In some embodiments, the lymphodepletion treatment in step (i) comprises co-administration to the human patient fludarabine at about 30 mg/m$^2$ and cyclophosphamide at about 500-750 mg/m$^2$ per day for three days. For example, the lymphodepletion treatment in step (i) comprises co-administration to the human patient fludarabine at about 30 mg/m$^2$ and cyclophosphamide at about 500 mg/m$^2$ per day for three days. In other examples, the lymphodepletion treatment in step (i) comprises co-administration to the human patient fludarabine at about 30 mg/m$^2$ and cyclophosphamide at about 750 mg/m$^2$ per day for three days.

In some embodiments, prior to step (i), the human patient does not show one or more of the following features: (a) significant worsening of clinical status, (b) requirement for supplemental oxygen to maintain a saturation level of greater than 91%, (c) uncontrolled cardiac arrhythmia, (d) hypotension requiring vasopressor support, (e) active infection, and (f) grade ≥2 acute neurological toxicity.

In some embodiments, after step (i) and prior to step (ii), the human patient does not show one or more of the following features: (a) active uncontrolled infection; (b) worsening of clinical status compared to the clinical status prior to step (i); and (c) grade ≥2 acute neurological toxicity.

Any of the methods disclosed herein may further comprise (iii) monitoring the human patient for development of acute toxicity after step (ii); and (iv) managing the acute toxicity if occurs. In some embodiments, step (iii) can be performed for at least 28 days after administration of the population of genetically engineered T cells. Exemplary acute toxicity may comprise tumor lysis syndrome (TLS), cytokine release syndrome (CRS), immune effector cell-associated neurotoxicity syndrome (ICANS), B cell aplasia, hemophagocytic lymphohistiocytosis (HLH), cytopenia, graft-versus-host disease (GvHD), hypertension, renal insufficiency, or a combination thereof.

In some embodiments, the B cell malignancy is non-Hodgkin lymphoma. Examples include, but are not limited to, diffuse large B cell lymphoma (DLBCL), high grade B cell lymphoma with MYC and BCL2 and/or BCL6 rearrangement, transformed follicular lymphoma (FL), or grade 3b FL. In some instances, DLBCL is DLBCL not otherwise specified (NOS). In some examples, the B cell malignancy is refractory and/or relapsed.

In some embodiments, the human patient may have at least one measurable lesion that is fluorodeoxyglucose positron emission tomography (PET)-positive. In some embodiments, the human patient has undergone one or more lines of prior anti-cancer therapies. In some examples, the human patient has undergone two or more lines of prior anti-cancer therapies. Exemplary prior anti-cancer therapies may comprise an anti-CD20 antibody, an anthracycline-containing regimen, or a combination thereof.

In some examples, the human patient has refractory or relapsed transformed FL and has undergone at least one line of chemotherapy for disease after transformation to DLBCL. In other examples, the B cell malignancy is refractory, and the human patient has progressive disease on last therapy, or has stable disease following at least two cycles of therapy with duration of stable disease of up to 6 months. In yet other examples, the human patient has failed prior autologous hematopoietic stem cell transplantation (HSCT) or ineligible for prior autologous HSCT. Alternatively or in addition, the human patient is subject to an additional anti-cancer therapy after treatment with the population of genetically engineered T cells.

In any of the methods disclosed herein, the human patient has one or more of the following features:

(a) has an Eastern Cooperative Oncology Group (ECOG) performance status 0 or 1;

(b) adequate renal, liver, cardiac, and/or pulmonary function;

(c) free of prior gene therapy or modified cell therapy;

(d) free of prior treatment comprising an anti-CD19 antibody;

(e) free of prior allogeneic HSCT;

(f) free of detectable malignant cells from cerebrospinal fluid;

(g) free of brain metastases;

(h) free of prior central nervous system disorders;

(i) free of unstable angina, arrhythmia, and/or myocardial infarction;

(j) free of uncontrolled infection;

(k) free of immunodeficiency disorders or autoimmune disorders that require immunosuppressive therapy; and (l) free of infection by human immunodeficiency virus, hepatitis B virus, or hepatitis C virus.

In any of the methods disclosed herein, the anti-CD19 CAR expressed by the genetically engineered T cells may comprise an extracellular antigen binding domain, which is an anti-CD19 scFv comprising the amino acid sequence of SEQ ID NO: 47. In some embodiments, the anti-CD19 CAR may comprise the amino acid sequence of SEQ ID NO: 40.

In some embodiments, the nucleic acid encoding the anti-CD19 CAR is inserted at the site of deletion in the disrupted TRAC gene. In some examples, the disrupted TRAC gene comprises the nucleotide sequence of SEQ ID NO: 54. Alternatively or in addition, the disrupted β2M gene in the population of genetically engineered T cells comprises at least one of the nucleotide sequence set forth in SEQ ID NOs: 9-14.

In some embodiments, at least 90% of the T cells in the population of genetically engineered T cells do not express a detectable level of TCR surface protein. For example, at least 70% of the T cells in the population of genetically engineered T cells do not express a detectable level of TCR surface protein; at least 50% of the T cells in the population of genetically engineered T cells do not express a detectable level of B2M surface protein; and/or at least 30% of the T cells in the population of genetically engineered T cells express a detectable level of the CAR. In some examples, at least 99.5% of the T cells in the population of genetically engineered T cells do not express a detectable level of TCR surface protein. In some examples, at least 70% of the T cells in the population of genetically engineered T cells do not express a detectable level of B2M surface protein. In specific examples, at least 85% of the T cells in the population of the genetically engineered T cells do not express a detectable level of B2M surface protein. In some examples, at least 50% of the T cells in the population of genetically engineered T cells express a detectable level of the CAR. In specific examples, at least 70% of the T cells in the population of genetically engineered T cells express a detectable level of the CAR.

In a specific example, the population of genetically engineered T cells for use in any of the methods disclosed herein are CTX110 cells.

In any of the methods disclosed herein, the population of genetically engineered T cells are administered to the human patient via intravenous infusion. In some examples, the population of genetically engineered T cells may be suspended in a cryopreservation solution.

Also within the scope of the present disclosure are pharmaceutical compositions for use in treating a B-cell malignancy, the pharmaceutical composition comprising any of the population of genetically engineered T cells disclosed herein (e.g., the CTX110 cells), as well as use of the genetically engineered T cells for manufacturing a medicament for use in treating a B-cell malignancy as disclosed herein.

The details of one or more embodiments of the invention are set forth in the description below. Other features or advantages of the present invention will be apparent from the following drawings and detailed description of several embodiments, and also from the appended claims.

DETAILED DESCRIPTION OF THE INVENTION

Figure 1:
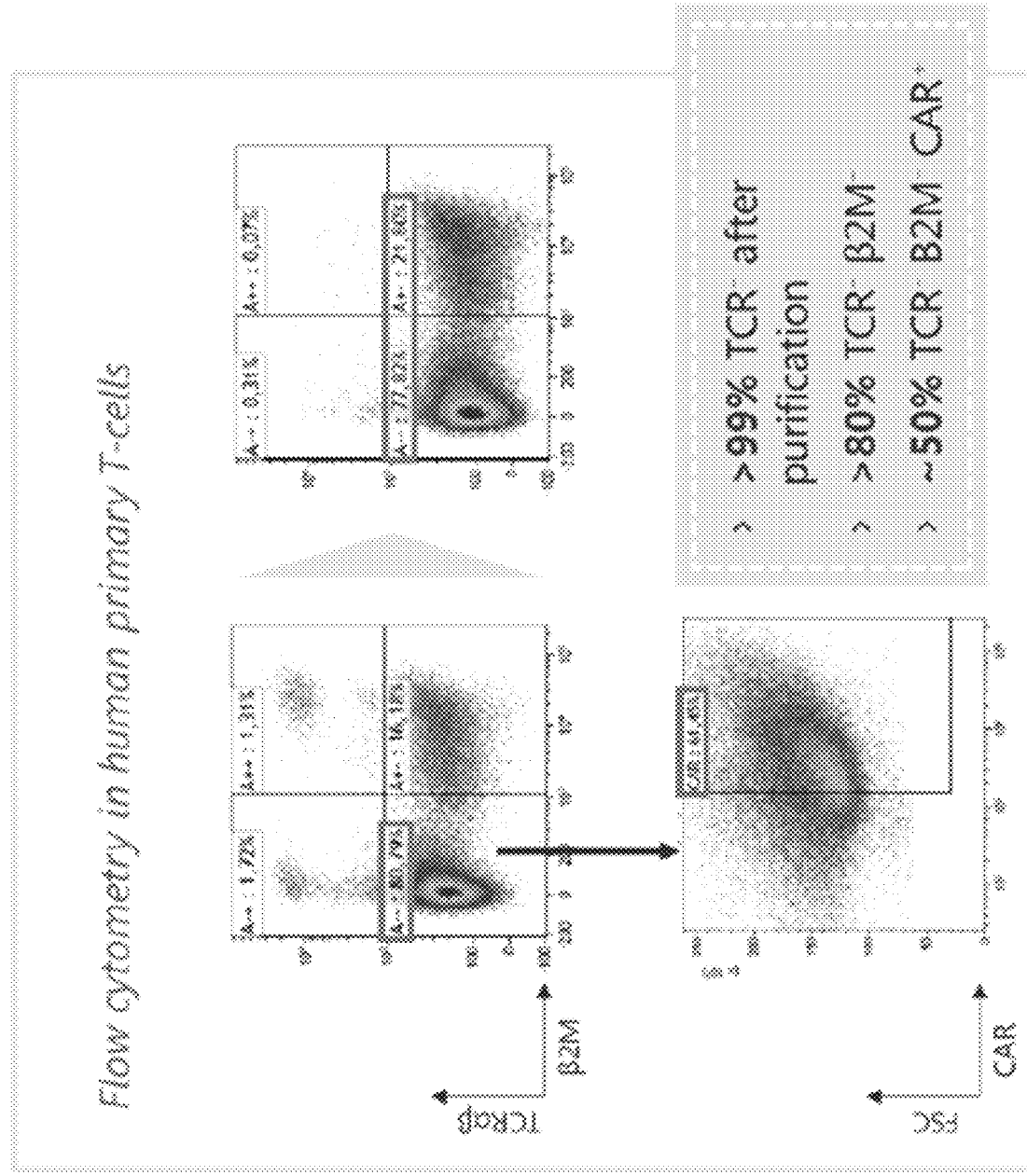
FIG. 1 is a series of flow cytometry plots of human primary T-cells, TRAC−/B2M-CD19CAR+T cells (TC1), 8 days post-editing. The graphs show reduced surface expression of TRAC and B2M. TCR/MHC I double knockout cells express high levels of the CAR transgene (bottom panel). Negative selection of TC1 cells with purification beads leads to a reduction in TCR positive cells (right panel).

Cluster of Differentiation 19 (CD19) is an antigenic determinant detectable on leukemia precursor cells. The human and murine amino acid and nucleic acid sequences can be found in a public database, such as GenBank, UniProt and Swiss-Prot. For example, the amino acid sequence of human CD19 can be found as UniProt/Swiss-Prot Accession No. P15391 and the nucleotide sequence encoding of the human CD19 can be found at Accession No. NM_001178098. CD19 is expressed on most B lineage cancers, including, e.g., acute lymphoblastic leukemia, chronic lymphocyte leukemia and non-Hodgkin's lymphoma. It is also an early marker of B cell progenitors. See, e.g., Nicholson et al. Mol. Immun. 34 (16-17): 1157-1165 (1997).

The present disclosure provides an allogeneic CAR-T cell therapy for B cell malignancies. The CAR-T cell therapy involves a population of genetically engineered T cells expressing an anti-CD19 CAR and having disrupted TRAC gene and B2M gene, the nucleic acid coding for the anti-CD19 CAR being inserted into the TRAC gene locus, thereby disrupting expression of the TRAC gene. The allogenic anti-CD19 CAR-T cells are prepared using parent T cells obtained from healthy donors. As such, the CAR-T therapy is available to a patient having the target B cell malignancy immediately after diagnosis, as opposed to at least three week gap between diagnosis and treatment in autologous CAR-T therapy required for manufacturing the CAR-T cells from the patient's own T cells. The allogeneic CAR T therapy can be stored and inventoried at the site of care to facilitate treatment immediately following diagnosis. The immediate availability of the allogeneic anti-CD19 CAR T therapy eliminates the need for bridging chemotherapy, which may be required when autologous CAR-T cells are manufactured from the patient's own cells. The allogeneic anti-CD19 CAR-T cell therapy disclosed herein showed treatment efficacies in human patients having B cell malignancies disclosed herein, including complete responses in certain patients and long durability of responses. Further, the allogeneic CAR-T cell therapy disclosed herein exhibited desired pharmacokinetic features in the human patients, including prolonged CAR-T cell expansion and persistence after infusion.

Accordingly, provided herein are methods for treating a B-cell malignancy in a human patient using a population of genetically engineered immune cells such as T cells, which collectively comprises a disrupted TRAC gene, a disrupted B2M, and a nucleic acid encoding an anti-CD19 CAR (e.g., SEQ ID NO: 40, encoded by SEQ ID NO:39). The nucleic acid encoding the anti-CD19 CAR and optionally comprising a promoter sequence and one or more regulatory elements may be inserted in the disrupted TRAC gene locus, e.g., replacing the segment of SEQ ID NO: 26 in the TRAC gene. The human patient is subject to a lymphodepletion treatment prior to administration of the population of genetically engineered T cells.

I. Anti-CD19 CAR T Cells

Disclosed herein are anti-CD19 CAR T cells (e.g., CTX110 cells) for use in treating B cell malignancies. In some embodiments, the anti-CD19 CAR T cells are human T cells expressing an anti-CD19 CAR and having a disrupted TRAC gene, a disrupted B2M gene, or a combination thereof. In specific examples, the anti-CD19 CAR T cells express an anti-CD19 CAR and have endogenous TRAC and B2M genes disrupted.

(i) Anti-CD19 Chimeric Antigen Receptor (CAR)

The genetically engineered immune cells such as T cells disclosed here express a chimeric antigen receptor (CAR) that binds CD19 (an anti-CD19 CAR). A chimeric antigen receptor (CAR) refers to an artificial immune cell receptor that is engineered to recognize and bind to an antigen expressed by undesired cells, for example, disease cells such as cancer cells. A T cell that expresses a CAR polypeptide is referred to as a CAR T cell. CARs have the ability to redirect T-cell specificity and reactivity toward a selected target in a non-MHC-restricted manner. The non-MHC-restricted antigen recognition gives CAR-T cells the ability to recognize an antigen independent of antigen processing, thus bypassing a major mechanism of tumor escape. Moreover, when expressed on T-cells, CARs advantageously do not dimerize with endogenous T-cell receptor (TCR) alpha and beta chains.

There are various generations of CARs, each of which contains different components. First generation CARs join an antibody-derived scFv to the CD3zeta ((or z) intracellular signaling domain of the T-cell receptor through hinge and transmembrane domains. Second generation CARs incorporate an additional co-stimulatory domain, e.g., CD28, 4-1BB (41BB), or ICOS, to supply a costimulatory signal. Third-generation CARs contain two costimulatory domains (e.g., a combination of CD27, CD28, 4-1BB, ICOS, or OX40) fused with the TCR CD3ζ chain. Maude et al., Blood. 2015; 125(26):4017-4023; Kakarla and Gottschalk, Cancer J. 2014; 20(2):151-155). Any of the various generations of CAR constructs is within the scope of the present disclosure.

Generally, a CAR is a fusion polypeptide comprising an extracellular domain that recognizes a target antigen (e.g., a single chain fragment (scFv) of an antibody or other antibody fragment) and an intracellular domain comprising a signaling domain of the T-cell receptor (TCR) complex (e.g., CD3ζ) and, in most cases, a co-stimulatory domain. (Enblad et al., Human Gene Therapy. 2015; 26(8):498-505). A CAR construct may further comprise a hinge and transmembrane domain between the extracellular domain and the intracellular domain, as well as a signal peptide at the N-terminus for surface expression. Examples of signal peptides include MLLLVTSLLLCELPHPAFLLIP (SEQ ID NO: 30) and MALPVTALLLPLALLLHAARP (SEQ ID NO: 31). Other signal peptides may be used.

The anti-CD19 CAR may comprise an anti-CD19 single-chain variable fragment (scFv) specific for CD19, followed by hinge domain and transmembrane domain (e.g., a CD8 hinge and transmembrane domain) that is fused to an intracellular co-signaling domain (e.g., a CD28 co-stimulatory domain) and a CD3ζ signaling domain. Exemplary components for use in constructing the anti-CD19 CAR disclosed herein can be found in the Sequence Table provided below.

(a) Antigen Binding Extracellular Domain

The antigen-binding extracellular domain is the region of a CAR polypeptide that is exposed to the extracellular fluid when the CAR is expressed on cell surface. In some instances, a signal peptide may be located at the N-terminus to facilitate cell surface expression. In some embodiments, the antigen binding domain can be a single-chain variable fragment (scFv, which may include an antibody heavy chain variable region ($V_H$) and an antibody light chain variable region ($V_L$) (in either orientation). In some instances, the $V_H$ and $V_L$ fragment may be linked via a peptide linker. The linker, in some embodiments, includes hydrophilic residues with stretches of glycine and serine for flexibility as well as stretches of glutamate and lysine for added solubility. The scFv fragment retains the antigen-binding specificity of the parent antibody, from which the scFv fragment is derived. In some embodiments, the scFv may comprise humanized $V_H$ and/or $V_L$ domains. In other embodiments, the $V_H$ and/or $V_L$ domains of the scFv are fully human.

The antigen-binding extracellular domain in the CAR polypeptide disclosed herein is specific to CD19 (e.g., human CD19). In some examples, the antigen-binding extracellular domain may comprise a scFv extracellular domain capable of binding to CD19. The anti-CD19 scFv may comprise a heavy chain variable domain ($V_H$) having the same heavy chain complementary determining regions (CDRs) as those in SEQ ID NO: 51 and a light chain variable domain ($V_L$) having the same light chain CDRs as those in SEQ ID NO: 52. Two antibodies having the same $V_H$ and/or $V_L$ CDRs means that their CDRs are identical when determined by the same approach (e.g., the Kabat approach, the Chothia approach, the AbM approach, the Contact approach, or the IMGT approach as known in the art. See, e.g., bioinf.org.uk/abs/). In some examples, the anti-CD19 scFv comprises the $V_H$ of SEQ ID NO: 51 and/or the $V_L$ of SEQ ID NO: 52. In specific examples, the anti-CD19 scFv may comprise the amino acid sequence of SEQ ID NO: 47.

(b) Transmembrane Domain

The anti-CD19 CAR polypeptide disclosed herein may contain a transmembrane domain, which can be a hydrophobic alpha helix that spans the membrane. As used herein, a "transmembrane domain" refers to any protein structure that is thermodynamically stable in a cell membrane, preferably a eukaryotic cell membrane. The transmembrane domain can provide stability of the CAR containing such.

In some embodiments, the transmembrane domain of a CAR as provided herein can be a CD8 transmembrane domain. In other embodiments, the transmembrane domain can be a CD28 transmembrane domain. In yet other embodiments, the transmembrane domain is a chimera of a CD8 and CD28 transmembrane domain. Other transmembrane domains may be used as provided herein. In one specific example, the transmembrane domain in the anti-CD19 CAR is a CD8α transmembrane domain having the amino acid sequence of SEQ ID NO: 32.

(c) Hinge Domain

In some embodiments, a hinge domain may be located between an extracellular domain (comprising the antigen binding domain) and a transmembrane domain of a CAR, or between a cytoplasmic domain and a transmembrane domain of the CAR. A hinge domain can be any oligopeptide or polypeptide that functions to link the transmembrane domain to the extracellular domain and/or the cytoplasmic domain in the polypeptide chain. A hinge domain may function to provide flexibility to the CAR, or domains thereof, or to prevent steric hindrance of the CAR, or domains thereof.

In some embodiments, a hinge domain may comprise up to 300 amino acids (e.g., 10 to 100 amino acids, or 5 to 20 amino acids). In some embodiments, one or more hinge domain(s) may be included in other regions of a CAR. In some embodiments, the hinge domain may be a CD8 hinge domain. Other hinge domains may be used.

(d) Intracellular Signaling Domains

Any of the anti-CD19 CAR constructs disclosed herein contain one or more intracellular signaling domains (e.g., CD3ζ, and optionally one or more co-stimulatory domains), which are the functional end of the receptor. Following antigen recognition, receptors cluster and a signal is transmitted to the cell.

CD3ζ is the cytoplasmic signaling domain of the T cell receptor complex. CD3ζ contains three (3) immunoreceptor tyrosine-based activation motif (ITAM)s, which transmit an activation signal to the T cell after the T cell is engaged with a cognate antigen. In many cases, CD3ζ provides a primary T cell activation signal but not a fully competent activation signal, which requires a co-stimulatory signaling. In some examples, the anti-CD19 CAR construct disclosed herein comprise a CD3ζ cytoplasmic signaling domain, which may have the amino acid sequence of SEQ ID NO: 38.

In some embodiments, the anti-CD19 CAR polypeptides disclosed herein may further comprise one or more co-stimulatory signaling domains. For example, the co-stimulatory domains of CD28 and/or 4-1BB may be used to transmit a full proliferative/survival signal, together with the primary signaling mediated by CD3ζ. In some examples, the CAR disclosed herein comprises a CD28 co-stimulatory molecule, for example, a CD28 co-stimulatory signaling domain having the amino acid sequence of SEQ ID NO:36. In other examples, the CAR disclosed herein comprises a 4-1BB co-stimulatory molecule, for example, a 4-1BB co-stimulatory signaling domain having the amino acid sequence of SEQ ID NO: 34.

In specific examples, an anti-CD19 CAR disclosed herein may include a CD3ζ signaling domain (e.g., SEQ ID NO: 38) and a CD28 co-stimulatory domain (e.g., SEQ ID NO: 36).

It should be understood that methods described herein encompasses more than one suitable CAR that can be used to produce genetically engineered T cells expressing the CAR, for example, those known in the art or disclosed herein. Examples can be found in, e.g., International Application Number PCT/IB2018/001619, filed May 11, 2018, which published as WO 2019/097305A2, and International Application Number PCT/IB2019/000500, filed May 10, 2019, the relevant disclosures of each of the prior applications are incorporated by reference herein for the purpose and subject matter referenced herein.

In specific examples, the anti-CD19 CAR disclosed herein may comprise the amino acid sequence of SEQ ID NO: 40, which may be encoded by the nucleotide sequence of SEQ ID NO: 39. See the sequence table provided below.

In the genetically engineered T cells disclosed herein, a nucleic acid comprising the coding sequence of the anti-CD19 CAR, and optionally regulatory sequences for expression of the anti-CD19 CAR (e.g., a promoter such as the EF1a promoter provided in the sequence Table) may be inserted into a genomic locus of interest. In some examples, the nucleic acid is inserted in the endogenous TRAC gene locus, thereby disrupting expression of the TRAC gene. In specific examples, the nucleic acid may replace a fragment in the TRAC gene, for example, a fragment comprising the nucleotide sequence of SEQ ID NO: 26.

(ii) Knock-Out of TRAC and B2M Genes

The anti-CD19 CAR-T cells disclosed herein may further have a disrupted TRAC gene, a disrupted B2M gene, or a combination thereof. The disruption of the TRAC locus results in loss of expression of the T cell receptor (TCR) and is intended to reduce the probability of Graft versus Host Disease (GvHD), while the disruption of the β2M locus results in lack of expression of the major histocompatibility complex type I (MHC I) proteins and is intended to improve persistence by reducing the probability of host rejection. The addition of the anti-CD19 CAR directs the modified T cells towards CD19-expressing tumor cells.

As used herein, the term "a disrupted gene" refers to a gene containing one or more mutations (e.g., insertion, deletion, or nucleotide substitution, etc.) relative to the wild-type counterpart so as to substantially reduce or completely eliminate the activity of the encoded gene product. The one or more mutations may be located in a non-coding region, for example, a promoter region, a regulatory region that regulates transcription or translation; or an intron region. Alternatively, the one or more mutations may be located in a coding region (e.g., in an exon). In some instances, the disrupted gene does not express or expresses a substantially reduced level of the encoded protein. In other instances, the disrupted gene expresses the encoded protein in a mutated form, which is either not functional or has substantially reduced activity. In some embodiments, a disrupted gene is a gene that does not encode functional protein. In some embodiments, a cell that comprises a disrupted gene does not express (e.g., at the cell surface) a detectable level (e.g. by antibody, e.g., by flow cytometry) of the protein encoded by the gene. A cell that does not express a detectable level of the protein may be referred to as a knockout cell. For example, a cell having a β2M gene edit may be considered a β2M knockout cell if β2M protein cannot be detected at the cell surface using an antibody that specifically binds β2M protein.

In some embodiments, a disrupted gene may be described as comprising a mutated fragment relative to the wild-type counterpart. The mutated fragment may comprise a deletion, a nucleotide substitution, an addition, or a combination thereof. In other embodiments, a disrupted gene may be described as having a deletion of a fragment that is present in the wild-type counterpart. In some instances, the 5' end of the deleted fragment may be located within the gene region targeted by a designed guide RNA such as those disclosed herein (known as on-target sequence) and the 3' end of the deleted fragment may go beyond the targeted region. Alternatively, the 3' end of the deleted fragment may be located within the targeted region and the 5' end of the deleted fragment may go beyond the targeted region.

In some instances, the disrupted TRAC gene in the anti-CD19 CAR-T cells disclosed herein may comprise a deletion, for example, a deletion of a fragment in Exon 1 of the TRAC gene locus. In some examples, the disrupted TRAC gene comprises a deletion of a fragment comprising the nucleotide sequence of SEQ ID NO: 26, which is the target site of TRAC guide RNA TA-1. See sequence table below. In some examples, the fragment of SEQ ID NO: 26 may be replaced by a nucleic acid encoding the anti-CD19 CAR. Such a disrupted TRAC gene may comprise the nucleotide sequence of SEQ ID NO: 39.

The disrupted B2M gene in the anti-CD19 CAR-T cells disclosed herein may be generated using the CRISPR/Cas technology. In some examples, a B2M gRNA provided in the sequence table below can be used. The disrupted B2M gene may comprise a nucleotide sequence of any one of SEQ ID Nos: 9-14.

(iii) Exemplary Population of Anti-CD19 CAR-T Cells for Allogeneic Therapy

Also provided herein is population of genetically engineered immune cells (e.g., T cells such as human T cells) comprising the anti-CD19 CAR-T cells disclosed herein, which express any of the anti-CD19 CAR disclosed herein (e.g., the anti-CD19 CAR comprising the amino acid sequence of SEQ ID NO: 40), and a disrupted TRAC gene and/or a disrupted B2M gene as also disclosed herein. In some examples, the population of genetically engineered T cells are CTX110 cells, which are CD19-directed T cells having disrupted TRAC gene and B2M gene. The nucleic acid encoding the anti-CD19 CAR can be inserted in the disrupted TRAC gene at the site of SEQ ID NO: 26, which is replaced by the nucleic acid encoding the anti-CD19 CAR, thereby disrupting expression of the TRAC gene. The disrupted TRAC gene in the CTX110 cells may comprise the nucleotide sequence of SEQ ID NO: 39.

CTX110 cells can be produced via ex vivo genetic modification using the CRISPR/Cas9 (Clustered Regularly Interspaced Short Palindromic Repeats/CRISPR associated protein 9) technology to disrupt targeted genes (TRAC and B2M genes), and adeno-associated virus (AAV) transduction to deliver the anti-CD19 CAR construct. CRISPR-Cas9-mediated gene editing involves two guide RNAs (sgRNAs): TA-1 sgRNA (SEQ ID NO: 18), which targets the TRAC locus, and B2M-1 sgRNA (SEQ ID NO: 20), which targets the 02M locus. For any of the gRNA sequences provided herein, those that do not explicitly indicate modifications are meant to encompass both unmodified sequences and sequences having any suitable modifications.

The anti-CD19 CAR of CTX110 cells is composed of an anti-CD19 single-chain antibody fragment (scFv, which may comprise the amino acid sequence of SEQ ID NO: 47), followed by a CD8 hinge and transmembrane domain (e.g., comprising the amino acid sequence of SEQ ID NO: 32) that is fused to an intracellular co-signaling domain of CD28 (e.g., SEQ ID NO: 36) and a CD3ζ signaling domain (e.g., SEQ ID NO: 38). In specific examples, the anti-CD19 CAR in CTX110 cells comprises the amino acid sequence of SEQ ID NO:40.

In some embodiments, at least 30% of a population of CTX110 cells express a detectable level of the anti-CD19 CAR. For example, at least 40%, at least 50%, at least 60%, at least 70%, at least 75%, at least 80%, at least 85%, at least 90%, or at least 95% of the CTX110 cells express a detectable level of the anti-CD19 CAR.

In some embodiments, at least 50% of a population of CTX110 cells may not express a detectable level of β2M surface protein. For example, at least 55%, at least 60%, at least 70%, at least 75%, at least 80%, at least 85%, at least 90%, or at least 95% of the CTX110 cells may not express a detectable level of β2M surface protein. In some embodiments, 50%-100%, 50%-90%, 50%-80%, 50%-70%, 50%-60%, 60%-100%, 60%-90%, 60%-80%, 60%-70%, 70%-100%, 70%-90%, 70%-80%, 80%-100%, 80%-90%, or 90%-100% of the engineered T cells of a population does not express a detectable level of β2M surface protein.

Alternatively or in addition, at least 50% of a population of CTX110 cells may not express a detectable level of TCR surface protein. For example, at least 55%, at least 60%, at least 70%, at least 75%, at least 80%, at least 85%, at least 90%, or at least 95% of the CTX110 cells may not express a detectable level of TCR surface protein. In some embodiments, 50%-100%, 50%-90%, 50%-80%, 50%-70%, 50%-60%, 60%-100%, 60%-90%, 60%-80%, 60%-70%, 70%-100%, 70%-90%, 70%-80%, 80%-100%, 80%-90%, or 90%-100% of the engineered T cells of a population does not express a detectable level of TRAC surface protein. In specific examples, more than 90% (e.g., more than 99.5%) of the CTX110 cells do not express a detectable TCR surface protein.

In some embodiments, a substantial percentage of the population of CTX110 T cells may comprise more than one gene edit, which results in a certain percentage of cells not expressing more than one gene and/or protein.

For example, at least 50% of a population of CTX110 cells may not express a detectable level of two surface proteins, e.g., does not express a detectable level of 02M and TRAC proteins. In some embodiments, 50%-100%, 50%-90%, 50%-80%, 50%-70%, 50%-60%, 60%-100%, 60%-90%, 60%-80%, 60%-70%, 70%-100%, 70%-90%, 70%-80%, 80%-100%, 80%-90%, or 90%-100% of the CTX110 T cells do not express a detectable level of TRAC and B2M surface proteins. In another example, at least 50% of a population of the CTX110 cells do not express a detectable level of TRAC and B2M surface proteins.

In some embodiments, the population of CTX110 T cells may comprise more than one gene edit (e.g., in more than one gene), which may be an edit described herein. For example, the population of CTX110 T cells may comprise a disrupted TRAC gene via the CRISPR/Cas technology using the TA-1 TRAC gRNA. In some examples, the CTX110 cells may comprise a deletion in the TRAC gene relative to unmodified T cells. For example, the CTX110 T cells may comprise a deletion of the fragment AGAGCAACAGTGCTGTGGCC (SEQ ID NO: 26) in the TRAC gene. This fragment can be replaced by the nucleic acid encoding the anti-CD19 CAR (e.g., SEQ ID NO: 39). Alternatively or in addition, the population of CTX110 cells may comprise a disrupted β2M gene via CRISPR/Cas9 technology using the gRNA of B2M-1. Such CTX110 cells may comprise Indels in the β2M gene, which comprise one or more of the nucleotide sequences of SEQ ID NOs: 9-14. In specific examples, CTX110 cells comprise ≥30% CAR$^+$ T cells, ≤50% B2M$^+$ cells, and ≤30% TCRαβ$^+$ cells. In additional specific examples, CTX110 cells comprise ≥30% CAR$^+$ T cells, ≤30% B2M$^+$ cells, and ≤0.5% TCRαβ+ cells.

See also WO 2019/097305A2, and WO2019215500, the relevant disclosures of each of which are incorporated by reference for the subject matter and purpose referenced herein.

(iv) Pharmaceutical Compositions

In some aspects, the present disclosure provides pharmaceutical compositions comprising any of the populations of genetically engineered anti-CD19 CAR T cells as disclosed herein, for example, CTX110 cells, and a pharmaceutically acceptable carrier. Such pharmaceutical compositions can be used in cancer treatment in human patients, which is also disclosed herein.

As used herein, the term "pharmaceutically acceptable" refers to those compounds, materials, compositions, and/or dosage forms which are, within the scope of sound medical judgment, suitable for use in contact with the tissues, organs, and/or bodily fluids of the subject without excessive toxicity, irritation, allergic response, or other problems or complications commensurate with a reasonable benefit/risk ratio. As used herein, the term "pharmaceutically acceptable carrier" refers to solvents, dispersion media, coatings, antibacterial agents, antifungal agents, isotonic and absorption delaying agents, or the like that are physiologically compatible. The compositions can include a pharmaceutically acceptable salt, e.g., an acid addition salt or a base addition salt. See, e.g., Berge et al., (1977) J Pharm Sci 66:1-19.

In some embodiments, the pharmaceutical composition further comprises a pharmaceutically acceptable salt. Non-limiting examples of pharmaceutically acceptable salts include acid addition salts (formed from a free amino group of a polypeptide with an inorganic acid (e.g., hydrochloric or phosphoric acids), or an organic acid such as acetic, tartaric, mandelic, or the like). In some embodiments, the salt formed with the free carboxyl groups is derived from an inorganic base (e.g., sodium, potassium, ammonium, calcium or ferric hydroxides), or an organic base such as isopropylamine, trimethylamine, 2-ethylamino ethanol, histidine, procaine, or the like).

In some embodiments, the pharmaceutical composition disclosed herein comprises a population of the genetically engineered anti-CD19 CAR-T cells (e.g., CTX110 cells) suspended in a cryopreservation solution (e.g., CryoStor® C55). The cryopreservation solution for use in the present disclosure may also comprise adenosine, dextrose, dextran-40, lactobionic acid, sucrose, mannitol, a buffer agent such as N-)2-hydroxyethyl) piperazine-N'-(2-ethanesulfonic acid) (HEPES), one or more salts (e.g., calcium chloride, magnesium chloride, potassium chloride, potassium bicarbonate, potassium phosphate, etc.), one or more base (e.g., sodium hydroxide, potassium hydroxide, etc.), or a combination thereof. Components of a cryopreservation solution may be dissolved in sterile water (injection quality). Any of the cryopreservation solution may be substantially free of serum (undetectable by routine methods).

In some instances, a pharmaceutical composition comprising a population of genetically engineered anti-CD19 CAR-T cells such as the CTX110 cells suspended in a cryopreservation solution (e.g., substantially free of serum) may be placed in storage vials.

Any of the pharmaceutical compositions disclosed herein, comprising a population of genetically engineered anti-CD19 CAR T cells as also disclosed herein (e.g., CTX110 cells), which optionally may be suspended in a cryopreservation solution as disclosed herein may be stored in an environment that does not substantially affect viability and bioactivity of the T cells for future use, e.g., under conditions commonly applied for storage of cells and tissues. In some examples, the pharmaceutical composition may be stored in the vapor phase of liquid nitrogen at ≤−135° C. No significant changes were observed with respect to appearance, cell count, viability, % CAR$^+$ T cells, % TCR$^+$ T cells, and % B2M$^+$ T cells after the cells have been stored under such conditions for a period of time.

II. Preparation of Genetically Engineered Immune Cells

Any suitable gene editing methods known in the art can be used for making the genetically engineered immune cells (e.g., T cells such as CTX110 cells) disclosed herein, for example, nuclease-dependent targeted editing using zinc-finger nucleases (ZFNs), transcription activator-like effector nucleases (TALENs), or RNA-guided CRISPR-Cas9 nucleases (CRISPR/Cas9; Clustered Regular Interspaced Short Palindromic Repeats Associated 9). In specific examples, the genetically engineered immune cells such as CTX110 cells are produced by the CRISPR technology in combination with homologous recombination using an adeno-associated viral vector (AAV) as a donor template.

(i) CRISPR-Cas9-Mediated Gene Editing System

The CRISPR-Cas9 system is a naturally-occurring defense mechanism in prokaryotes that has been repurposed as an RNA-guided DNA-targeting platform used for gene editing. It relies on the DNA nuclease Cas9, and two noncoding RNAs, crisprRNA (crRNA) and trans-activating RNA (tracrRNA), to target the cleavage of DNA. CRISPR is an abbreviation for Clustered Regularly Interspaced Short Palindromic Repeats, a family of DNA sequences found in the genomes of bacteria and archaea that contain fragments of DNA (spacer DNA) with similarity to foreign DNA previously exposed to the cell, for example, by viruses that have infected or attacked the prokaryote. These fragments of DNA are used by the prokaryote to detect and destroy similar foreign DNA upon re-introduction, for example, from similar viruses during subsequent attacks. Transcription of the CRISPR locus results in the formation of an RNA molecule comprising the spacer sequence, which associates with and targets Cas (CRISPR-associated) proteins able to recognize and cut the foreign, exogenous DNA. Numerous types and classes of CRISPR/Cas systems have been described (see, e.g., Koonin et al., (2017) Curr Opin Microbiol 37:67-78).

crRNA drives sequence recognition and specificity of the CRISPR-Cas9 complex through Watson-Crick base pairing typically with a 20 nucleotide (nt) sequence in the target DNA. Changing the sequence of the 5' 20 nt in the crRNA allows targeting of the CRISPR-Cas9 complex to specific loci. The CRISPR-Cas9 complex only binds DNA sequences that contain a sequence match to the first 20 nt of the crRNA, if the target sequence is followed by a specific short DNA motif (with the sequence NGG) referred to as a protospacer adjacent motif (PAM).

TracrRNA hybridizes with the 3' end of crRNA to form an RNA-duplex structure that is bound by the Cas9 endonuclease to form the catalytically active CRISPR-Cas9 complex, which can then cleave the target DNA.

Once the CRISPR-Cas9 complex is bound to DNA at a target site, two independent nuclease domains within the Cas9 enzyme each cleave one of the DNA strands upstream of the PAM site, leaving a double-strand break (DSB) where both strands of the DNA terminate in a base pair (a blunt end).

After binding of CRISPR-Cas9 complex to DNA at a specific target site and formation of the site-specific DSB, the next key step is repair of the DSB. Cells use two main DNA repair pathways to repair the DSB: non-homologous end joining (NHEJ) and homology-directed repair (HDR).

NHEJ is a robust repair mechanism that appears highly active in the majority of cell types, including non-dividing cells. NHEJ is error-prone and can often result in the removal or addition of between one and several hundred nucleotides at the site of the DSB, though such modifications are typically <20 nt. The resulting insertions and deletions (indels) can disrupt coding or noncoding regions of genes. Alternatively, HDR uses a long stretch of homologous donor DNA, provided endogenously or exogenously, to repair the DSB with high fidelity. HDR is active only in dividing cells, and occurs at a relatively low frequency in most cell types. In many embodiments of the present disclosure, NHEJ is utilized as the repair operant.

(a) Cas9

In some embodiments, the Cas9 (CRISPR associated protein 9) endonuclease is used in a CRISPR method for making the genetically engineered T cells as disclosed herein. The Cas9 enzyme may be one from *Streptococcus pyogenes*, although other Cas9 homologs may also be used. It should be understood, that wild-type Cas9 may be used or modified versions of Cas9 may be used (e.g., evolved versions of Cas9, or Cas9 orthologues or variants), as provided herein. In some embodiments, Cas9 comprises a *Streptococcus pyogenes*-derived Cas9 nuclease protein that has been engineered to include C- and N-terminal SV40 large T antigen nuclear localization sequences (NLS). The resulting Cas9 nuclease (sNLS-spCas9-sNLS) is a 162 kDa protein that is produced by recombinant *E. coli* fermentation and purified by chromatography. The spCas9 amino acid sequence can be found as UniProt Accession No. Q99ZW2, which is provided herein as SEQ ID NO: 55.

(b) Guide RNAs (gRNAs)

CRISPR-Cas9-mediated gene editing as described herein includes the use of a guide RNA or a gRNA. As used herein, a "gRNA" refers to a genome-targeting nucleic acid that can direct the Cas9 to a specific target sequence within a TRAC gene or a β2M gene for gene editing at the specific target sequence. A guide RNA comprises at least a spacer sequence that hybridizes to a target nucleic acid sequence within a target gene for editing, and a CRISPR repeat sequence.

An exemplary gRNA targeting a TRAC gene is provided in SEQ ID NO: 18 or 22. See the sequence table below. See also WO 2019/097305A2, the relevant disclosures of which are incorporated by reference herein for the subject matter and purpose referenced herein. Other gRNA sequences may be designed using the TRAC gene sequence located on chromosome 14 (GRCh38: chromosome 14: 22,547,506-22,552,154; Ensembl; ENSG00000277734). In some embodiments, gRNAs targeting the TRAC genomic region and Cas9 create breaks in the TRAC genomic region resulting Indels in the TRAC gene disrupting expression of the mRNA or protein.

An exemplary gRNA targeting a β2M gene is provided in SEQ ID NO: 20 or 24. See the sequence table below. See also WO 2019/097305A2, the relevant disclosures of which are incorporated by reference herein for the purpose and subject matter referenced herein. Other gRNA sequences may be designed using the β2M gene sequence located on Chromosome 15 (GRCh38 coordinates: Chromosome 15: 44,711,477-44,718,877; Ensembl: ENSG00000166710). In some embodiments, gRNAs targeting the β2M genomic region and RNA-guided nuclease create breaks in the β2M genomic region resulting in Indels in the β2M gene disrupting expression of the mRNA or protein.

In Type II systems, the gRNA also comprises a second RNA called the tracrRNA sequence. In the Type II gRNA, the CRISPR repeat sequence and tracrRNA sequence hybridize to each other to form a duplex. In the Type V gRNA, the crRNA forms a duplex. In both systems, the duplex binds a site-directed polypeptide, such that the guide RNA and site-direct polypeptide form a complex. In some embodiments, the genome-targeting nucleic acid provides target specificity to the complex by virtue of its association with the site-directed polypeptide. The genome-targeting nucleic acid thus directs the activity of the site-directed polypeptide.

As is understood by the person of ordinary skill in the art, each guide RNA is designed to include a spacer sequence complementary to its genomic target sequence. See Jinek et al., Science, 337, 816-821 (2012) and Deltcheva et al., Nature, 471, 602-607 (2011).

In some embodiments, the genome-targeting nucleic acid (e.g., gRNA) is a double-molecule guide RNA. In some embodiments, the genome-targeting nucleic acid (e.g., gRNA) is a single-molecule guide RNA.

A double-molecule guide RNA comprises two strands of RNA molecules. The first strand comprises in the 5' to 3' direction, an optional spacer extension sequence, a spacer sequence and a minimum CRISPR repeat sequence. The second strand comprises a minimum tracrRNA sequence (complementary to the minimum CRISPR repeat sequence), a 3' tracrRNA sequence and an optional tracrRNA extension sequence.

A single-molecule guide RNA (referred to as a "sgRNA") in a Type II system comprises, in the 5' to 3' direction, an optional spacer extension sequence, a spacer sequence, a minimum CRISPR repeat sequence, a single-molecule guide linker, a minimum tracrRNA sequence, a 3' tracrRNA sequence and an optional tracrRNA extension sequence. The optional tracrRNA extension may comprise elements that contribute additional functionality (e.g., stability) to the guide RNA. The single-molecule guide linker links the minimum CRISPR repeat and the minimum tracrRNA sequence to form a hairpin structure. The optional tracrRNA extension comprises one or more hairpins. A single-molecule guide RNA in a Type V system comprises, in the 5' to 3' direction, a minimum CRISPR repeat sequence and a spacer sequence.

The "target sequence" is in a target gene that is adjacent to a PAM sequence and is the sequence to be modified by Cas9. The "target sequence" is on the so-called PAM-strand in a "target nucleic acid," which is a double-stranded molecule containing the PAM-strand and a complementary non-PAM strand. One of skill in the art recognizes that the gRNA spacer sequence hybridizes to the complementary sequence located in the non-PAM strand of the target nucleic acid of interest. Thus, the gRNA spacer sequence is the RNA equivalent of the target sequence.

For example, if the TRAC target sequence is 5'-AGAGCAACAGTGCTGTGGCC-3' (SEQ ID NO: 26), then the gRNA spacer sequence is 5'-AGAGCAACAGUGCUGUGGCC-3' (SEQ ID NO: 19). In another example, if the 02M target sequence is 5'-GCTACTCTCTCTTTCTGGCC-3' (SEQ ID NO: 27), then the gRNA spacer sequence is 5'-GCUACUCUCUCUUUCUGGCC-3' (SEQ ID NO: 21). The spacer of a gRNA interacts with a target nucleic acid of interest in a sequence-specific manner via hybridization (i.e., base pairing). The nucleotide sequence of the spacer thus varies depending on the target sequence of the target nucleic acid of interest.

In a CRISPR/Cas system herein, the spacer sequence is designed to hybridize to a region of the target nucleic acid that is located 5' of a PAM recognizable by a Cas9 enzyme used in the system. The spacer may perfectly match the target sequence or may have mismatches. Each Cas9 enzyme has a particular PAM sequence that it recognizes in a target DNA. For example, S. pyogenes recognizes in a target nucleic acid a PAM that comprises the sequence 5'-NRG-3', where R comprises either A or G, where N is any nucleotide and N is immediately 3' of the target nucleic acid sequence targeted by the spacer sequence.

In some embodiments, the target nucleic acid sequence has 20 nucleotides in length. In some embodiments, the target nucleic acid has less than 20 nucleotides in length. In some embodiments, the target nucleic acid has more than 20 nucleotides in length. In some embodiments, the target nucleic acid has at least: 5, 10, 15, 16, 17, 18, 19, 20, 21, 22, 23, 24, 25, 30 or more nucleotides in length. In some embodiments, the target nucleic acid has at most: 5, 10, 15, 16, 17, 18, 19, 20, 21, 22, 23, 24, 25, 30 or more nucleotides in length. In some embodiments, the target nucleic acid sequence has 20 bases immediately 5' of the first nucleotide of the PAM. For example, in a sequence comprising 5'-NNNNNNNNNNNNNNNNNNNNNRG-3', the target nucleic acid can be the sequence that corresponds to the Ns, wherein N can be any nucleotide, and the underlined NRG sequence is the S. pyogenes PAM. Examples are provides as SEQ ID NOs: 15-17.

The guide RNA disclosed herein may target any sequence of interest via the spacer sequence in the crRNA. In some embodiments, the degree of complementarity between the spacer sequence of the guide RNA and the target sequence in the target gene can be about 60%, 65%, 70%, 75%, 80%, 85%, 90%, 95%, 97%, 98%, 99%, or 100%. In some embodiments, the spacer sequence of the guide RNA and the target sequence in the target gene is 100% complementary. In other embodiments, the spacer sequence of the guide RNA and the target sequence in the target gene may contain up to 10 mismatches, e.g., up to 9, up to 8, up to 7, up to 6, up to 5, up to 4, up to 3, up to 2, or up to 1 mismatch.

Non-limiting examples of gRNAs that may be used as provided herein are provided in WO 2019/097305A2, and WO2019/215500, the relevant disclosures of each of which are herein incorporated by reference for the purposes and subject matter referenced herein. For any of the gRNA sequences provided herein, those that do not explicitly indicate modifications are meant to encompass both unmodified sequences and sequences having any suitable modifications.

The length of the spacer sequence in any of the gRNAs disclosed herein may depend on the CRISPR/Cas9 system and components used for editing any of the target genes also disclosed herein. For example, different Cas9 proteins from different bacterial species have varying optimal spacer sequence lengths. Accordingly, the spacer sequence may have 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, or more than 50 nucleotides in length. In some embodiments, the spacer sequence may have 18-24 nucleotides in length. In some embodiments, the targeting sequence may have 19-21 nucleotides in length. In some embodiments, the spacer sequence may comprise 20 nucleotides in length.

In some embodiments, the gRNA can be a sgRNA, which may comprise a 20 nucleotide spacer sequence at the 5' end of the sgRNA sequence. In some embodiments, the sgRNA may comprise a less than 20 nucleotide spacer sequence at the 5' end of the sgRNA sequence. In some embodiments, the sgRNA may comprise a more than 20 nucleotide spacer sequence at the 5' end of the sgRNA sequence. In some embodiments, the sgRNA comprises a variable length spacer sequence with 17-30 nucleotides at the 5' end of the sgRNA sequence.

In some embodiments, the sgRNA comprises no uracil at the 3' end of the sgRNA sequence. In other embodiments, the sgRNA may comprise one or more uracil at the 3' end of the sgRNA sequence. For example, the sgRNA can comprise 1-8 uracil residues, at the 3' end of the sgRNA sequence, e.g., 1, 2, 3, 4, 5, 6, 7, or 8 uracil residues at the 3' end of the sgRNA sequence.

Any of the gRNAs disclosed herein, including any of the sgRNAs, may be unmodified. Alternatively, it may contain one or more modified nucleotides and/or modified backbones. For example, a modified gRNA such as a sgRNA can comprise one or more 2'-O-methyl phosphorothioate nucleotides, which may be located at either the 5' end, the 3' end, or both.

In certain embodiments, more than one guide RNAs can be used with a CRISPR/Cas nuclease system. Each guide RNA may contain a different targeting sequence, such that the CRISPR/Cas system cleaves more than one target nucleic acid. In some embodiments, one or more guide RNAs may have the same or differing properties such as activity or stability within the Cas9 RNP complex. Where more than one guide RNA is used, each guide RNA can be encoded on the same or on different vectors. The promoters used to drive expression of the more than one guide RNA is the same or different.

It should be understood that more than one suitable Cas9 and more than one suitable gRNA can be used in methods described herein, for example, those known in the art or disclosed herein. In some embodiments, methods comprise a Cas9 enzyme and/or a gRNA known in the art. Examples can be found in, e.g., WO 2019/097305A2, and WO2019/ 215500, the relevant disclosures of each of which are herein incorporated by reference for the purposes and subject matter referenced herein.

(ii) AAV Vectors for Delivery of CAR Constructs to T Cells

A nucleic acid encoding an anti-CD19 CAR construct as disclosed herein can be delivered to a cell using an adeno-associated virus (AAV). AAVs are small viruses which integrate site-specifically into the host genome and can therefore deliver a transgene, such as CAR. Inverted terminal repeats (ITRs) are present flanking the AAV genome and/or the transgene of interest and serve as origins of replication. Also present in the AAV genome are rep and cap proteins which, when transcribed, form capsids which encapsulate the AAV genome for delivery into target cells. Surface receptors on these capsids which confer AAV serotype, which determines which target organs the capsids will primarily bind and thus what cells the AAV will most efficiently infect. There are twelve currently known human AAV serotypes. In some embodiments, the AAV for use in delivering the CAR-coding nucleic acid is AAV serotype 6 (AAV6).

Adeno-associated viruses are among the most frequently used viruses for gene therapy for several reasons. First, AAVs do not provoke an immune response upon administration to mammals, including humans. Second, AAVs are effectively delivered to target cells, particularly when consideration is given to selecting the appropriate AAV serotype. Finally, AAVs have the ability to infect both dividing and non-dividing cells because the genome can persist in the host cell without integration. This trait makes them an ideal candidate for gene therapy.

A nucleic acid encoding an anti-CD19 CAR can be designed to insert into a genomic site of interest in the host T cells. In some embodiments, the target genomic site can be in a safe harbor locus.

In some embodiments, a nucleic acid encoding the anti-CD19 CAR (e.g., via a donor template, which can be carried by a viral vector such as an adeno-associated viral (AAV) vector) can be designed such that it can insert into a location within a TRAC gene to disrupt the TRAC gene in the genetically engineered T cells and express the CAR polypeptide. Disruption of TRAC leads to loss of function of the endogenous TCR. For example, a disruption in the TRAC gene can be created with an endonuclease such as those described herein and one or more gRNAs targeting one or more TRAC genomic regions. Any of the gRNAs specific to a TRAC gene and the target regions can be used for this purpose, e.g., those disclosed herein.

In some examples, a genomic deletion in the TRAC gene and replacement by a CAR coding segment can be created by homology directed repair or HDR (e.g., using a donor template, which may be part of a viral vector such as an adeno-associated viral (AAV) vector).

In some embodiments, a disruption in the TRAC gene can be created with an endonuclease as those disclosed herein and one or more gRNAs targeting one or more TRAC genomic regions, and inserting a CAR coding segment into the TRAC gene.

A donor template as disclosed herein can contain a coding sequence for a CAR. In some examples, the CAR-coding sequence may be flanked by two regions of homology to allow for efficient HDR at a genomic location of interest, for example, at a TRAC gene using CRISPR-Cas9 gene editing technology. In this case, both strands of the DNA at the target locus can be cut by a CRISPR Cas9 enzyme guided by gRNAs specific to the target locus. HDR then occurs to repair the double-strand break (DSB) and insert the donor DNA coding for the CAR. For this to occur correctly, the donor sequence is designed with flanking residues which are complementary to the sequence surrounding the DSB site in the target gene (hereinafter "homology arms"), such as the TRAC gene. These homology arms serve as the template for DSB repair and allow HDR to be an essentially error-free mechanism. The rate of homology directed repair (HDR) is a function of the distance between the mutation and the cut site so choosing overlapping or nearby target sites is important. Templates can include extra sequences flanked by the homologous regions or can contain a sequence that differs from the genomic sequence, thus allowing sequence editing.

Alternatively, a donor template may have no regions of homology to the targeted location in the DNA and may be integrated by NHEJ-dependent end joining following cleavage at the target site.

A donor template can be DNA or RNA, single-stranded and/or double-stranded, and can be introduced into a cell in linear or circular form. If introduced in linear form, the ends of the donor sequence can be protected (e.g., from exonucleolytic degradation) by methods known to those of skill in the art. For example, one or more dideoxynucleotide residues are added to the 3' terminus of a linear molecule and/or self-complementary oligonucleotides are ligated to one or both ends. See, for example, Chang et al., (1987) Proc. Natl. Acad. Sci. USA 84:4959-4963; Nehls et al., (1996) Science 272:886-889. Additional methods for protecting exogenous polynucleotides from degradation include, but are not limited to, addition of terminal amino group(s) and the use of modified internucleotide linkages such as, for example, phosphorothioates, phosphoramidates, and O-methyl ribose or deoxyribose residues.

A donor template can be introduced into a cell as part of a vector molecule having additional sequences such as, for example, replication origins, promoters and genes encoding antibiotic resistance. Moreover, a donor template can be introduced into a cell as naked nucleic acid, as nucleic acid complexed with an agent such as a liposome or poloxamer, or can be delivered by viruses (e.g., adenovirus, AAV, herpesvirus, retrovirus, lentivirus and integrase defective lentivirus (IDLV)).

A donor template, in some embodiments, can be inserted at a site nearby an endogenous promoter (e.g., downstream or upstream) so that its expression can be driven by the endogenous promoter. In other embodiments, the donor template may comprise an exogenous promoter and/or enhancer, for example, a constitutive promoter, an inducible promoter, or tissue-specific promoter to control the expression of the CAR gene. In some embodiments, the exogenous promoter is an EF1α promoter. Other promoters may be used.

Furthermore, exogenous sequences may also include transcriptional or translational regulatory sequences, for example, promoters, enhancers, insulators, internal ribosome entry sites, sequences encoding 2A peptides and/or polyadenylation signals.

To prepare the genetically engineered immune cells (e.g., T cells disclosed herein), immune cells such as T cells from a suitable source may be obtained, e.g., blood cells from a human donor, who may be a healthy donor or a patient need CAR-T cell therapy. The CTX110 cells can be made using blood cells from one or more healthy human donors. Manufacturing from healthy donor cells minimizes the risk of unintentionally transducing malignant lymphoma/leukemia cells and potentially may improve the functionality of the CAR T cells. The components of the CRISPR system (e.g., Cas9 protein and the gRNAs), optionally the AAV donor template, may be delivered into the host immune cells via conventional approaches. In some examples, the Cas9 and the gRNAs can form a ribonucleoprotein complex (RNP), which can be delivered to the host immune cells by electroporation. Optionally, the AAV donor template may be delivered to the immune cells concurrently with the RNP complex. Alternatively, delivery of the RNPs and the AAV donor template can be performed sequentially. In some examples, the T cells may be activated prior to delivery of the gene editing components.

After delivery of the gene editing components and optionally the donor template, the cells may be recovered and expanded in vitro. Gene editing efficiency can be evaluated using routine methods for confirm knock-in of the anti-CD19 CAR and knock-out of the target genes (e.g., TRAC, B2M, or both). In some examples, TCRαβ+ T cells may be removed. Additional information for preparation of the genetically engineered immune cells disclosed herein such as the CTX110 cells can be found in U.S. Patent Application No. 62/934,991, the relevant disclosures of which are incorporated by reference for the purpose and subject matter referenced herein.

III. Allogeneic CAR-T Cell Therapy of B Cell Malignancies

In some aspects, provided herein are methods for treating a human patient having a B cell malignancy using a population of any of the genetically engineered anti-CD19 CAR T cells such as the CTX110 T cells as disclosed herein. The allogeneic anti-CD19 CAR T cell therapy may comprise two stages of treatment: (i) a conditioning regimen (lymphodepleting treatment), which comprises giving one or more doses of one or more lymphodepleting agents to a suitable human patient, and (ii) a treatment regimen (allogeneic anti-CD19 CAR T cell therapy), which comprises administration of the population of allogeneic anti-CD19 CAR T cells such as the CTX110 T cells as disclosed herein to the human patient.

(i) Patient Population

A human patient may be any human subject for whom diagnosis, treatment, or therapy is desired. A human patient may be of any age. In some embodiments, the human patient is an adult (e.g., a person who is at least 18 years old). In some examples, the human patient may have a body weight of 50 kg or higher. In some embodiments, the human patient can be a child.

A human patient to be treated by the methods described herein can be a human patient having, suspected of having, or a risk for having a B cell malignancy. A subject suspected of having a B cell malignancy might show one or more symptoms of B cell malignancy, e.g., unexplained weight loss, fatigue, night sweats, shortness of breath, or swollen glands. A subject at risk for a B cell malignancy can be a subject having one or more of the risk factors for B cell malignancy, e.g., a weakened immune system, age, male, or infection (e.g., Epstein-Barr virus infection). A human patient who needs the anti-CD19 CAR T cell (e.g., CTX110 T cell) treatment may be identified by routine medical examination, e.g., physical examination, laboratory tests, biopsy (e.g., bone marrow biopsy and/or lymph node biopsy), magnetic resonance imaging (MRI) scans, or ultrasound exams.

Examples of B cell malignancies that may be treated using the methods described herein include, but are not limited to, diffuse large B cell lymphoma (DLBCL), high grade B cell lymphoma with MYC and BCL2 and/or BCL6 rearrangement, transformed follicular lymphoma (FL), grade 3b FL, or Richter's transformation of chronic lymphocytic leukemia (CLL). In some examples, the B cell malignancy is DLBCL, e.g., high grade DLBCL or DLBCL not otherwise specified (NOS). In some examples, the B cell malignancy is transformed FL or grade 3b FL. In some examples, the human patient has at least one measurable lesion that is fluorodeoxyglucose positron emission tomography (PET)-positive.

In some embodiment, the human patient to be treated has DLBCL and exhibits pararectal mass, retroperitoneal mass, diffuse lymph nodes (LN), lytic lesions, tonsillar lesion, or a combination thereof. Alternatively or in addition, the human patient may have bone marrow diffusion. In other examples, the human patient is free of bone marrow diffusion.

In some embodiments, the human patient to be treated has transformed FL. Such a human patient may exhibit diffuse LN. In some instances, the human patient may have bone marrow diffusion. In other instances, the human patient may be free of bone marrow diffusion.

A human patient to be treated by methods described herein may be a human patient that has relapsed following a treatment and/or that has been become resistant to a treatment and/or that has been non-responsive to a treatment. As used herein, "relapsed" or "relapses" refers to a B cell malignancy such as those disclosed herein that returns following a period of complete response. Progressive disease refers to an instance when a disease worsens after the last evaluation (e.g., stable disease or partial response). In some embodiments, progression occurs during the treatment. In some embodiments, relapse occurs after the treatment. A lack of response may be determined by routine medical practice. For example, the human patient to be treated by methods described herein may be a human patient that has had one or more lines of prior anti-cancer therapies. In some instances, the human patient may have undergone two or more lines of prior anti-cancer therapies, e.g., a chemotherapy, an immunotherapy, a surgery, or a combination thereof. In some examples, the prior anti-cancer therapies may comprise an anti-CD20 antibody therapy, an anthracycline-containing therapy, or a combination thereof.

In some instances, the human patient has a refractory B cell malignancy. As used herein, "refractory" refers to a B cell malignancy such as those disclosed herein that does not respond to or becomes resistant to a treatment. A human patient having a refractory B cell malignancy may have progressive disease on last therapy, or has stable disease following at least two cycles of therapy with duration of stable disease of up to 6 months (e.g., up to 5 months, up to 4 months, or up to 3 months or up to 2 months or up to 1 month). In some instances, the human patient may have undergone a prior autologous hematopoietic stem cell transplantation (HSCT) and showed no response to such (failed) or have progressed or relapsed after achieving some response. In other instances, the human patient may not be eligible for prior autologous HSCT.

A human patient may be screened to determine whether the patient is eligible to undergo a conditioning regimen (lymphodepleting treatment) and/or an allogeneic anti-CD19 CAR-T cell therapy as disclosed herein. For example, a human patient who is eligible for lymphodepletion treatment does not show one or more of the following features: (a) significant worsening of clinical status, (b) requirement for supplemental oxygen to maintain a saturation level of greater than 90%, (c) uncontrolled cardiac arrhythmia, (d) hypotension requiring vasopressor support, (e) active infection, and (f) grade ≥2 acute neurological toxicity. In another example, a human patient who is eligible for a treatment regimen does not show one or more of the following features: (a) active uncontrolled infection, (b) worsening of clinical status compared to the clinical status prior to lymphodepletion treatment, and (c) grade ≥2 acute neurological toxicity.

A human patient may be screened and excluded from the conditioning regimen and/or treatment regimen based on such screening results. For example, a human patient may be excluded from a conditioning regimen and/or the allogeneic anti-CD19 CAR-T cell therapy, if the patient meets one or more of the following exclusion criteria: (a) has an Eastern Cooperative Oncology Group (ECOG) performance status 0 or 1; (b) adequate renal, liver, cardiac, and/or pulmonary function; (c) free of prior gene therapy or modified cell therapy; (d) free of prior treatment comprising an anti-CD19 antibody; (e) free of prior allogeneic HSCT; (f) free of detectable malignant cells from cerebrospinal fluid; (g) free of brain metastases; (h) free of prior central nervous system disorders; (i) free of unstable angina, arrhythmia, and/or myocardial infarction; (j) free of uncontrolled infection; (k) free of immunodeficiency disorders or autoimmune disorders that require immunosuppressive therapy; and (l) free of infection by human immunodeficiency virus, hepatitis B virus, or hepatitis C virus.

(ii) Conditioning Regimen (Lymphodepleting Therapy)

Any human patients suitable for the treatment methods disclosed herein may receive a lymphodepleting therapy to reduce or deplete the endogenous lymphocyte of the subject.

Lymphodepletion refers to the destruction of endogenous lymphocytes and/or T cells, which is commonly used prior to immunotransplantation and immunotherapy. Lymphodepletion can be achieved by irradiation and/or chemotherapy. A "lymphodepleting agent" can be any molecule capable of reducing, depleting, or eliminating endogenous lymphocytes and/or T cells when administered to a subject. In some embodiments, the lymphodepleting agents are administered in an amount effective in reducing the number of lymphocytes by at least 10%, 20%, 30%, 40%, 50%, 60%, 70%, 80%, 90%, 95%, 96%, 96%, 97%, 98%, or at least 99% as compared to the number of lymphocytes prior to administration of the agents. In some embodiments, the lymphodepleting agents are administered in an amount effective in reducing the number of lymphocytes such that the number of lymphocytes in the subject is below the limits of detection. In some embodiments, the subject is administered at least one (e.g., 2, 3, 4, 5 or more) lymphodepleting agents.

In some embodiments, the lymphodepleting agents are cytotoxic agents that specifically kill lymphocytes. Examples of lymphodepleting agents include, without limitation, fludarabine, cyclophosphamide, bendamustin, 5-fluorouracil, gemcitabine, methotrexate, dacarbazine, melphalan, doxorubicin, vinblastine, cisplatin, oxaliplatin, paclitaxel, docetaxel, irinotecan, etopside phosphate, mitoxantrone, cladribine, denileukin diftitox, or DAB-IL2. In some instances, the lymphodepleting agent may be accompanied with low-dose irradiation. The lymphodepletion effect of the conditioning regimen can be monitored via routine practice.

In some embodiments, the method described herein involves a conditioning regimen that comprises one or more lymphodepleting agents, for example, fludarabine and cyclophosphamide. A human patient to be treated by the method described herein may receive multiple doses of the one or more lymphodepleting agents for a suitable period (e.g., 1-5 days) in the conditioning stage. The patient may receive one or more of the lymphodepleting agents once per day during the lymphodepleting period. In one example, the human patient receives fludarabine at about 20-50 mg/m$^2$ (e.g., 30 mg/m$^2$) per day for 2-4 days (e.g., 3 days) and cyclophosphamide at about 500-750 mg/m$^2$ (e.g., 500 or 750 mg/m$^2$) per day for 2-4 days (e.g., 3 days). In specific examples, the human patient may receive fludarabine at about 30 mg/m$^2$ and cyclophosphamide at about 500 mg/m$^2$ per day for three days. In other specific examples, the human patient may receive fludarabine at about 30 mg/m$^2$ and cyclophosphamide at about 750 mg/m$^2$ per day for three days.

The human patient may then be administered any of the anti-CD19 CAR T cells such as CTX110 cells within a suitable period after the lymphodepleting therapy as disclosed herein. For example, a human patient may be subject to one or more lymphodepleting agent about 2-7 days (e.g., for example, 2, 3, 4, 5, 6, 7 days) before administration of the anti-CD19 CAR+ T cells (e.g., CTX110 cells). In some instances, a human patient is administered the anti-CD19 CAR+ T cells (e.g., CTX110 cells) within about 4-5 days after the lymphodepleting therapy.

Since the allogeneic anti-CD19 CAR-T cells such as CTX110 cells can be prepared in advance and may be stored at the treatment site, the lymphodepleting therapy as disclosed herein may be applied to a human patient having a B cell malignancy within a short time window (e.g., within 2 weeks) after the human patient is identified as suitable for the allogeneic anti-CD19 CAR-T cell therapy disclosed herein. For example, the first dose of the lymphodepleting therapy (e.g., fludarabine at about 30 mg/m$^2$ and cyclophosphamide at about 500 mg/m$^2$ or 750 mg/m$^2$) may be administered to the human patient within two weeks (e.g., within 10 days, within 9 days, within 8 days, within 7 days, within 6 days, within 5 days, within 4 days, within 3 days, within two days, or less) after the human patient is identified as suitable for the allogeneic anti-CD19 CAR-T cell therapy. In some examples, the lymphodepleting therapy may be performed to the human patient within 24-72 hours (e.g., within 24 hours) after the human patient is identified as suitable for the treatment. The patient can then be administered the CAR-T cells within 2-7 days (e.g., for example, 2, 3, 4, 5, 6, or 7 days) after the lymphodepleting treatment. This allows for timely treatment of the human patient with the allogeneic anti-CD19 CAR-T cells disclosed herein such as CTX110 cells after disease diagnosis and/or patient identification without delay (e.g., delay due to preparation of the therapeutic cells). In certain instances, a patient may receive the treatment during inpatient hospital care. In certain instances, a patient may receive the treatment in outpatient care.

Prior to any of the lymphodepletion steps, a human patient may be screened for one or more features to determine whether the patient is eligible for lymphodepletion treatment. For example, prior to lymphodepletion, a human patient eligible for lymphodepletion treatment does not show one or more of the following features: (a) significant worsening of clinical status, (b) requirement for supplemental oxygen to maintain a saturation level of greater than 90%, (c) uncontrolled cardiac arrhythmia, (d) hypotension requiring vasopressor support, (e) active infection, and (f) grade ≥2 acute neurological toxicity.

Following lymphodepletion, a human patient may be screened for one or more features to determine whether the patient is eligible for treatment with anti-CD19 CAR T cells such as the CTX110 cells. For example, prior to anti-CD19 CAR T cell treatment and after lymphodepletion treatment, a human patient eligible for anti-CD19 CAR T cells treatment does not show one or more of the following features: (a) active uncontrolled infection, (b) worsening of clinical status compared to the clinical status prior to lymphodepletion treatment, and (c) grade ≥2 acute neurological toxicity.

(iii) Administration of Anti-CD19 CAR T Cells

Administering anti-CD19 CAR T cells may include placement (e.g., transplantation) of a genetically engineered T cell population as disclosed herein (e.g., the CTX110 cells) into a human patient as also disclosed herein by a method or route that results in at least partial localization of the genetically engineered T cell population at a desired site, such as a tumor site, such that a desired effect(s) can be produced. The genetically engineered T cell population can be administered by any appropriate route that results in delivery to a desired location in the subject where at least a portion of the implanted cells or components of the cells remain viable. The period of viability of the cells after administration to a subject can be as short as a few hours, e.g., twenty-four hours, to a few days, to several weeks or months, to as long as several years, or even the life time of the subject, i.e., long-term engraftment. In certain instances, a patient may receive the genetically engineered T cell population (e.g., CTX110 cells) during inpatient hospital care. In certain instances, a patient may receive genetically engineered T cell population (e.g., CTX110 cells) in outpatient care.

For example, in some aspects described herein, an effective amount of the genetically engineered T cell population can be administered via a systemic route of administration, such as an intraperitoneal or intravenous route.

In some embodiments, the genetically engineered T cell population is administered systemically, which refers to the administration of a population of cells other than directly into a target site, tissue, or organ, such that it enters, instead, the subject's circulatory system and, thus, is subject to metabolism and other like processes. Suitable modes of administration include injection, infusion, instillation, or ingestion. Injection includes, without limitation, intravenous, intramuscular, intra-arterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion. In some embodiments, the route is intravenous.

An effective amount refers to the amount of a genetically engineered T cell population needed to prevent or alleviate at least one or more signs or symptoms of a medical condition (e.g., a B cell malignancy), and relates to a sufficient amount of a genetically engineered T cell population to provide the desired effect, e.g., to treat a subject having a medical condition. An effective amount also includes an amount sufficient to prevent or delay the development of a symptom of the disease, alter the course of a symptom of the disease (for example but not limited to, slow the progression of a symptom of the disease), or reverse a symptom of the disease. It is understood that for any given case, an appropriate effective amount can be determined by one of ordinary skill in the art using routine experimentation.

An effective amount of a genetically engineered T cell population may comprise about $1\times10^7$ CAR+ cells to about $1\times10^9$ CAR+ cells, e.g., about $1\times10^7$ cells to about $1\times10^9$ cells that express a CAR that binds CD19 (CAR+ cells). In some embodiments, an effective amount of a genetically engineered T cell population may comprise at least $1\times10^7$ CAR+ CTX110 cells, at least $3\times10^7$ CAR+ CTX110 cells, at least $1\times10^8$ CAR+ CTX110 cells, at least $3\times10^8$ CAR+ CTX110 cells, or at least $1\times10^9$ CAR+ CTX110 cells. In some embodiments, an effective amount of a genetically engineered T cell population may comprise a dose of the genetically engineered T cell population, e.g., a dose comprising about $1 \times 10^7$ CTX110 cells to about $1 \times 10^9$ CTX110 cells.

The efficacy of anti-CD19 CAR T cell therapy described herein can be determined by the skilled clinician. An anti-CD19 CAR T cell therapy (e.g., involving CTX110 cells) is considered "effective", if any one or all of the signs or symptoms of, as but one example, levels of CD19 are altered in a beneficial manner (e.g., decreased by at least 10%), or other clinically accepted symptoms or markers of a B cell malignancy are improved or ameliorated. Efficacy can also be measured by failure of a subject to worsen as assessed by hospitalization or need for medical interventions (e.g., progression of the B cell malignancy is halted or at least slowed). Methods of measuring these indicators are known to those of skill in the art and/or described herein. Treatment includes any treatment of a B cell malignancy in a human patient and includes: (1) inhibiting the disease, e.g., arresting, or slowing the progression of symptoms; or (2) relieving the disease, e.g., causing regression of symptoms; and (3) preventing or reducing the likelihood of the development of symptoms.

Following each dosing of anti-CD110 CAR T cells, a human patient may be monitored for acute toxicities such as tumor lysis syndrome (TLS), cytokine release syndrome (CRS), immune effector cell-associated neurotoxicity syndrome (ICANS), B cell aplasia, hemophagocytic lymphohistiocytosis (HLH), cytopenia, graft-versus-host disease (GvHD), hypertension, renal insufficiency, or a combination thereof.

When a human patient exhibits one or more symptoms of acute toxicity, the human patient may be subjected to toxicity management. Treatments for patients exhibiting one or more symptoms of acute toxicity are known in the art. For example, a human patient exhibiting a symptom of CRS (e.g., cardiac, respiratory, and/or neurological abnormalities) may be administered an anti-cytokine therapy. In addition, a human patient that does not exhibit a symptom of CRS may be administered an anti-cytokine therapy to promote proliferation of anti-CTX110 CAR T cells.

Alternatively, or in addition to, when a human patient exhibits one or more symptoms of acute toxicity, treatment of the human patient may be terminated. Patient treatment may also be terminated if the patient exhibits one or more signs of an adverse event (AE), e.g., the patient has an abnormal laboratory finding and/or the patient shows signs of disease progression.

The allogeneic anti-CD19 CAR T cell therapy (e.g., involving the CTX110 cells) described herein may also be used in combination therapies. For example, anti-CD19 CAR T cells treatment methods described herein may be co-used with other therapeutic agents, for treating a B cell malignancy, or for enhancing efficacy of the genetically engineered T cell population and/or reducing side effects of the genetically engineered T cell population.

IV. Kit for Allogeneic CAR-T Cell Therapy of B Cell Malignancies

The present disclosure also provides kits for use of a population of anti-CD19 CAR T cells such as CTX110 cells as described herein in methods for treating a B cell malignancy. Such kits may include one or more containers comprising a first pharmaceutical composition that comprises one or more lymphodepleting agents, and a second pharmaceutical composition that comprises any nucleic acid or population of genetically engineered T cells (e.g., those described herein), and a pharmaceutically acceptable carrier. Kits comprising the genetically engineered CAR-T cells as disclosed herein, such at the CTX110 cells, may be stored and inventoried at the site of care, allowing for rapid treatment of human patients following diagnosis.

In some embodiments, the kit can comprise instructions for use in any of the methods described herein. The included instructions can comprise a description of administration of the first and/or second pharmaceutical compositions to a subject to achieve the intended activity in a human patient. The kit may further comprise a description of selecting a human patient suitable for treatment based on identifying whether the human patient is in need of the treatment. In some embodiments, the instructions comprise a description of administering the first and second pharmaceutical compositions to a human patient who is in need of the treatment.

The instructions relating to the use of a population of anti-CD19 CAR T cells such as CTX110 T cells described herein generally include information as to dosage, dosing schedule, and route of administration for the intended treatment. The containers may be unit doses, bulk packages (e.g., multi-dose packages) or sub-unit doses. Instructions supplied in the kits of the disclosure are typically written instructions on a label or package insert. The label or package insert indicates that the population of genetically engineered T cells is used for treating, delaying the onset, and/or alleviating a T cell or B cell malignancy in a subject.

The kits provided herein are in suitable packaging. Suitable packaging includes, but is not limited to, vials, bottles, jars, flexible packaging, and the like. Also contemplated are packages for use in combination with a specific device, such as an inhaler, nasal administration device, or an infusion device. A kit may have a sterile access port (for example, the container may be an intravenous solution bag or a vial having a stopper pierceable by a hypodermic injection needle). The container may also have a sterile access port. At least one active agent in the pharmaceutical composition is a population of the anti-CD19 CAR-T cells such as the CTX110 T cells as disclosed herein.

Kits optionally may provide additional components such as buffers and interpretive information. Normally, the kit comprises a container and a label or package insert(s) on or associated with the container. In some embodiment, the disclosure provides articles of manufacture comprising contents of the kits described above.

General Techniques

The practice of the present disclosure will employ, unless otherwise indicated, conventional techniques of molecular biology (including recombinant techniques), microbiology, cell biology, biochemistry, and immunology, which are within the skill of the art. Such techniques are explained fully in the literature, such as *Molecular Cloning: A Laboratory Manual*, second edition (Sambrook, et al., 1989) Cold Spring Harbor Press; *Oligonucleotide Synthesis* (M. J. Gait, ed. 1984); *Methods in Molecular Biology*, Humana Press; *Cell Biology: A Laboratory Notebook* (J. E. Cellis, ed., 1989) Academic Press; Animal Cell Culture (R. I. Freshney, ed. 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds. 1993-8) J. Wiley and Sons; Methods in Enzymology (Academic Press, Inc.); Handbook of Experimental Immunology (D. M. Weir and C. C. Blackwell, eds.): Gene Transfer Vectors for Mammalian Cells (J. M. Miller and M. P. Calos, eds., 1987); Current Protocols in Molecular Biology (F. M. Ausubel, et al. eds. 1987); PCR: The Polymerase Chain Reaction, (Mullis, et al., eds. 1994);

Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: a practice approach (D. Catty., ed., IRL Press, 1988-1989); Monoclonal antibodies: a practical approach (P. Shepherd and C. Dean, eds., Oxford University Press, 2000); Using antibodies: a laboratory manual (E. Harlow and D. Lane (Cold Spring Harbor Laboratory Press, 1999); The Antibodies (M. Zanetti and J. D. Capra, eds. Harwood Academic Publishers, 1995); *DNA Cloning: A practical Approach*, Volumes I and II (D. N. Glover ed. 1985); *Nucleic Acid Hybridization* (B. D. Hames & S. J. Higgins eds. (1985; *Transcription and Translation* (B. D. Hames & S. J. Higgins, eds. (1984; *Animal Cell Culture* (R. I. Freshney, ed. (1986; *Immobilized Cells and Enzymes* (IRL Press, (1986; and B. Perbal, *A practical Guide To Molecular Cloning* (1984); F. M. Ausubel et al. (eds.).

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

Example 1: Preparation of CD19 Targeting Allogeneic CAR-T Cells

Allogeneic T cells expressing a chimeric antigen receptor (CAR) specific for CD19 were prepared from healthy donor peripheral blood mononuclear cells as described in US Publication No. US 2018-0325955, incorporated herein by reference. Briefly, primary human T cells were first electroporated with Cas9 or Cas9:sgRNA ribonucleoprotein (RNP) complexes targeting TRAC (AGAGCAACAGTGCTGTGGCC (SEQ ID NO: 26)) and B2M (GCTACTCTCTCTTTCTGGCC (SEQ ID NO: 27)). The DNA double stranded break at the TRAC locus was repaired by homology directed repair with an AAV6-delivered DNA template (SEQ ID NO: 56) containing right and left homology arms to the TRAC locus flanking a chimeric antigen receptor (CAR) cassette. The CAR comprised a single-chain variable fragment (scFv) derived from a murine antibody specific for CD19, a CD8 hinge region and transmembrane domain and a signaling domain comprising CD3z and CD28 signaling domains. The amino acid sequence of the CAR, and nucleotide sequence encoding the same, is set forth in SEQ ID NOs: 40 and 39, respectively. The gRNAs used in this Example comprise the following spacer sequences: TRAC gRNA spacer (AGAGCAACAGUGCUGUGGCC (SEQ ID NO: 19)); and B2M gRNA spacer (GCUACUCUCUCUUUCUGGCC (SEQ ID NO: 21)). A population of cells comprising TRAC$^-$/β2M$^-$/anti-CD19 CAR$^+$ T cells are referred to herein as "TC1 cells" or "CTX110 cells".

With CRISPR/Cas9 editing technology, high frequency knockout of the constant region of the TCRα gene (TRAC) with ~98% reduction of TCR surface expression in human primary T-cells from healthy donors, which aims to significantly impair graft-versus-host disease (GVHD), was achieved. High frequency knockout of the β-2-microglobulin (B2M) gene could also be obtained, which aims to increase persistence in patients, potentially leading to increased potency overall. TRAC/B2M double knockout frequencies have been obtained in ~80% of T cells without any subsequent antibody-based purification or enrichment. Human T cells expressing a CD19-specific CAR from within a disrupted TRAC locus, produced by homology-directed repair using an AAV6-delivered donor template, along with knockout of the B2M gene have been consistently produced at a high efficiency. This site-specific integration of the CAR protects against the potential outgrowth of CD3+CAR+ cells, further reducing the risk of GVHD, while also reducing the risk of insertional mutagenesis associated with retroviral or lentiviral delivery mechanisms. These engineered allogeneic CAR-T cells show CD19-dependent T-cell cytokine secretion and potent CD19-specific cancer cell lysis.

Figure 2:
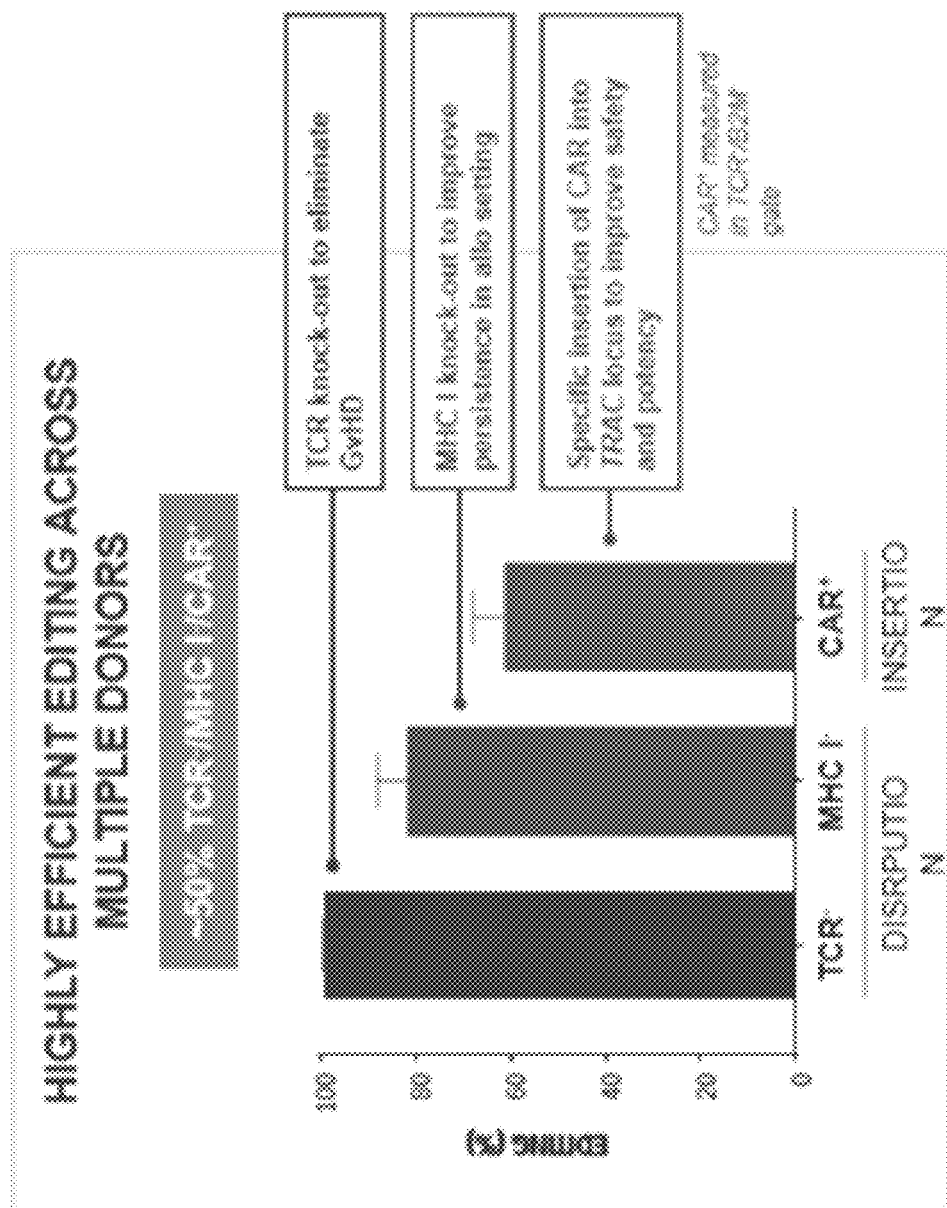
FIG. 2 is a graph depicting high editing rates achieved at the TRAC and B2M loci in TRAC−/B2M-CD19CAR+T cells (TC1). Surface expression of TCR and MHCI, which is the functional output of gene editing, was measured and plotted as editing percentage on the y-axis. High efficiency (e.g., greater than 50%) site-specific integration and expression of the CAR from the TRAC locus were detected. These data demonstrate greater than 50% efficiency for the generation of TRAC−/B2M−/anti-CD19CAR+T cells.

The production of allogeneic anti-CD19 CAR-T product (FIG. 1) exhibited efficiency editing (e.g., greater than 50% TRAC–/B2M–/anti-CD19 CAR+ T cells efficiency) (FIG. 2).

Example 2: Dose Escalation Study to Determine the Efficacy of CAR-T Cells in the Subcutaneous Raji Human Burkitt's Lymphoma Tumor Xenograft Model in NOG Mice The efficacy of CD19 targeting CAR-T cells against the subcutaneous Raji Human Burkitt's Lymphoma tumor xenograft model in NOG mice was evaluated using methods employed by Translational Drug Development, LLC (Scottsdale, Ariz.). In brief, 12, 5-8 week old female, CIEA NOG (NOD.Cg-Prkdc$^{scid}$ll2rg$^{tm1Sug}$/JicTac) mice were individually housed in ventilated microisolator cages, maintained under pathogen-free conditions, 5-7 days prior to the start of the study. On Day 1 mice received a subcutaneous inoculation of $5 \times 10^6$ Raji cells/mouse. The mice were further divided into 3 treatment groups as shown in Table 1. On Day 8 (7 days post inoculation with the Raji cells), treatment group 2 and group 3 received a single 200 µl intravenous dose of TRAC$^-$/B2M$^-$/anti-CD19 CAR-cells (TC1) according to Table 1.

TABLE 1

Treatment groups.

| Group | Raji Cells (s.c.) | TC1 Treatment (i.v.) | N |
|---|---|---|---|
| 1 | $5 \times 10^6$ cells/mouse | None | 4 |
| 2 | $5 \times 10^6$ cells/mouse | $5 \times 10^6$ cells/mouse | 4 |
| 3 | $5 \times 10^6$ cells/mouse | $1 \times 10^7$ cells/mouse | 4 |

Tumor volume and body weight was measured and individual mice were euthanized when tumor volume was ≥500 mm$^3$.

Figure 3:
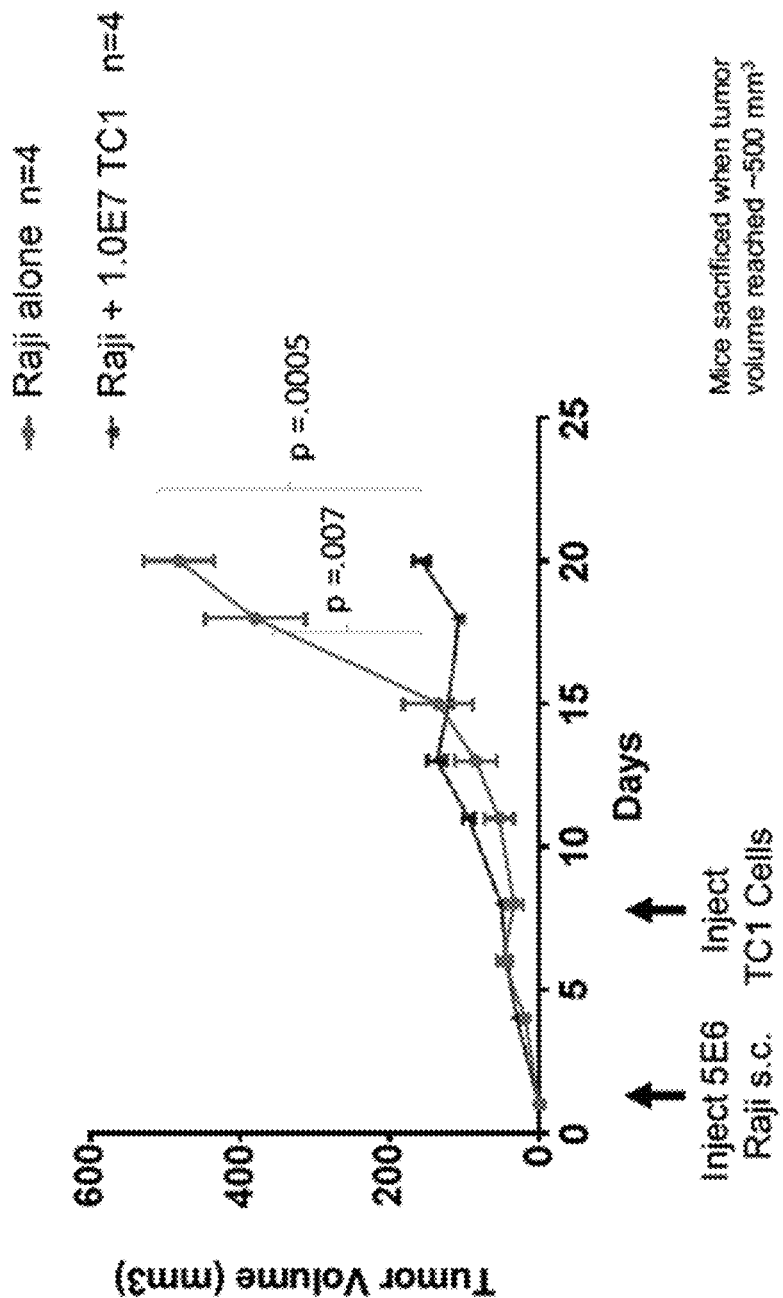
FIG. 3 is a graph depicting a statistically significant decrease in tumor volume (mm$^3$) (p=0.007) in NOG Raji mice following treatment with TRAC−/β2M−/CD19 CAR+ T cells (TC1).

By Day 18, the data show a statistically significant decrease in the tumor volume in response to TC1 cells as compared to untreated mice (FIG. 3). The effect on tumor volume was dose-dependent (Table 2); mice receiving higher doses of TC1 cells showed significantly reduced tumor volume when compared to mice receiving either a lower dose of TC1 cells or no treatment. An increase in survival was also observed in the treated group (Table 2).

TABLE 2

Tumor response and survival.

| Group | Tumor volume (Day 18) | Tumor volume (Day 20) | Survival (Days) | N |
|---|---|---|---|---|
| 1 | 379.6 ± 67.10 | 482 ± 47.37 | 20-22 | 4 |
| 2 | 214.0 ± 20.73 | 372.2 ± 78.21 | 25 | 4 |
| 3 | 107.5 ± 7.33* | 157.1 ± 10.62** | 27 (end of study) | 4 |

*p = 0.007 compared to control (Group 1)
**p = 0.0005 compared to control (Group 1)

Example 3: Assessment of CD19 Targeting CAR-T Cells Efficacy in Intravenous Disseminated Models in NOG Mice To further assess the efficacy of TRAC−/B2M−/anti-CD19 CAR+ cells (TC1), disseminated mouse models were utilized.

Intravenous Disseminated Raji Human Burkitt's Lymphoma Tumor Xenograft Model

The Intravenous Disseminated Model (Disseminated Model) using the Raji Human Burkitt's Lymphoma tumor cell line in NOG mice was used to further demonstrate the efficacy of TC1. Efficacy of TC1 was evaluated in the Disseminated Model using methods employed by Translations Drug Development, LLC (Scottsdale, Ariz.) and described herein. In brief, 24, 5-8 week old female CIEA NOG (NOD.Cg-Prkdc$^{scid}$Il2rg$^{tm1Sug}$/JicTac) mice were individually housed in ventilated microisolator cages, maintained under pathogen-free conditions, 5-7 days prior to the start of the study. At the start of the study, the mice were divided into 5 treatment groups as shown in Table 9. On Day 1 mice in Groups 2-5 received an intravenous injection of $0.5 \times 10^6$ Raji cells/mouse. The mice were inoculated intravenously to model disseminated disease. On Day 8 (7 days post injection with the Raji cells), treatment Groups 3-5 received a single 200 μl intravenous dose of TC1 cells (Table 3).

TABLE 3

Treatment groups.

| Group | Raji Cells (i.v.) | TC1 Treatment (i.v.) | N |
|---|---|---|---|
| 1 | None | None | 8 |
| 2 | $0.5 \times 10^6$ cells/mouse | None | 4 |
| 3 | $0.5 \times 10^6$ cells/mouse | $1 \times 10^6$ cells/mouse (~$0.5 \times 10^6$ CAR-T+ cells) | 4 |
| 4 | $0.5 \times 10^6$ cells/mouse | $2 \times 10^6$ cells/mouse (~$1.0 \times 10^6$ CAR-T+ cells) | 4 |
| 5 | $0.5 \times 10^6$ cells/mouse | $4 \times 10^6$ cells/mouse (~$2.0 \times 10^6$ CAR-T+ cells) | 4 |

During the course of the study mice were monitored daily and body weight was measured two times weekly. A significant endpoint was the time to peri-morbidity and the effect of T-cell engraftment was also assessed. The percentage of animal mortality and time to death were recorded for every group in the study. Mice were euthanized prior to reaching a moribund state. Mice may be defined as moribund and sacrificed if one or more of the following criteria were met:

Loss of body weight of 20% or greater sustained for a period of greater than 1 week;

Tumors that inhibit normal physiological function such as eating, drinking, mobility and ability to urinate and or defecate;

Prolonged, excessive diarrhea leading to excessive weight loss (>20%); or

Persistent wheezing and respiratory distress.

Animals were also considered moribund if there was prolonged or excessive pain or distress as defined by clinical observations such as: prostration, hunched posture, paralysis/paresis, distended abdomen, ulcerations, abscesses, seizures and/or hemorrhages.

Figure 4:
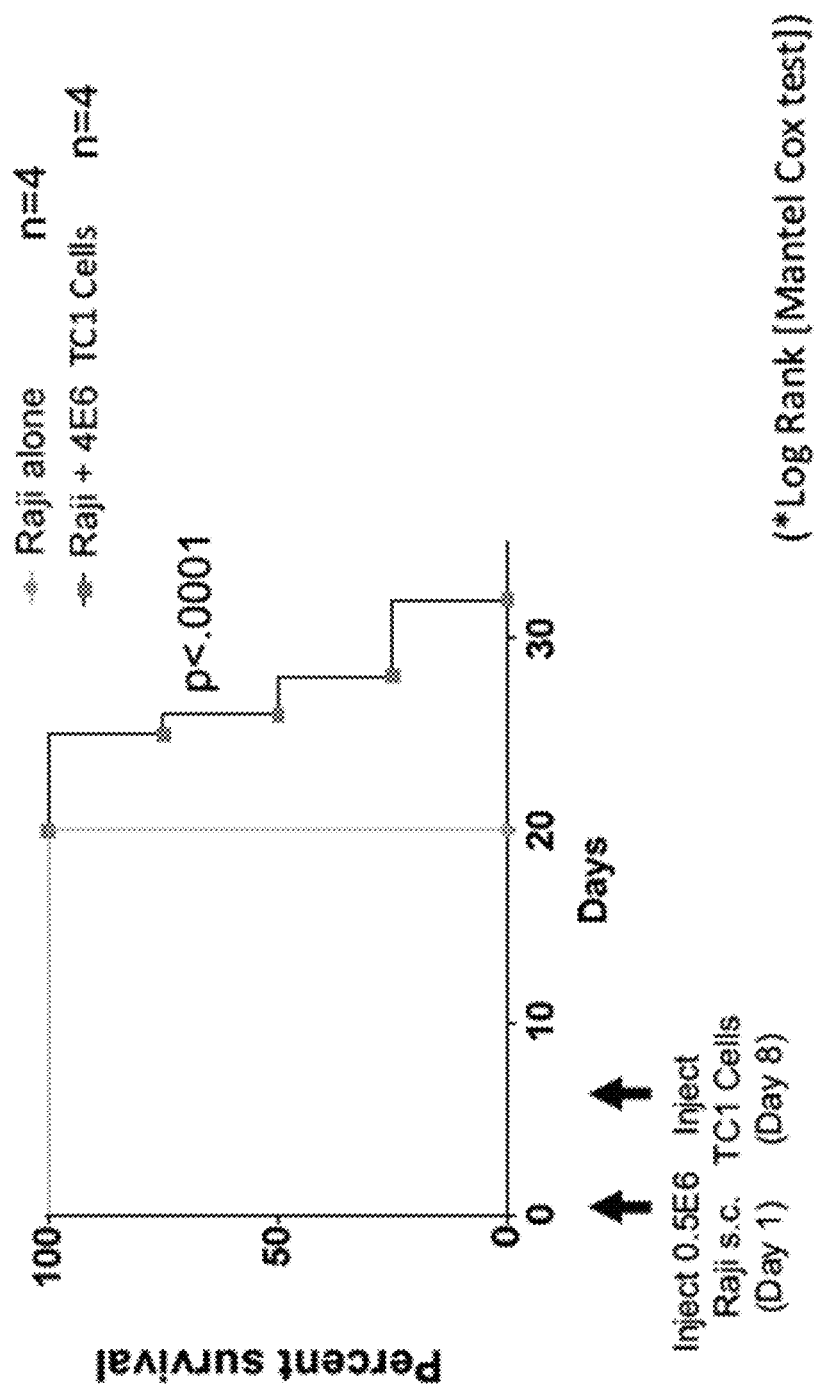
FIG. 4 is a survival curve graph demonstrating increased survival of NOG Raji mice treated with TC1 cells in comparison to NOG Raji mice receiving no treatment.

Similar to the subcutaneous xenograph model (Example 2), the Disseminated Model revealed a statistically significant survival advantage in mice treated with TRAC−/B2M−/anti-CD19 CAR+ cells (TC1) as shown in FIG. 4, p<0.0001.

The effect of TC1 treatment on survival in the disseminated model was also dose dependent (Table 4).

TABLE 4

Animal survival.

| Group | Raji Cells (i.v.) | TC1 Treatment (i.v.) | Max survival (days) | Median survival (days) |
|---|---|---|---|---|
| 1 | No | No | Max | Max |
| 2 | Yes | No | 20 | 20 |
| 3 | Yes | $1 \times 10^6$ cells/mouse | 21 | 21 |
| 4 | Yes | $2 \times 10^6$ cells/mouse | 25 | 25 |
| 5 | Yes | $4 \times 10^6$ cells/mouse | 32 | 26 |

A second experiment was run using the Intravenous Disseminated model described above.

On Day 1 mice in Groups 2-4 received an intravenous injection of $0.5 \times 10^6$ Raji cells/mouse. The mice were inoculated intravenously to model disseminated disease. On Day 4 (3 days post injection with the Raji cells), treatment Groups 2-4 received a single 200 μl intravenous dose of TC1 cells per Table 5.

TABLE 5

Treatment groups.

| Group | Raji Cells (i.v.) | TC1 Treatment (i.v.) | N |
|---|---|---|---|
| 1 | $0.5 \times 10^6$ cells/mouse | None | 6 |
| 2 | $0.5 \times 10^6$ cells/mouse | $0.6 \times 10^6$ CAR+ cells/mouse | 7 |
| 3 | $0.5 \times 10^6$ cells/mouse | $1.2 \times 10^6$ CAR+ cells/mouse | 5 |
| 4 | $0.5 \times 10^6$ cells/mouse | $2.4 \times 10^6$ CAR+ cells/mouse | 5 |

Figure 5:
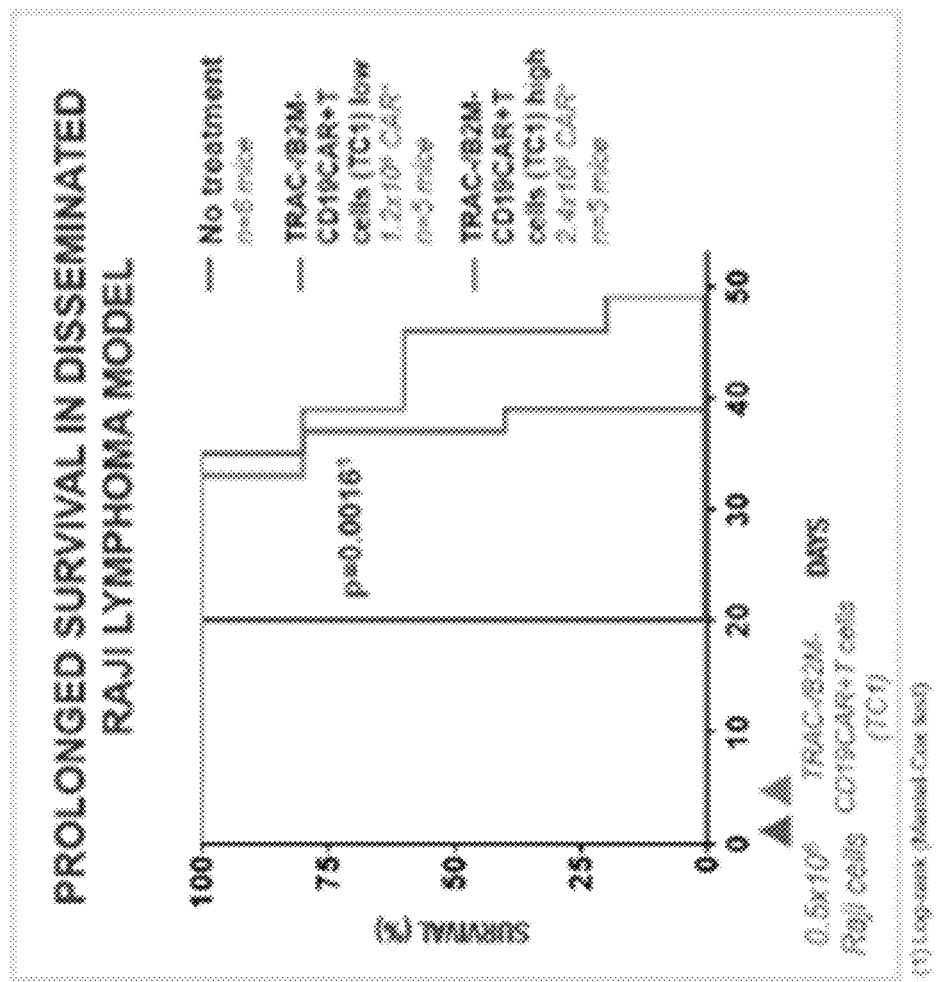
FIG. 5 is a survival curve graph demonstrating increased survival of NOG Raji mice treated with TC1 cells on day 4, in comparison to control mice receiving no treatment on day 1.

Again, the Disseminated Model revealed a statistically significant survival advantage in mice treated with TRAC−/B2M−/anti-CD19 CAR+ cells (TC1) as shown in FIG. 5, p=0.0016. The effect of TC1 treatment on survival in the disseminated model was also dose dependent (Table 6).

TABLE 6

Animal survival.

| Group | Raji Cells (i.v.) | TC1 Treatment (i.v.) | Max survival (days) | Median survival (days) | Significance |
|---|---|---|---|---|---|
| 1 | Yes | No | 20 | 20 | |
| 2 | Yes | $0.6 \times 10^6$ CAR+ cells/mouse | 35 | 27 | p = 0.005 |
| 3 | Yes | $1.2 \times 10^6$ CAR+ cells/mouse | 39 | 37 | p = 0.016 |
| 4 | Yes | $2.4 \times 10^6$ CAR+ cells/mouse | 49 | 46 | p = 0.016 |

Evaluation of Splenic response to TC1 Treatment

The spleen was collected from mice 2-3 weeks following Raji injection and the tissue was evaluated by flow cytometry for the persistence of TC1 cells and eradication of Raji cells in the spleen.

The spleen was transferred to 3 mL of 1×DPBS CMF in a C tube and dissociated using the MACS Octo Dissociator. The sample was transferred through a 100 micron screen into a 15 mL conical tube, centrifuged (1700 rpm, 5 minutes, ART with brake) and resuspended in 1 mL of 1×DPBS CMF for counting using the Guava PCA. Bone marrow was centrifuged and resuspended in 1 mL of 1×DPBS CMF for counting using the Guava PCA. Cells were resuspended at a concentration of $10 \times 10^6$ cells/mL in 1×DPBS CMF for flow cytometry staining.

Specimens (50 μL) were added to 1 mL 1× Pharm Lyse and incubated for 10-12 minutes at room temperature (RT). Samples were centrifuged and then washed once with 1×DPBS CMF. Samples were resuspended in 50 μL of 1×DPBS and incubated with Human and Mouse TruStain for 10-15 minutes at RT. The samples were washed once with 1 mL 1×DPBS CMF and resuspend in 50 μL of 1×DPBS CMF for staining. Surface antibodies were added and the cells incubated for 15-20 minutes in the dark at RT and then washed with 1 mL 1×DPBS CMF. Then samples were resuspended in 125 μL of 1×DPBS CMF for acquisition on the flow cytometer. Cells were stained with the following surface antibody panel:

TABLE 7

Antibody panel.

| FITC | PE | APC | C3 | APCCy7 | V421 | V510 |
|---|---|---|---|---|---|---|
| huCD3 (UCHT1) | huCD45 (HI30) | huCD19 (HIB19) | 7AAD | CD8 (SK1) | CD4 (RPA-T4) | mCD45 (30-F11) |

Cell populations were determined by electronic gating (P1=total leukocytes) on the basis of forward versus side scatter. Compensation to address spill over from one channel to another was performed upon initial instrument set up using Ultra Comp Beads from Thermo Fisher. The flow cytometer was set to collect 10,000 CD45+ events in each tube. Flow cytometric data acquisition was performed using the FACSCantoII™ flow cytometer. Data was acquired using BO FACSDiva™ software (version 6.1.3 or 8.0.1). Flow cytometry data analysis was in the form of Flow Cytograms, which are graphical representations generated to measure relative percentages for each cell type.

Figure 6B:
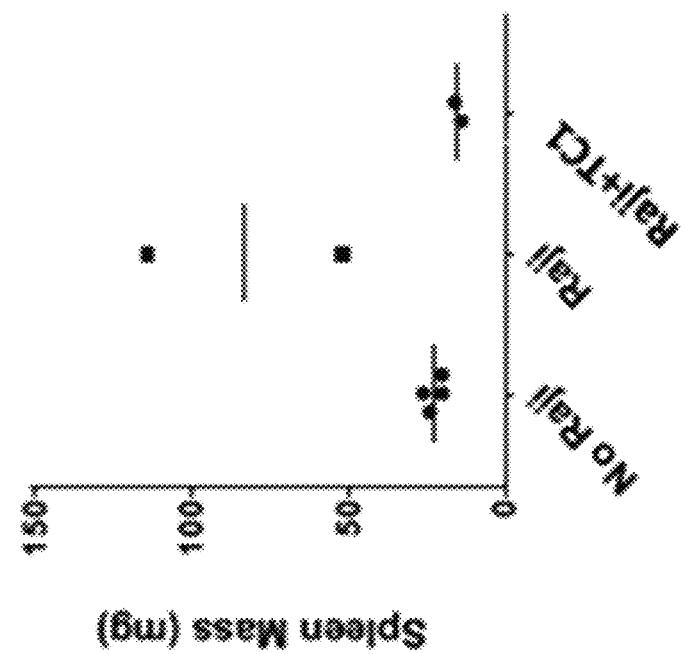
FIGS. 6A and 6B include diagrams showing persistence and anti-tumor activity of TC1 cells in mice. 6A: a series of flow cytometry plots demonstrating that TC1 cells persist in NOG Raji mice. 6B: a graph demonstrating that TC1 cells selectively eradicate splenic Raji cells in NOG Raji mice treated with TC1 in comparison to controls (NOG Raji mice with no treatment or NOG mice). The effect is depicted as a decreased splenic mass in NOG Raji mice treated with TC1 in comparison to controls.
Figure 6A:
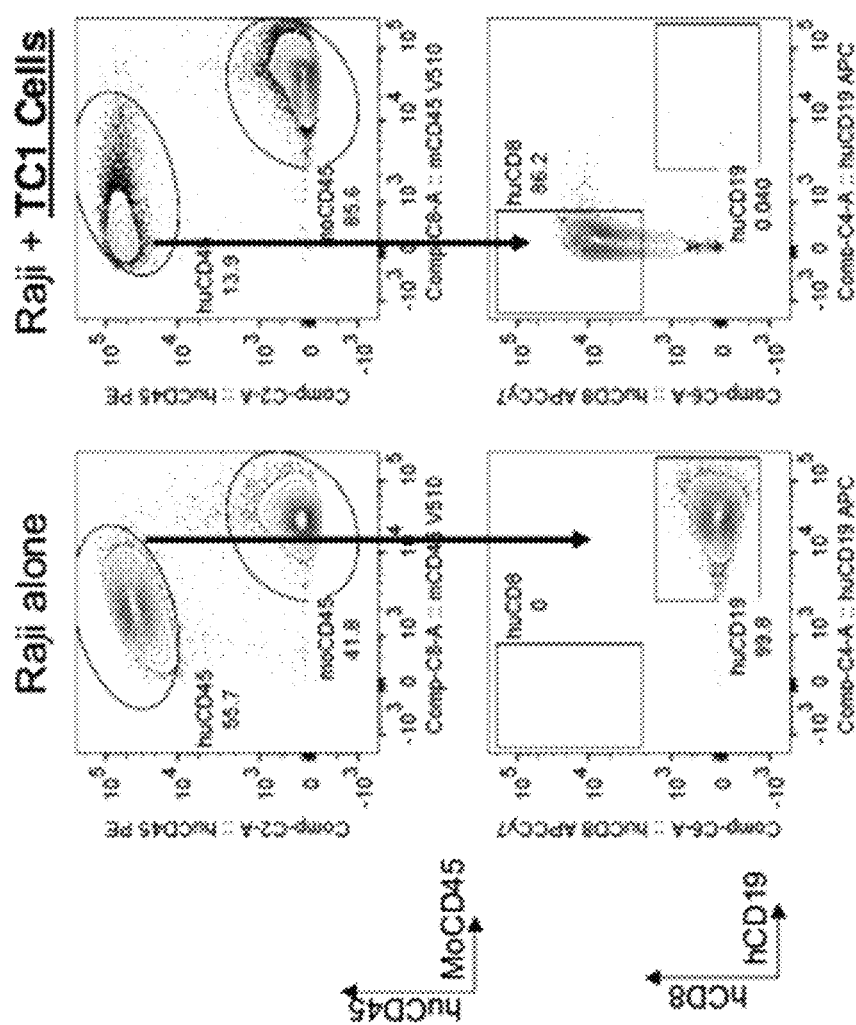
Figure 7:
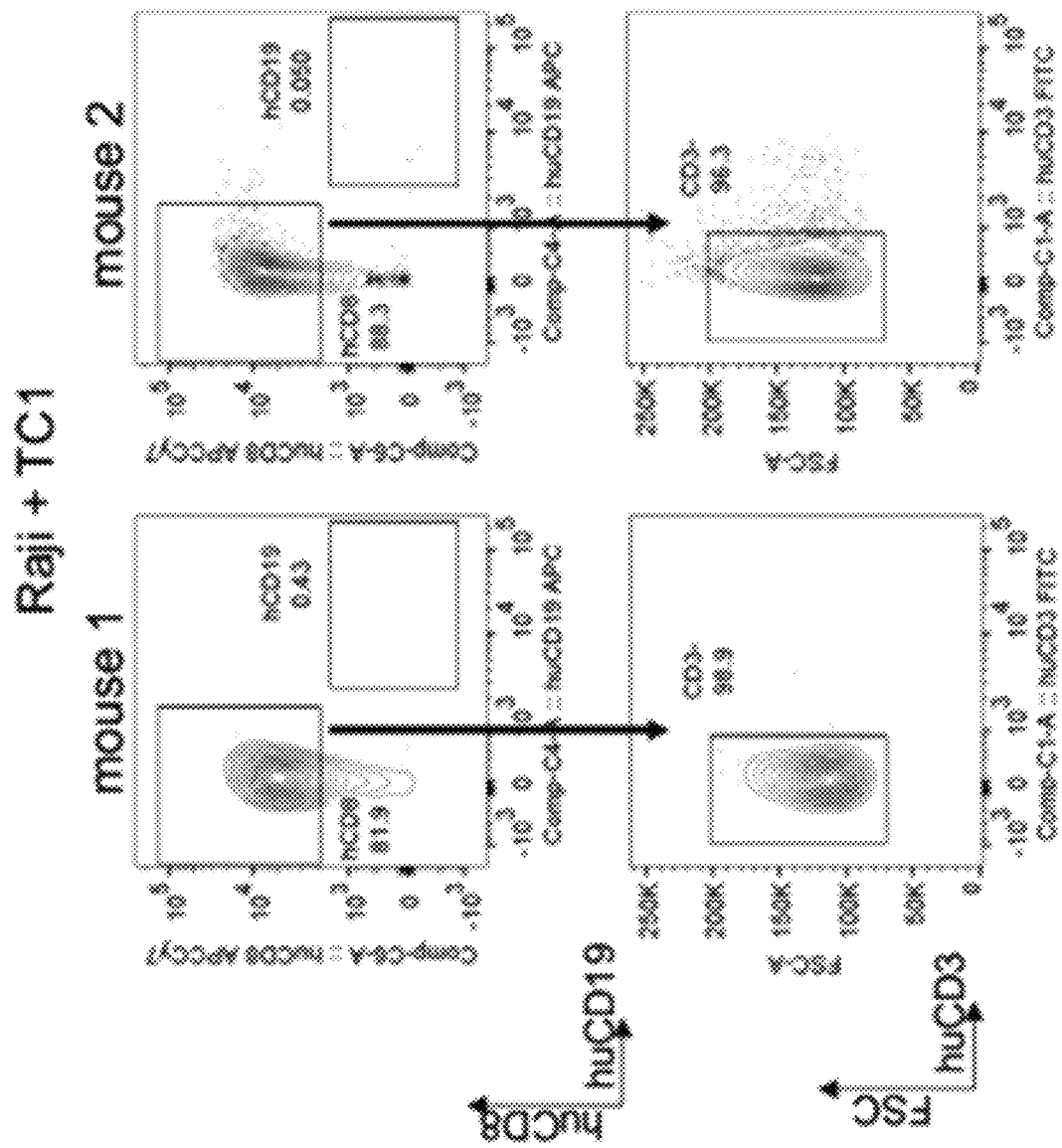
FIG. 7 is a series of flow cytometry plots demonstrating that persistent splenic TC1 cells are edited in two independent NOG Raji mice with TC1 treatment.

This example demonstrates that following TC1 cell treatment, the therapeutically beneficial TRAC$^-$/B2M$^-$/anti-CD19 CAR+ cells persist in the spleen and selectively eradicate Raji cells from the tissue (FIG. 6A). In addition, treatment with TC1 cells do not exhibit Raji induced increase in cell mass (FIG. 6A). Further, FIG. 7 shows that the remaining human cells in spleens of mice treated with TRAC$^-$/B2M$^-$/anti-CD19 CAR+ cells are CD8+. These CD8+ T cells are also CD3 negative proving that persistent T cells in this model remain TCR/CD3 negative and are thus edited.

Intravenous Disseminated Nalm-6 Human Acute Lymphoblastic Leukemia Tumor Xenograft Model The Intravenous Disseminated Model (Disseminated Model) using the Nalm-6 Human Acute Lymphoblastic Leukemia tumor cell line in NOG mice was used in to further demonstrate the efficacy of TC1. Efficacy of TC1 was evaluated in the Disseminated Model using methods employed by Translations Drug Development, LLC (Scottsdale, Ariz.) and described herein. In brief, 24, 5-8 week old female CIEA NOG (NOD.Cg-Prkdc$^{scid}$Il2rg$^{tm1Sug}$/JicTac) mice were individually housed in ventilated microisolator cages, maintained under pathogen-free conditions, 5-7 days prior to the start of the study. At the start of the study, the mice were divided into 5 treatment groups as shown in Table 14. On Day 1 mice in Groups 2-4 received an intravenous injection of 0.5×10$^6$ Nalm6 cells/mouse. The mice were inoculated intravenously to model disseminated disease. On Day 4 (3 days post injection with the Nalm6 cells), treatment Groups 2-4 received a single 200 μl intravenous dose of TC1 cells per Table 8.

TABLE 8

Treatment groups.

| Group | Nalm6 Cells (i.v.) | TC1 Treatment (i.v.) | N |
|---|---|---|---|
| 1 | 0.5 × 10$^6$ cells/mouse | None | 6 |
| 2 | 0.5 × 10$^6$ cells/mouse | 1 × 10$^6$ CAR$^+$ cells/mouse | 6 |
| J | 0.5 × 10$^6$ cells/mouse | 2 × 10$^6$ CAR$^+$ cells/mouse | 6 |
| 4 | 0.5 × 10$^6$ cells/mouse | 4 × 10$^6$ CAR$^+$ cells/mouse | 6 |

During the course of the study mice were monitored daily and body weight was measured two times weekly as described above.

Figure 8:
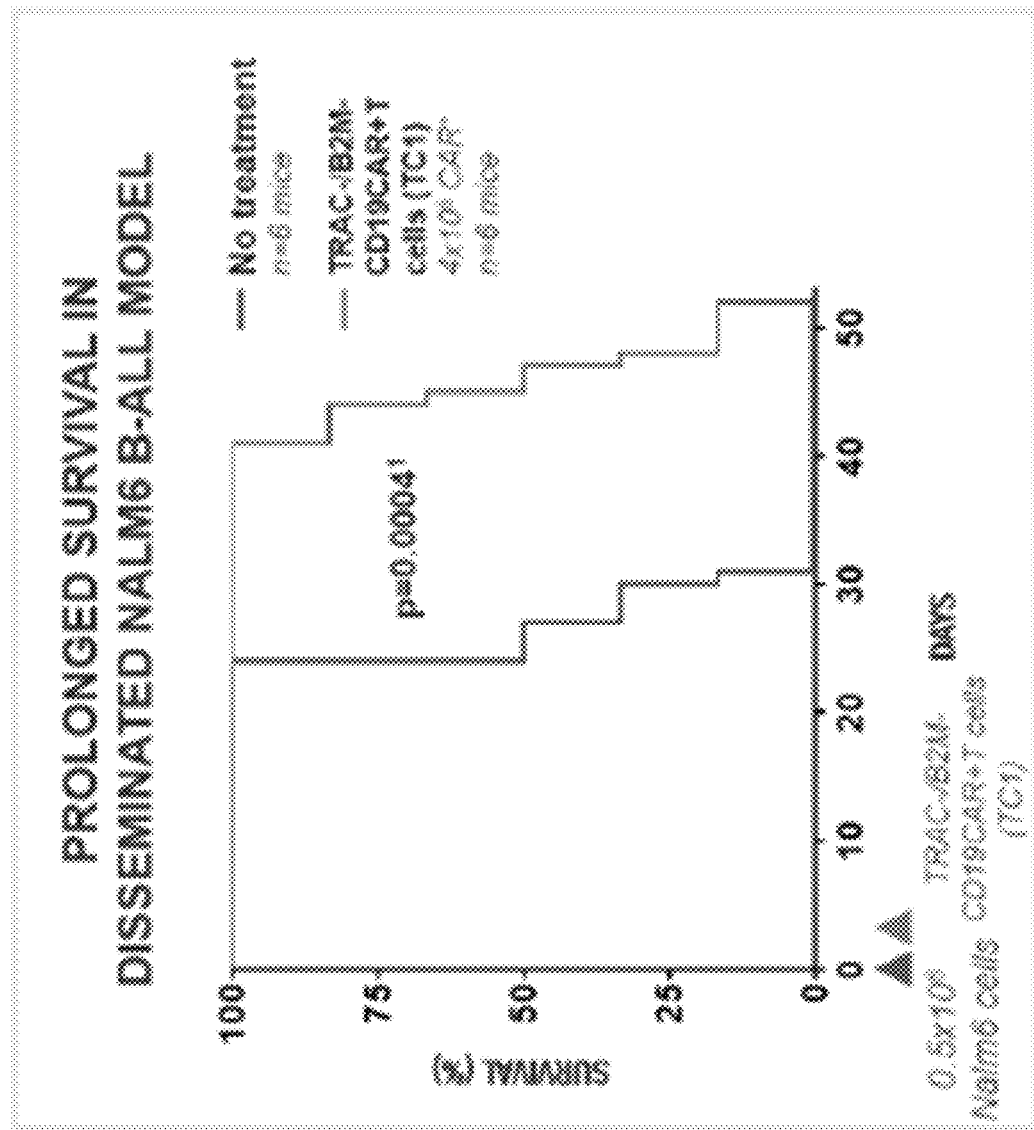
FIG. 8 is a Kaplan-Meier survival plot demonstrating increased survival of NOG Nalm6 mice treated with TC1 cells on day 4, in comparison to control mice receiving no treatment on day 1.

Similar to the Raji intravenous disseminated model (above), the Nalm6 Model also showed a statistically significant survival advantage in mice treated with TRAC$^-$/B2M$^-$/anti-CD19 CAR+ cells (TC1) as shown in FIG. 8, p=0.0004. The effect of TC1 treatment on survival in the Nalm6 disseminated model was also dose dependent (Table 9).

TABLE 9

Animal survival.

| Group | Nalm6 Cells (i.v.) | TC1 Treatment (i.v.) | Max survival (days) | Median Survival (days) | Significance |
|---|---|---|---|---|---|
| 1 | Yes | No | 31 | 25.5 | |
| 2 | Yes | $^1$ × 10$^6$ CAR$^+$ cells/mouse | 32 | 31 | p = 0.03 |
| 3 | Yes | 2 × 10$^6$ CAR$^+$ cells/mouse | 38 | 36 | p = 0.0004 |
| 4 | Yes | 4 × 10$^6$ CAR$^+$ cells/mouse | 52 | 46 | p = 0.0004 |

Example 4: Further Assessment of CD19 Targeting CAR-T Cells Efficacy in Intravenous Disseminated Models in NOG Mice The purpose of this study was to evaluate the anti-tumor activity of anti-CD19 CAR+ T cells at multiple dose levels against the Nalm6-Fluc-GFP acute lymphoblastic leukemia tumor cell line in NOG mice. The mice were inoculated intravenously to model disseminated disease. Significant endpoint was time to peri-morbidity. Bioluminescent imaging was performed to monitor progression of disseminated disease.

In brief, 6 week old female, CIEA NOG (NOD.Cg-Prkdc$^{scid}$Il2rg$^{tm1Sug}$/JicTac) mice were housed in ventilated microisolator cages, maintained under pathogen-free conditions, 5-7 days prior to the start of the study. On Day 1 mice received an intravenous inoculation of 5×10$^4$ Nalm6-Fluc-GFP (Nalm6-Fluc-Neo/eGFP—Puro; Imanis Life Sciences (Rochester, Minn.)) cells/mouse. Three (3) days post inoculation with Nalm6-Fluc-GFP cells, the mice were divided into treatment groups and dosed with T cell populations comprising TRAC$^-$/B2M$^-$/anti-CD19 CAR+ T cells, as indicated in Table 10. Region of Interest values (ROI) values were captured and reported. Body weight was measured twice daily and bioluminescence was measured twice weekly starting on Day 4 (3 Days Post inoculation of Nalm6-Fluc-GFP cells) through Day 67, once weekly starting Day 74 to study end. To measure bioluminescence mice were injected intraperitoneally with 200 μl of D-Luciferin 150 mg/kg. Kinetics images were taken at the beginning of the study and as needed throughout to determine optimal post D-Luciferin dose and exposure time to image the mice. Mice were imaged by capturing luminescence signal (open emission) using an AMI 1000 imaging unit with software version 1.2.0 (Spectral Instruments Imaging Inc.; Tucson, Ariz.).

TABLE 10

Treatment groups.

| Group | Anti-CD19 CAR T Cell | # of T Cells injected (iv) | Anti-CD19 CAR+ T cells | N |
|---|---|---|---|---|
| 1 | N/A | N/A | N/A | 5 |
| 2 | TRAC-/β2M-/anti-CD19 | $3 \times 10^6$ cells/mouse | $\sim 1.8 \times 10^6$ | 5 |
| 3 | TRAC-/β2M-/anti- CD19 | $6 \times 10^6$ cells/mouse | $\sim 3.6 \times 10^6$ | 5 |
| 4 | TRAC-/β2M-/anti- CD19 | $12 \times 10^6$ cells/mouse | $7.2 \times 10^6$ | 4 |

Individual mice were euthanized at peri-morbidity (clinical signs suggesting high tumor burden (e.g., lack of motility, hunch back, hypoactivity) or 20% or greater body weight loss sustained for a period of greater than 1-week). Mice were euthanized prior to reaching a moribund state. The study was ended on Day 99 when the final mouse was euthanized as a long-term survivor.

Figure 9:
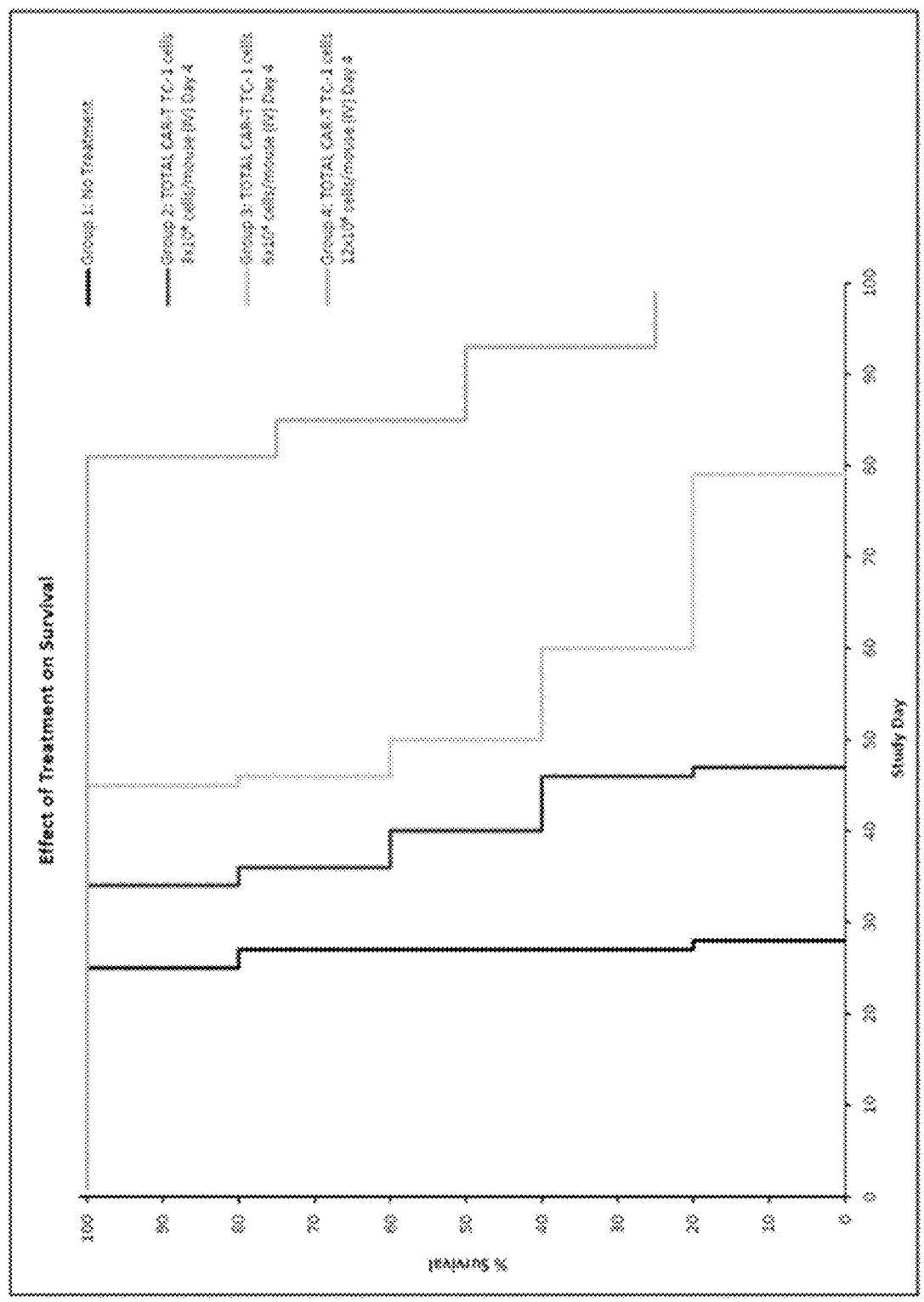
FIG. 9 is a Kaplan-Meier survival plot demonstrating an increase survival of mice bearing a disseminated Nalm6 B-cell acute lymphoblastic leukemia (B-ALL) after treatment with different concentrations of TC1, in comparison to control mice receiving no treatment.
Figure 10:
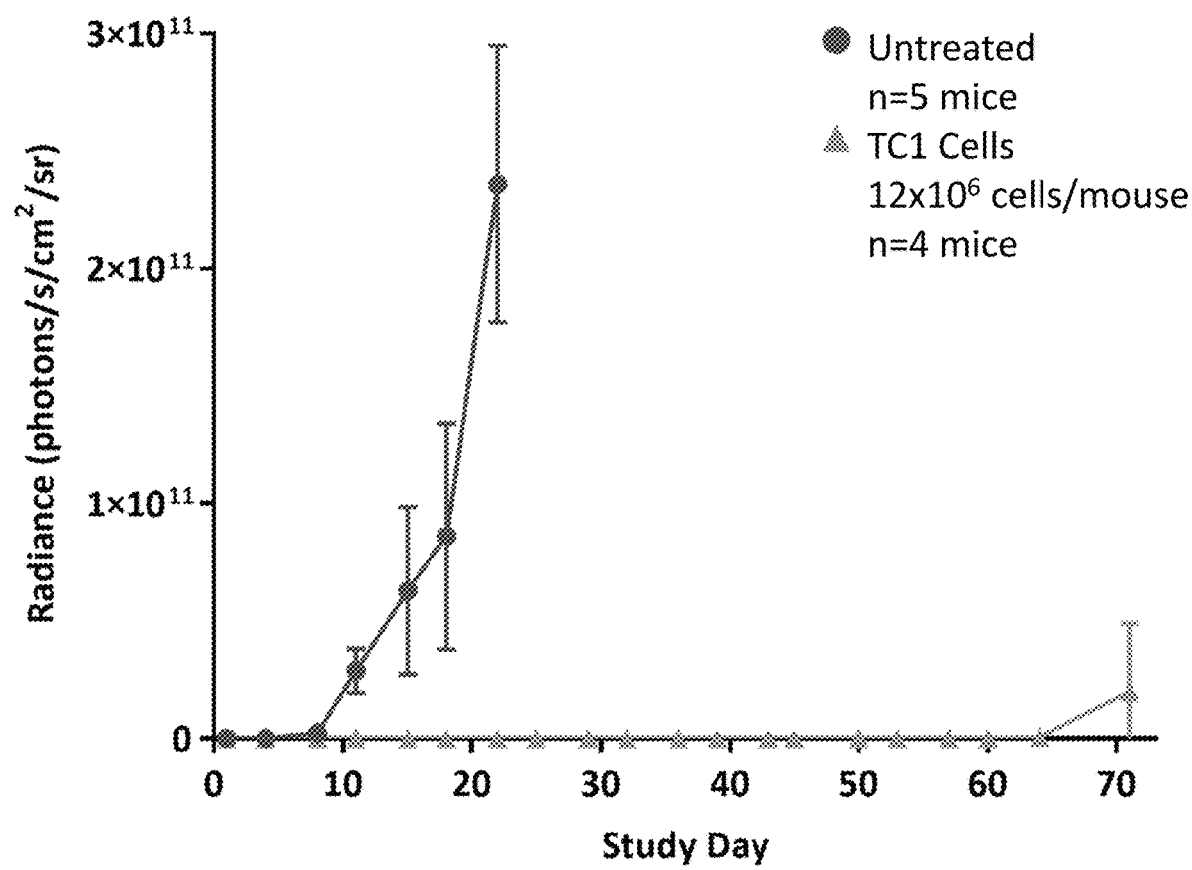
FIG. 10 is a graph depicting a statistically significant inhibition in tumor cell expansion in the disseminated Nalm6 B-cell acute lymphoblastic leukemia (B-ALL) tumor model following treatment with TC1 cells.

FIG. 9 shows prolonged survival of mice that received different doses of TC1 cells relative to untreated mice. FIG. 10 shows low to undetectable levels of bioluminescence in mice that received the highest dose of TC1 cells ($12 \times 10^6$ cells/mouse) and which resulted in the longest survival as shown in FIG. 9. At day 74 bioluminescence was detected in all 4 mice, indicative of tumor cell expansion in the treatment group.

Overall, these results show a single injection of TC1 cells can prolong survival of mice that were administered a lethal dose of Nalm6 B-ALL cells. This prolonged survival is dose dependent with a graded survival response observed between low, middle and high doses of TC1 cells.

Example 5: Analysis of Graft Versus Host Disease in Mice Administered Allogeneic CD19 Targeting CAR T Cells A study in mice was conducted to evaluate the potential for both unedited human T cells and TC1 cells to cause graft versus host disease (GvHD). After total body irradiation with 200 cGy, NOG female mice were administered a single intravenous slow bolus injection of unedited human T cells or TC1 cells. Animals were followed for up to 119 days after radiation only (Group 1) or radiation plus a single dose administration of PBMCs (Group 2), electroporated T cells (Group 3) or TC1 cells (Group 4). Cells were administered approximately 6 hours post radiation on Day 1. Table 11 summarizes the groups and study design.

TABLE 11

Treatment groups.

| Group Number | Test Article | Dose Level (cells/mouse) | Total Irradiation Dose | Number of Animals (Female) |
|---|---|---|---|---|
| 1 | Radiation Only | 0 | 200 cGy | 12 |
| 2 | Radiation + PBMCs | $6 \times 10^6$ | | 6 |
| 3 | Radiation + EP T cells | $3 \times 10^7$ | | 6 |
| 4 | Radiation + TC1 cells | $3 \times 10^7$ | | 6 |

The endpoints of the study were survival, kinetics of appearance of GvHD symptoms, and body weight measurements.

Figure 11:
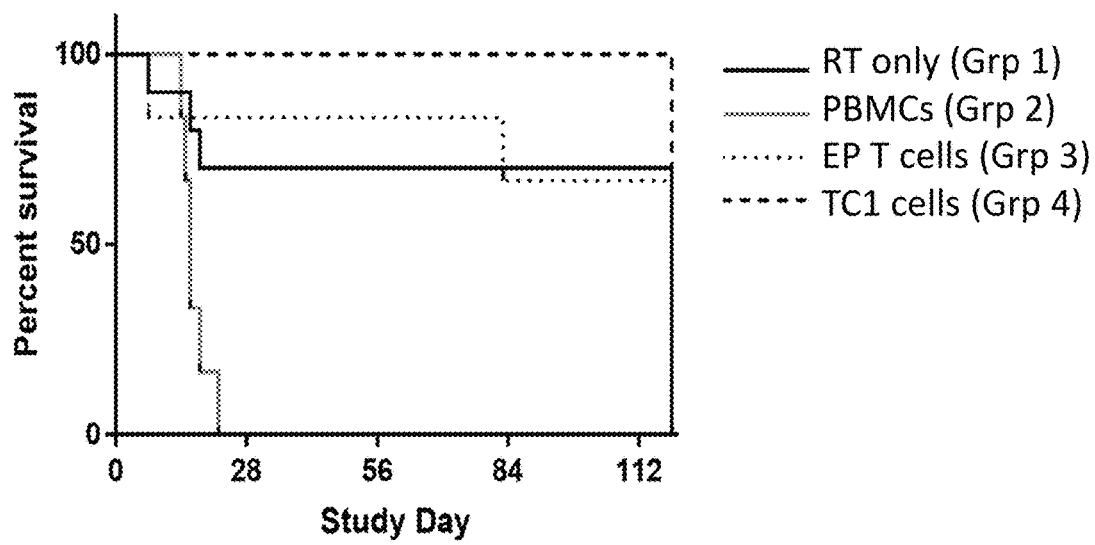
FIG. 11 is a Kaplan-Meier survival plot of healthy mice treated with TC1 cells or various control cells (PBMCs or electroporated (EP) T cells) after radiation, or mice that only received radiation ("RT only").
Figure 12:
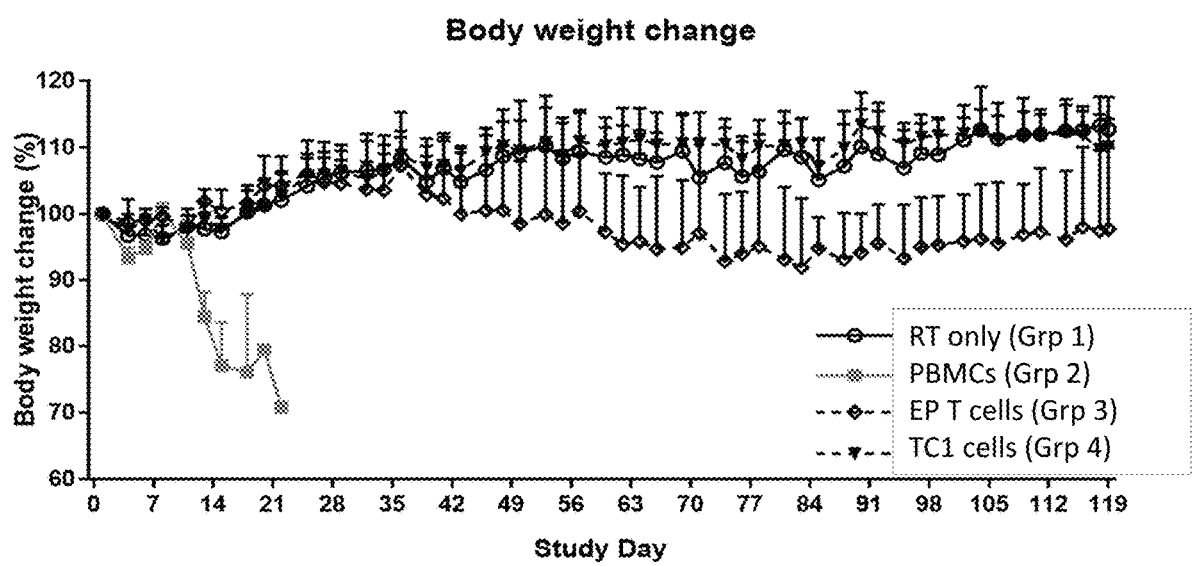
FIG. 12 is a graph showing percentage of body weight change of the mice treated in FIG. 18.

Mortality was observed in Group 1 (3 of 12 animals), Group 2 (6 of 6 animals) and Group 3 (2 of 6 animals) during the first 30 days post-treatment (FIG. 11). All animals in Group 4 (TC1 cells) survived until scheduled necropsy (FIG. 11). Moribund animals in Groups 1, 2 and 3 experienced weight loss and/or clinical observations consistent with the development of GvHD (slight to severe cold to touch, slight to moderate emaciation, slight to marked hunched posture, severe weight loss, mild to severe alopecia, severe hypoactivity, moderate labored respiration, and marked tachypnea). Animals in Groups 1 and 4, and non-moribund animals in Group 3, experienced mild weight loss following radiation which improved over the course of the study (FIG. 12). No notable clinical observations were recorded.

This study demonstrated that unedited human PBMCs induce fatal GvHD in irradiated NOG mice in all animals (Group 2), with onset 2 to 3 weeks after administration of cells. In contrast, no mice that received TC1 cells (Group 4) developed GvHD during the study (119 days), despite the higher number of cells that were administered to these animals ($3 \times 10^7$ TC1 cells per mouse compared to $6 \times 10^6$ PBMCs per mouse). The irradiation procedure induced transient weight loss in all groups and recovered in all groups that did not receive unedited PBMCs.

A second study was conducted to further evaluate the potential for both unedited human T cells and TC1 cells to cause GvHD. Specifically, NOD/SCID/IL2Rγnull (NSG) female mice were administered a single intravenous slow bolus injection of unedited human T cells or TC1 cells after a total body irradiation (total irradiation dose of 200 cGy, 160 cGy/min; targeted $LDR_{0/140}R$). The endpoints of this study were survival, kinetics of appearance of symptoms of GvHD and body weight measurements. Histopathology was also performed on all collected tissues. Exposure was assessed in mouse blood and tissues by flow cytometry and immunohistochemistry (IHC), where appropriate.

The cells were administered as a single dose via intravenous slow bolus as described in Table 12.

TABLE 12

Study Design.

| Group Number | Test Article | Dose (Cells/ Mouse) | Concentration (Cells/mL) | Total Irradiation Dose | Number of Animals M | Number of Animals F |
|---|---|---|---|---|---|---|
| 1 | Vehicle - no RT[a] | 0 | 0 | 0 cGy | 5 | 5 |
| 2 | Vehicle - RT[a] | 0 | 0 | 200 cGy | 15 | 15 |
| 3 | Unedited T cells | $1 \times 10^7$ | $4 \times 10^7$ | | 15 | 15 |
| 4 | TC1 - low dose | $2 \times 10^7$ | $8 \times 10^7$ | | 15 | 15 |
| 5 | TC1 - high dose | $4 \times 10^7$ | $16 \times 10^7$ | | 15 | 15 |

[a]Group 1 animals were not irradiated and were not dosed with cells (animals were administered with vehicle, PBS 1X). Group 2 animals were irradiated but were not dosed with cells (animals were administered with vehicle, phosphate-buffered saline [PBS]).

Animals were randomized into treatment groups by body weight using a validated preclinical software system (Provantis). Due to the large size of this study, dosing and necropsy activities were staggered over nine days. To minimize bias, animals from the control and TC1 groups (Groups 4 and 5) were dosed and necropsied on the same day. Necropsy occurred on Study Day 85 for all groups.

Figure 13:
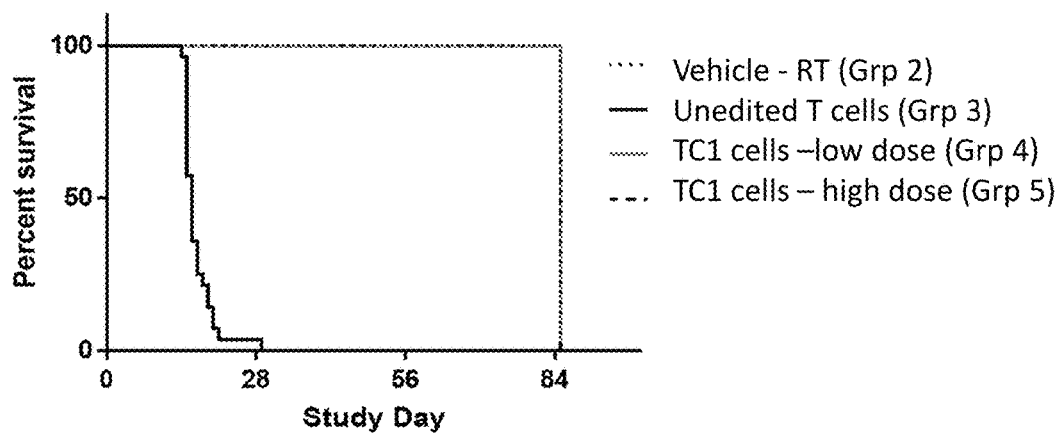
FIG. 13 is a Kaplan-Meier survival plot of healthy mice treated with a low dose ($2\times10^7$) or high dose ($4\times10^7$) of TC1 cells, or unedited T cells after radiation, or mice that only received radiation ("Vehicle-RT").

Mortality was observed for all animals that received unedited human T cells (Group 3), with onset at Day 14 (FIG. 13). All mice that received unedited human T cells (Group 3), were either found dead or sent to unscheduled euthanasia by Day 29. Clinical signs in these animals were consistent with the development of GvHD and included dull fur, slight to severe decreased activity, hunched back posture, slight to moderate thinness, and increased respiratory rate. Marked changes in hematology parameters were observed at euthanasia in mice that received unedited human T cells (Group 3), including decreases in red blood cells, hemoglobin, platelets, white blood cells and reticulocyte counts. Minimal to moderate inflammation was observed in the liver, lung, kidney, spleen, and thymus of Group 3 animals. Necrosis often accompanied inflammation in these tissues. These findings were consistent with the development of GvHD. Additionally, mild to severe hypocellularity in the femoral and sternal bone marrow was also present in the majority of Group 3 animals, which was likely attributable to the effects of total body irradiation. This was likely only observed in this group due to the early necropsy dates (2-4 weeks post-radiation), compared to 12 weeks for all other groups. Consistent with the presence of GvHD, immunohistochemical analysis of Group 3 animals revealed the presence of human CD45P⁺P cells in all tissues examined (kidney, liver, spleen, lung, skin, and the digestive tract). All animals in the other Groups survived until the scheduled necropsy.

Figure 14:
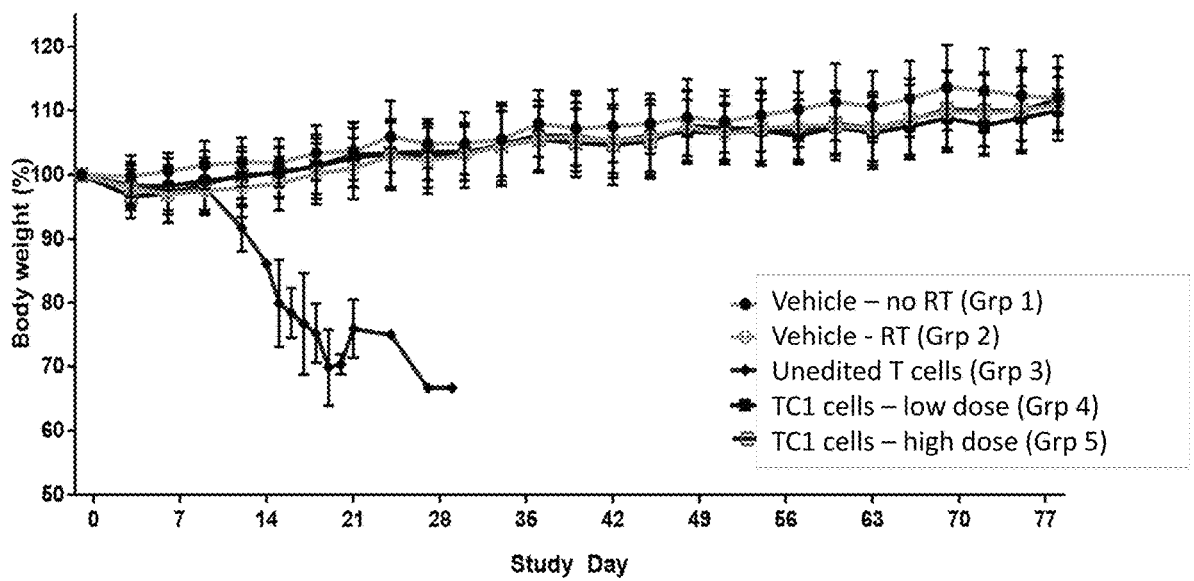
FIG. 14 is a graph showing percentage of body weight change of the mice treated in FIG. 20, in addition to mice that were not irradiated and not dosed with cells ("Vehicle—no RT").

Further, no significant weight loss was observed in Groups 1, 2, 4, or 5 (FIG. 14). No notable clinical observations that were consistent with GvHD, characterized by observations of at least two symptoms considered likely to denote GvHD, were recorded in these groups. Several animals from Groups 4 and 5 exhibited symptoms such as dull fur, slight to moderate decreased activity, and/or slight thinness throughout the study. Although these symptoms are often associated with GvHD, they did not appear to be TC1-related as they were infrequently observed, transient and of short duration, and were also seen in some irradiated control animals (Group 2).

Overall the results from these two studies confirmed TC1 cells do not induce graft versus host disease.

Example 6: Preparation and Characterization of Developmental Lots of Allogeneic CD19 Targeting CAR T Cells TC1 cells for the purposes of the clinical study were prepared from healthy donor peripheral blood mononuclear cells obtained via a standard leukopheresis procedure. The mononuclear cells were enriched for T cells and activated with anti-CD3/CD28 antibody-coated beads, then electroporated with CRISPR-Cas9 ribonucleoprotein complexes and transduced with a CAR gene-containing recombinant adeno-associated virus (AAV) vector. The modified T cells were expanded in cell culture, purified, formulated into a suspension, and cryopreserved.

Figure 15:
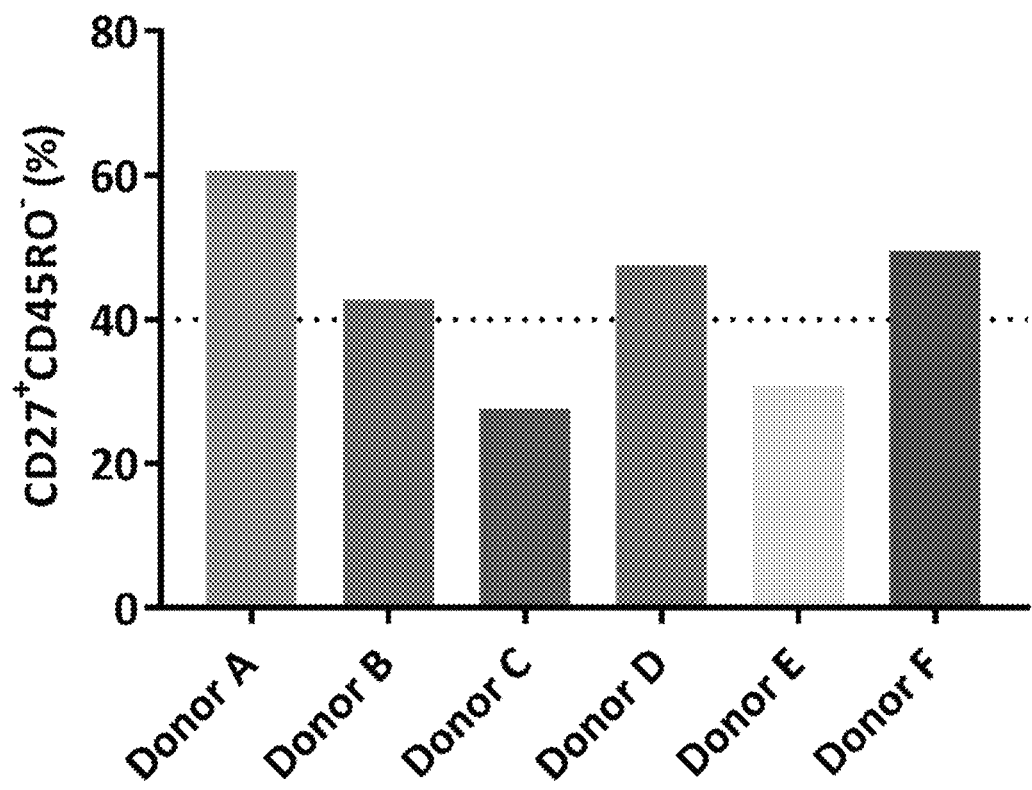
FIG. 15 is a bar graph showing percentage of CD27+ CD45RO− cells within the unedited CD8+ T cell subset of peripheral blood cells from six different donors.

Prior to modifying the cells, T cells from six different healthy donors were evaluated for expression of various cell surface markers. CD27+CD45RO− T cells within the CD8+ subset were previously shown to correlate with complete responses in chronic lymphocytic leukemia (CLL) when treated with anti-CD19 CAR T cell therapy (Fraietta et al., Nat Med, Vol. 24(5): 563-571, 2018). Accordingly, the percent of CD27+CD45O− T cells within the CD8+ subset of six different donors was evaluated by flow cytometry. In brief, 1×10⁶ cells were incubated with Fab-Biotin or IgG-Biotin antibodies as a negative control. Cells were washed with staining buffer and incubated with mouse anti-IgG to capture excess primary antibodies. Cells were washed again and incubated with the full panel of secondary antibodies (CD8, Biolegend: Catalog #300924, CD45RO, Biolegend: Catalog #304230, CD27, Biolegend: Catalog #560612) and viability dye. Cells were washed a final time with staining buffer and run on the flow cytometer to capture various stained populations. FIG. 15 shows the levels of CD27+ CD45RO− T cells within their CD8+ subsets. Allogeneic CAR-T manufacturing allows for the selection of donor input material with favorable characteristics, such as high CD27+CD45RO− cells in the CD8+ fraction of a donor of interest.

Figure 16:
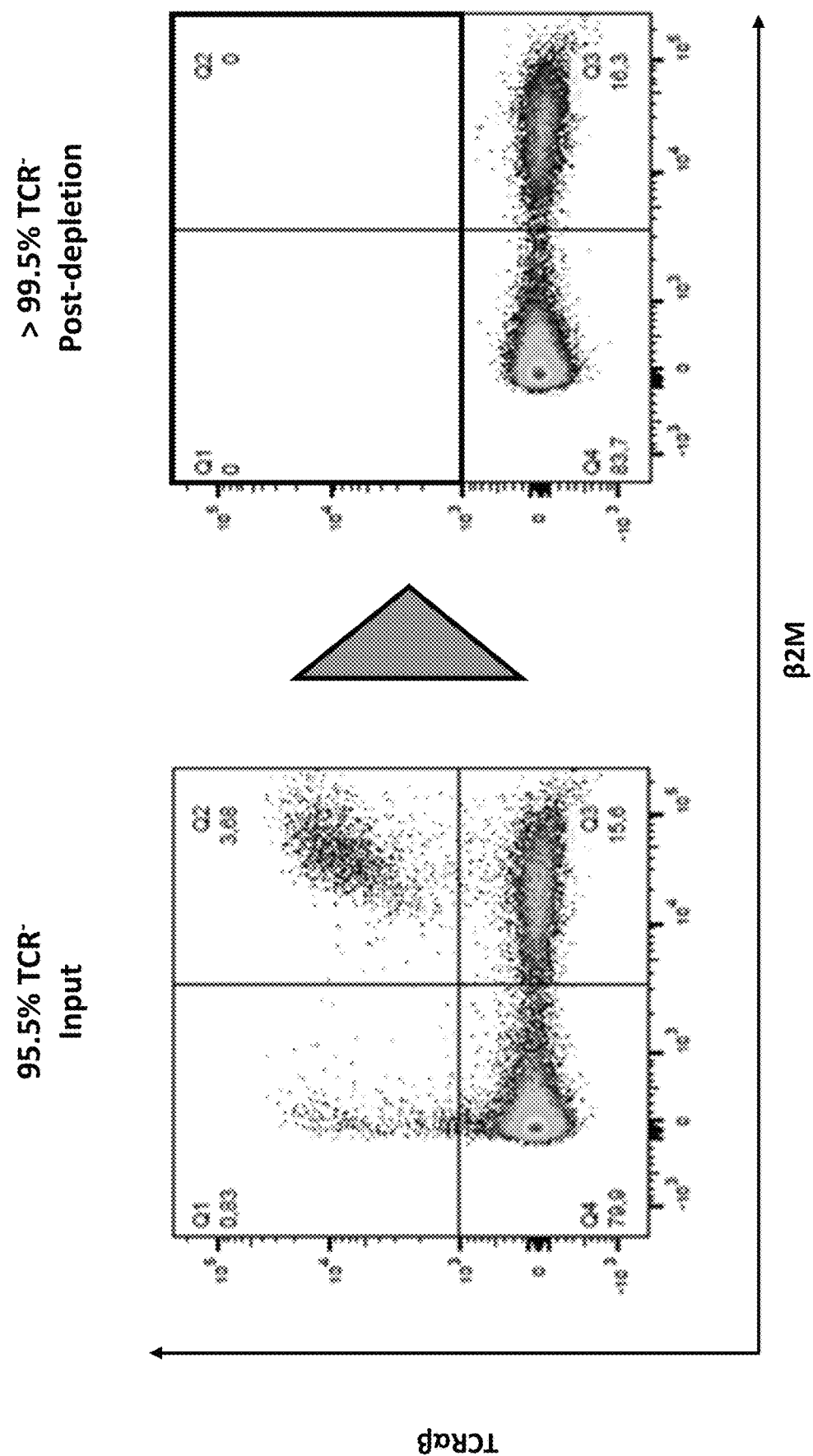
FIG. 16 provides flow cytometry results of TCRαβ and B2M expression on TC1 cells before and after depletion of TCRαβ+ cells.

More specifically, leukopaks from 18 to 40 year-old male donors were used to isolate CD4+ and CD8+ T cells. After isolation, enrichment and activation of CD4+ and CD8+ T cells, cells were electroporated with ribonucleoprotein complexes comprising Cas9 nuclease protein, TRAC sgRNA (SEQ ID NO: 26) or B2M sgRNA (SEQ ID NO: 27). The TRAC and B2M ribonucleoprotein complexes were combined prior to electroporation. After electroporation, freshly thawed rAAV comprising a donor template (SEQ ID NO: 54) encoding the anti-CD19 CAR (SEQ ID NO: 40) was added to the cells, and cells were incubated. Cells were then expanded in culture and supplemented with rhIL-2 and rhIL-7 every three to four days. Cells set up for monitoring were tested for T cell identity and gene editing with a TCR panel (CD5, CD4, CD8, TCRαβ, B2M and CD45). Upon confirmation of T cell identity, TCRαβ depletion was performed by incubating the cells with a biotin-conjugated anti-TCRαβ antibody and anti-biotin beads. The depleted cells were recovered and formulated for administration. The resulting population of cells had less than 0.5% TCRαβ+ cells. FIG. 16 shows the analysis of TCRαβ+ cells before and after purification.

Figure 17:
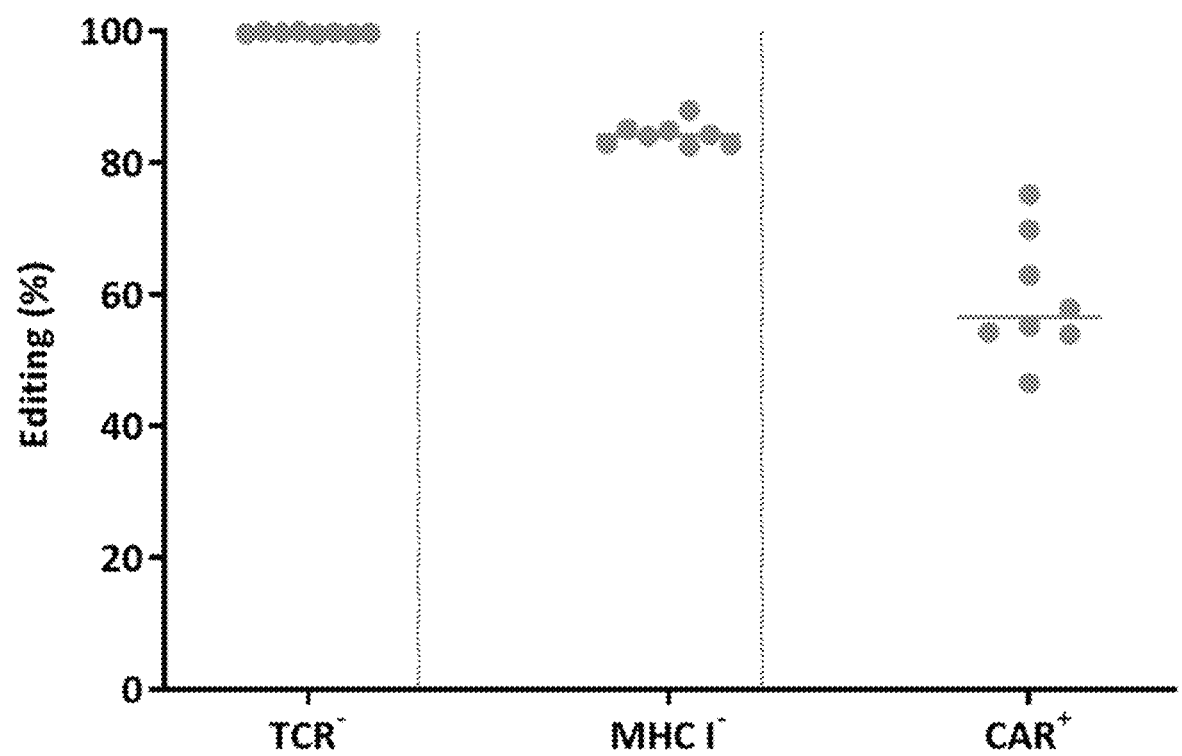
FIG. 17 is a graph the percentage loss of protein for TCR− and MHC I− (B2M) after gene editing, and percentage of cells expressing an anti-CD19 CAR in edited TC1 cells from individual lots of TC1 production.

Eight development lots of TC1 cells were tested for T cell identity. Average results from eight tested lots showed 84.58% knock-out of B2M (i.e., 15.42% B2M+ cells) and 99.98% of cells were TCR− (i.e., 0.2% TCR+), and ~50% knock-in of anti-CD19 CAR (FIG. 17).

Figure 18:
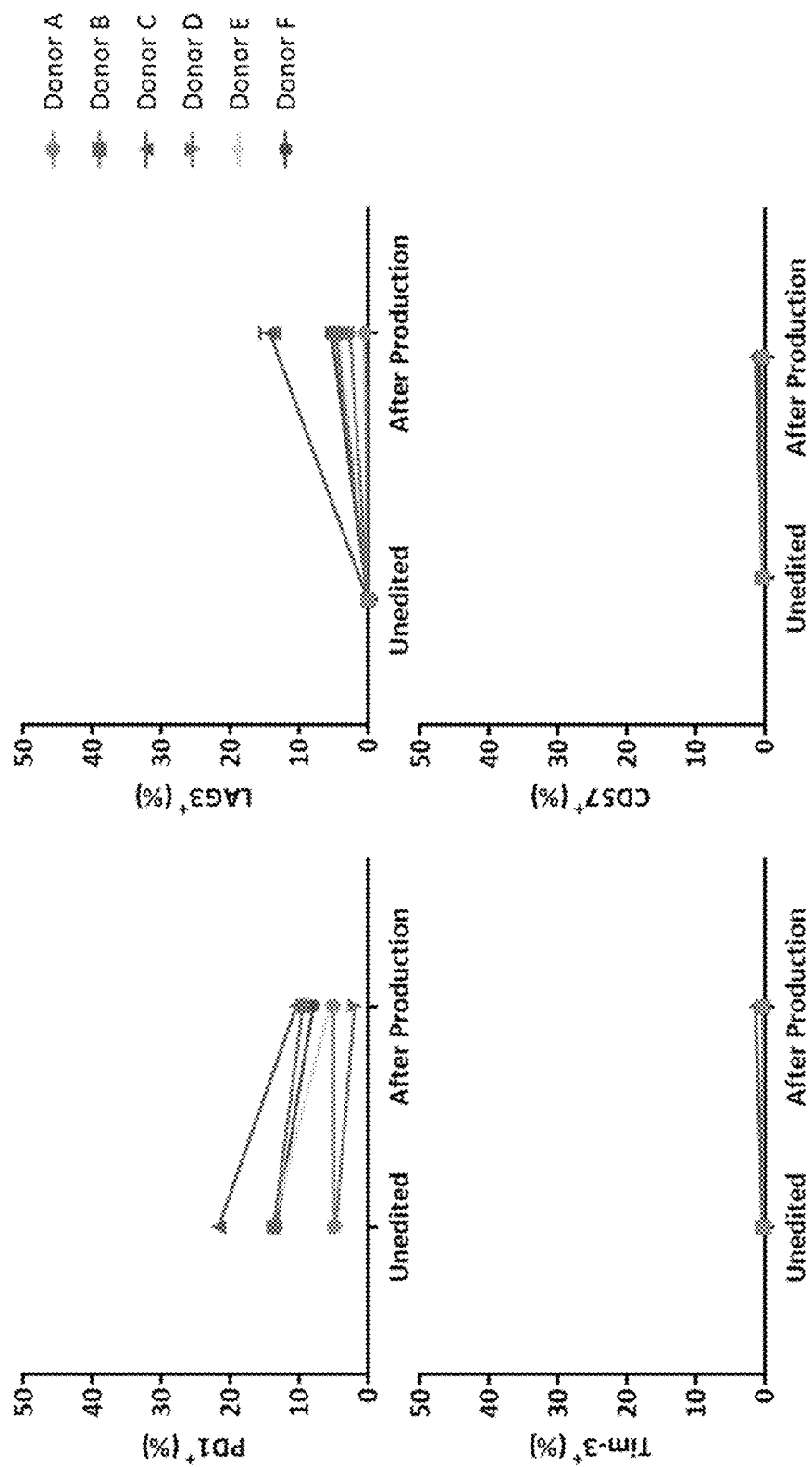
FIG. 18 provides graphs showing the percentage of PD1+ (top left), LAG3+ (top right), TIM3+ (bottom left) or CD57+ (bottom right) in the T cell population from six different donors before and after editing.

In addition, exhaustion and senescent markers were evaluated in donors before and after T cell editing. Specifically, the percentage of PD1+, LAG3+, TIM3+ and CD57+ cells were determined from total T cell populations. Expression of the markers was assessed by flow cytometry, as described above, using the following secondary antibodies: Mouse Anti-PD1 PeCy7, Biolegend, Catalog #329918; Mouse Anti-TIM3BV421, Biolegend, Catalog #345008; Mouse Anti-CD57 PerCp Cy5.5, Biolegend, Catalog #359622; and Mouse Anti-LAG3 PE, Biolegend, Catalog #369306. FIG. 18 shows that exhaustion or senescent markers never increased over 15% of the total T cell population after genome editing.

Figure 19:
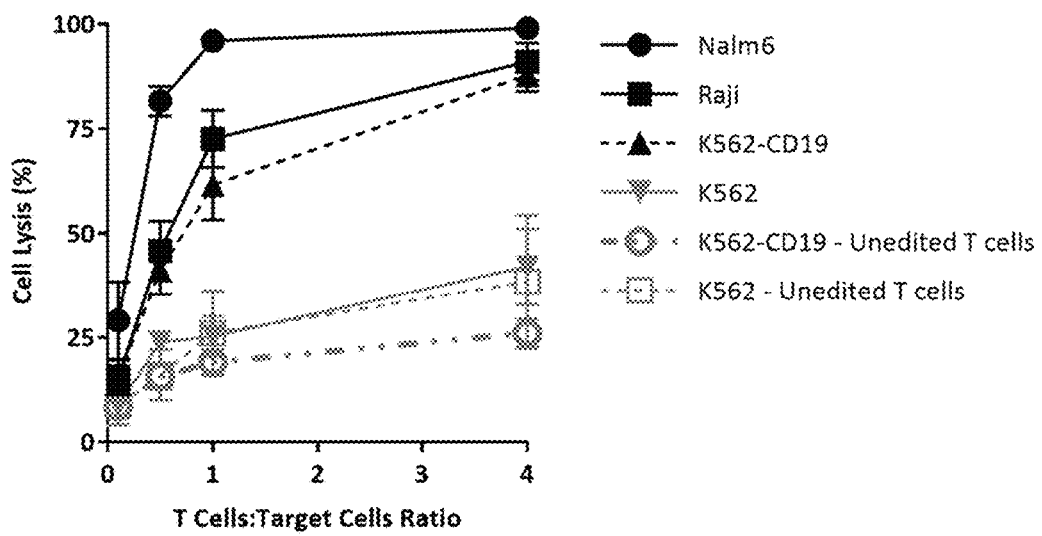
FIG. 19 is a graph showing the percentage of cell lysis of CD19-positive cell lines (Nalm6; Raji; and K562-CD19) and CD19-negative cells (K562) when co-cultured at different ratios with TC1 cells or unedited T cells.

In addition, selective killing by three different lots of TC1 cells was evaluated in vitro. Specifically, TC1 cells were incubated with CD19-positive cell lines (K562-CD19; Raji; and Nalm6), or a CD19-negative cell line (K562). Killing was measured using a flow cytometry-based cytotoxicity assay after ~24 hours. Specifically, target cells were labeled with 5 μM efluor670 (Thermo Fisher Scientific, Waltham, Mass.), washed and incubated overnight (50,000 target cells/well; 96-well U-bottom plate [Corning, Tewksbury, Mass.]) in co-cultures with TC1 or control T cells at varying ratios (from 0.1:1 up to 4:1 T cells to target cells). The next day, wells were washed and media was replaced with 200 μL of fresh media containing a 1:500 dilution of 5 mg/mL 4',6-diamidino-2-phenylindole (DAPI) (Thermo Fisher Scientific, Waltham, Mass.) to enumerate dead/dying cells. Finally, 25 µL of CountBright beads (Thermo Fisher Scientific) was added to each well, and cells were then analyzed by flow cytometry using a Novocyte flow cytometer (ACEA Biosciences, San Diego, Calif.). Flowjo software (v10, Flowjo, Ashland, Oreg.) was used to analyze flow cytometry data files (fcs files). TCRαβ+ T cells (unedited cells) were used as controls. TC1 cells efficiently killed CD19-positive cells at higher rates than unedited T cells, and CD19-negative cells showed low levels of cell lysis in the presence of TC1 cells that were no more than when co-cultured with unedited T cells (FIG. 19).

Figure 20:
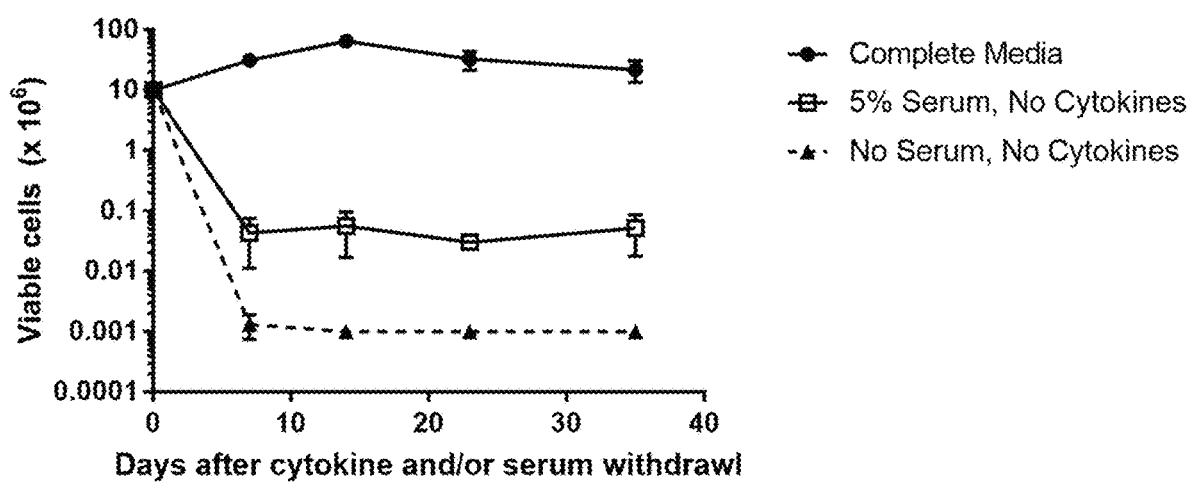
FIG. 20 is a graph showing the number of viable TC1 cells when cultured in the presence of T-cell media (serum+IL2+ IL7; Complete Media), media containing serum but no IL2 or IL7 cytokines (5% Serum, No cytokines) or no serum or cytokines (No Serum, No Cytokines). Cells were counted on the indicated days post gene editing. Mean values from three lots shown±SD.

TC1 cells produced from three unique donors were also used to assess growth in the absence of cytokine and/or serum. Specifically, TC1 cells were grown in full T cell media for 14 days. On Day 0, cells from culture were grown either in complete T-cell media (containing X-VIVO 15 (Lonza, Basel, Switzerland), 5% human AB serum (Valley Biomedical, Winchester, Va.), IL-2 (Miltenyi, Bergisch Gladbach, Germany) and IL-7 (Cellgenix, Frieburg, Germany)) (Complete Media), media containing serum but no IL-2 or IL-7 cytokines (5% serum, no cytokines), or no serum or cytokines (No serum, No Cytokines). Cells were enumerated as above for up to 35 days after removal of cytokines and/or serum. No outgrowth of TC1 cells was observed in the absence of cytokine and/or serum (FIG. 20).

For administration, TC1 cells are resuspended in cryopreservative solution (CryoStor CS-5) and supplied in a 6 mL infusion vial. The total dose is contained in one or more vials. The infusion of each vial occurs within 20 minutes of thawing.

Example 7: A Phase I, Open-Label, Multicenter, Dose Escalation and Cohort Expansion Study of the Safety and Efficacy of Allogeneic CRISPR-Cas9 Engineered T Cells (CTX110) in Subjects with Relapsed or Refractory B Cell Malignancies CTX110 is a CD19-directed chimeric antigen receptor (CAR) T cell immunotherapy comprised of allogeneic T cells that are genetically modified ex vivo using CRISPR-Cas9 (clustered regularly interspaced short palindromic repeats/CRISPR-associated protein 9) gene editing components (single guide RNA and Cas9 nuclease). The modifications include targeted disruption of the T cell receptor (TCR) alpha constant (TRAC) and beta-2 microglobulin (B2M) loci, and the insertion of an anti-CD19 CAR transgene into the TRAC locus via an adeno-associated virus expression cassette. The anti-CD19 CAR (SEQ ID NO: 40) is composed of an anti-CD19 single-chain variable fragment comprising the SEQ ID NO: 47, the CD8 transmembrane domain of SEQ ID NO: 32, a CD28 co-stimulatory domain of SEQ ID NO: 36, and a CD3ζ signaling domain of SEQ ID NO: 38.

In this study, eligible human patients received an intravenous (IV) infusion of CTX110 following lymphodepleting (LD) chemotherapy.

Study Population

Dose escalation and cohort expansion include adult subjects with B cell malignancies. Subjects are assigned to independent dose escalation groups based on disease histology. Enrolled adult subjects include those with select subtypes of non-Hodgkin lymphoma (NHL), including diffuse large B cell lymphoma (DLBCL) not otherwise specified (NOS), high grade B cell lymphoma with MYC and BCL2 and/or BCL6 rearrangements, transformed follicular lymphoma (FL), grade 3b FL or Richter's transformation of CLL.

Study Purpose and Rationale

The purpose of the Phase 1 dose escalation study is to evaluate the safety and efficacy of anti-CD19 allogeneic CRISPR-Cas9 engineered T cells (CTX110 cells) in subjects with relapsed or refractory B cell malignancies.

Outcomes for patients with relapsed/refractory B cell malignancies are historically poor. However, the use of autologous CAR T cell therapy in this setting has produced complete and durable responses where previous treatment options were palliative (June et al., (2018) *Science,* 359, 1361-1365; Maus and June, (2016) *Clin Cancer Res,* 22, 1875-1884; Neelapu et al., (2017) *N Engl J Med,* 377, 2531-2544; Schuster et al., (2019) *N Engl J Med,* 380, 45-56; Schuster et al., (2017) *N Engl J Med,* 377, 2545-2554). Autologous CAR T cell therapies require patient-specific cell collection and manufacturing. Unfortunately, some patients are not candidates to undergo leukapheresis, or they experience disease progression or death while awaiting treatment. An allogeneic off-the-shelf CAR T cell product such as CTX110 could provide the benefit of immediate availability, reduce manufacturing variability, and prevent individual subject manufacturing failures.

Further, patients treated with multiple rounds of chemotherapy may have T cells with exhausted or senescent phenotypes. The low response rates in patients with chronic lymphocytic leukemia (CLL) treated with autologous CAR T cell therapy have been partially attributed to the exhausted T cell phenotype (Fraietta et al., (2018) *Nat Med,* 24, 563-571; Riches et al., (2013) *Blood,* 121, 1612-1621). By starting with chemotherapy-naïve T cells from a healthy donor, allogeneic approaches could increase the consistency and potency of CAR T therapy as compared to autologous products.

The main barrier to the use of allogeneic CAR T cells has been the risk of graft versus host disease (GvHD). CRISPR Cas9 gene-editing technology allows for reliable multiplex cellular editing. The CTX110 manufacturing process couples the introduction of the CAR construct to the disruption of the TRAC locus through homologous recombination. The delivery and precise insertion of the CAR at the TRAC genomic locus using an AAV-delivered DNA donor template and HDR contrasts with the random insertion of genetic material using lentiviral and retroviral transduction methods. CAR gene insertion at the TRAC locus results in elimination of TCR in nearly all cells expressing the CAR, which minimizes risk of GvHD. Furthermore, manufacturing from healthy donor cells removes the risk of unintentionally transducing malignant B cells (Ruella et al., (2018) *Nat Med,* 24, 1499-1503). This first-in-human trial in subjects with relapsed/refractory B cell malignancies aims to evaluate the safety as well as efficacy of CTX110 with this CRISPR-Cas9-modified allogeneic CAR T cell approach.

CTX110, a CD19-directed genetically modified allogeneic T-cell immunotherapy, is manufactured from the cells of healthy donors; therefore, the resultant manufactured cells are intended to provide each subject with a consistent, final product of reliable quality. Furthermore, the manufacturing of CTX110, through precise delivery and insertion of the CAR at the TRAC site using AAV and homology-directed repair (HDR), does not present the risks associated with random insertion of lentiviral and retroviral vectors.

Objectives

Primary objective, Part A (Dose escalation): To assess the safety of escalating doses of CTX110 in combination with various lymphodepletion agents in subjects with relapsed or refractory B cell malignancies to determine the recommended Part B dose.

Primary objective, Part B (Cohort expansion): To assess the efficacy of CTX110 in subjects with relapsed or refractory B cell malignancies, as measured by objective response rate (ORR).

Secondary objectives (Parts A and B): To further characterize the efficacy, safety, and pharmacokinetics of CTX110.

Exploratory objectives (Parts A and B): To identify genomic, metabolic, and/or proteomic biomarkers associated with CTX110 that may indicate or predict clinical response, resistance, safety, or pharmacodynamic activity.

Endpoints

Primary Endpoints

Part A: The incidence of adverse events, defined as dose-limiting toxicities.

Part B: The objective response rate (ORR) defined as complete response (CR)+partial response (PR) per the Lugano Response Criteria for Malignant Lymphoma (Cheson et al., (2014) *J Clin Oncol,* 32, 3059-3068), as determined by independent central radiology review.

The Lugano Classification provides a standardized way to assess imaging in lymphoma subjects. It is comprised of radiologic assessments of tumor burden on diagnostic CT, and metabolic assessments on $F^{18}$ FDG-PET for FDG-avid histologies (see Tables 13-14).

TABLE 13

Lugano Classification Assessment Components.

| Diagnostic CT/MRI | $F^{18}$ FDG-PET | |
|---|---|---|
| Target Lymph Nodes and Extra Nodal Lesions | 5 Point Scale (Deauville) PET Score (Lymph Nodes and Extra Lymphatic Sites) * | |
| Up to 6 of the largest target nodes, nodal masses, or other lymphomatous lesions that are measurable in two diameters (longest diameter | The 5-point scale scores the site of the most intense FDG uptake for the time point, as follows: | |
| | Score | Criteria |
| [LDi] and shortest diameter) should be identified from different body regions representative of the subject's overall disease burden and include mediastinal and retroperitoneal disease, if involved. | 1 | No uptake |
| | 2 | Uptake ≤ mediastinum |
| | 3 | Uptake > mediastinum but ≤ liver |
| | 4 | Uptake moderately higher than liver (moderately indicates uptake greater than normal liver) |
| Nodal disease: Must have an LDi >1.5 cm Extranodal disease: Must have an LDi >1.0 cm Non-Measured Lesions | 5 | Uptake markedly higher than liver (markedly indicates much higher than normal liver) |
| All other lesions (including nodal, extranodal, and assessable disease) should be followed as nonmeasured disease (e.g., cutaneous, GI, bone, spleen, liver, kidneys, pleural or pericardial effusions, ascites). | | and/or New lesions |
| | X | New areas of uptake unlikely to be related to lymphoma |
| Organ Enlargement (Spleen) The spleen is considered enlarged (splenomegaly) when >13 cm in the cranial to caudal dimension. New Lesions Nodal disease: Must have an LDi >1.5 cm Extranodal disease: Any size | Bone Marrow: FDG uptake assessed as No FDG uptake consistent with lymphoma Focal FDG uptake consistent with lymphoma Diffuse FDG uptake consistent with lymphoma | |

CT: computed tomography; $F^{18}$ FDG: fluorodeoxyglucose F18; LDi: longest diameter; MRI: magnetic resonance imaging; PET: positron emission tomography.
* See (Barrington et al., (2014) *J Clin Oncol*, 32, 3048-3058).

TABLE 14

Lugano Criteria for Response Assessment.
At each follow-up time point, a PET-based response and a
CT-based response is made per the definitions below.

| Response and Site | PET-based Response | CT-based Response |
|---|---|---|
| COMPLETE | Complete Metabolic Response* ALL of the following | Complete Radiologic Response ALL of the following |
| Lymph nodes, extranodal lesions | Score of 1, 2, or 3* | Lymph nodes: All <1.5 cm in longest diameter. Extralymphatic disease absent. |
| Nonmeasured lesion | N/A | Absent |
| Organ enlargement | N/A | Spleen: normal size |
| New lesions | No new metabolically active lesions (new lesions drive score 5) | None |
| Bone marrow | No FDG-avid disease in marrow | Normal by morphology; if indeterminate, IHC negative. |
| PARTIAL | Partial Metabolic Response | Partial Remission ALL of the following |
| Lymph nodes, extranodal lesions | Score of 4, or 5 with reduced uptake from baseline and residual masses of any size | ≥50% decrease in SPD of all target lesions from baseline |

TABLE 14-continued

Lugano Criteria for Response Assessment.
At each follow-up time point, a PET-based response and a
CT-based response is made per the definitions below.

| | | |
|---|---|---|
| Nonmeasured lesion | N/A | Absent, normal, or regressed, but no increase |
| Organ enlargement | N/A | Spleen: >50% decrease from baseline in enlarged portion |
| New lesions | None | None |
| Bone marrow | Residual uptake higher than uptake in normal marrow but reduced compared with baseline (e.g., persistent focal changes in the marrow with nodal response) | N/A |
| NO RESPONSE/STABLE DISEASE | No Metabolic Response | Stable Disease |
| Lymph nodes, extranodal lesions | Score of 4, or 5 with no significant change in FDG uptake from baseline | <50% decrease in SPD of all target lesion from baseline No progression |
| Nonmeasured lesion | N/A | No increase consistent with progression |
| Organ enlargement | N/A | Spleen: No increase consistent with progression |
| New lesions | None | None |
| Bone marrow | No change from baseline | N/A |
| PROGRESSION | Progressive Metabolic Response | Progressive Disease ANY of the following |
| Lymph nodes, extranodal lesions | Lymph nodes/nodal masses: Score of 4 or 5 with increased uptake compared to baseline. Extranodal lesions: New FDG avid foci consistent with lymphoma. | PPD Progression An individual node/extranodal lesion must be abnormal (nodal disease with LDi >1.5 cm, extranodal disease with and LDi >1.0 cm) with: Increase of ≥50% from the product of the perpendicular diameters (PPD) from nadir AND Increase in LDi or SDi from nadir ≥0.5 cm for lesions ≤2 cm ≥1.0 cm for lesions >2 cm |
| Nonmeasured lesion | None | Unequivocal progression |
| Organ enlargement | None | Progression of pre-existing splenomegaly: Splenic length must increase by 50% of the extent of its prior increase beyond baseline (e.g., a 15-cm spleen must increase to 16 cm). New splenomegaly: Spleen must increase by at least 2 cm from baseline Or Recurrent splenomegaly |
| New lesions | New FDG-avid foci consistent with lymphoma rather than another etiology | Regrowth of previously resolved lesions New node >1.5 cm in any axis New extranodal site >1.0 cm in any axis New extranodal site <1.0 cm in any axis or unequivocal/attributable to lymphoma New assessable disease unequivocal/attributable to lymphoma of any size |
| Bone marrow | New/recurrent FDG-avid foci | New or recurrent involvement |

FDG: fluorodeoxyglucose; IHC: immunohistochemistry; LDi: longest diameter; N/A: not applicable; PPD: perpendicular diameters; SDi: shortest diameter; SPD: sum of the products of diameters.
* Deauville score of 3 represent a complete metabolic response (Barrington et al., (2014) *J Clin Oncol*, 32, 3048-3058).
Note:
It is recognized that in Waldeyer's ring or extranodal sites with high physiologic uptake or with activation within spleen or marrow (e.g., with chemotherapy or myeloid colony-stimulating factors), uptake may be greater than normal mediastinum and/or liver. In this circumstance, complete metabolic response may be inferred if uptake at sites of initial involvement is no greater than surrounding normal tissue even if the tissue has high physiologic uptake.

Secondary Endpoints (Dose Escalation and Cohort Expansion)

Efficacy

Duration of response/remission (central read/assessment). Duration of response/remission is reported only for subjects who have had objective response events. This is calculated as the time between first objective response and date of disease progression or death due to any cause.

Progression-free/event-free survival (central read/assessment). Progression-free survival (PFS) and event-free survival is calculated as the difference between date of CTX110 infusion and date of disease progression or death due to any cause. Subjects who have not progressed and are still on study at the data cutoff date are censored at their last assessment date.

Overall survival. Overall survival is calculated as the time between date of first dose of CTX110 and death due to any cause. Subjects who are alive at the data cutoff date are censored at their last date known to be alive.

Safety

Frequency and severity of AEs and clinically significant laboratory abnormalities.

Pharmacokinetic

Levels of CTX110 in blood over time.

Exploratory Endpoints (Dose Escalation and Cohort Expansion)

Levels of CTX110 in tissues (e.g., trafficking of CTX110 in bone marrow, CSF, and/or tumor tissue may be evaluated in any samples collected per protocol-specific sampling).

Levels of cytokines in blood and other tissues.

Incidence of anti-CTX110 antibodies.

Levels of B cells and immunoglobulins over time.

Impact of anti-cytokine therapy on CTX110 proliferation, CRS, and response.

Incidence of autologous or allogeneic HSCT following CTX110 therapy.

Incidence and type of subsequent anticancer therapy.

Time to complete response/remission.

First subsequent therapy-free survival.

Other genomic, protein, metabolic, or pharmacodynamic endpoints.

Study Design

This is an open-label, multicenter, Phase 1 study evaluating the safety and efficacy of CTX110 in subjects with relapsed or refractory B cell malignancies. The study is divided into 2 parts: dose escalation (Part A) followed by cohort expansion (Part B).

Part A investigates escalating doses of CTX110 in Cohort A in adult subjects with 1 of the following NHL subtypes: DLBCL NOS, high grade B cell lymphoma with MYC and BCL2 and/or BCL6 rearrangements, grade 3b FL, or transformed FL.

In the dose escalation part of the study, 1 additional cohort (Cohort B) with an NHL population similar to Cohort A has been added to explore an increased dose of cyclophosphamide (750 mg/m$^2$) relative to Cohort A (500 mg/m$^2$). Subjects in Cohort B are treated with an increased dose of cyclophosphamide to explore the effects of a longer suppression of lymphocytes on CAR T cell expansion following CTX110 infusion (see Table 15).

TABLE 15

Cohort A and Cohort B.

| Cohort | Disease Subset | Treatment |
| --- | --- | --- |
| A | Adult subjects with DLBCL NOS, high grade B cell lymphoma with MYC and BCL2 and/or BCL6 rearrangements, grade 3b FL, and transformed FL | LD chemotherapy: Co-administration of fludarabine 30 mg/m$^2$ + cyclophosphamide 500 mg/m$^2$ IV daily for 3 days CTX110 starting at DL1 |
| B | Same as Cohort A | LD chemotherapy: Co-administration of fludarabine 30 mg/m$^2$ + cyclophosphamide 750 mg/m$^2$ IV daily for 3 days CTX110 starting at DL2 |

DL1/2: Dose Level 1 or 2; DLBCL: diffuse large B cell lymphoma; FL: follicular lymphoma; IV: intravenously; LD: lymphodepleting.

Figure 21:
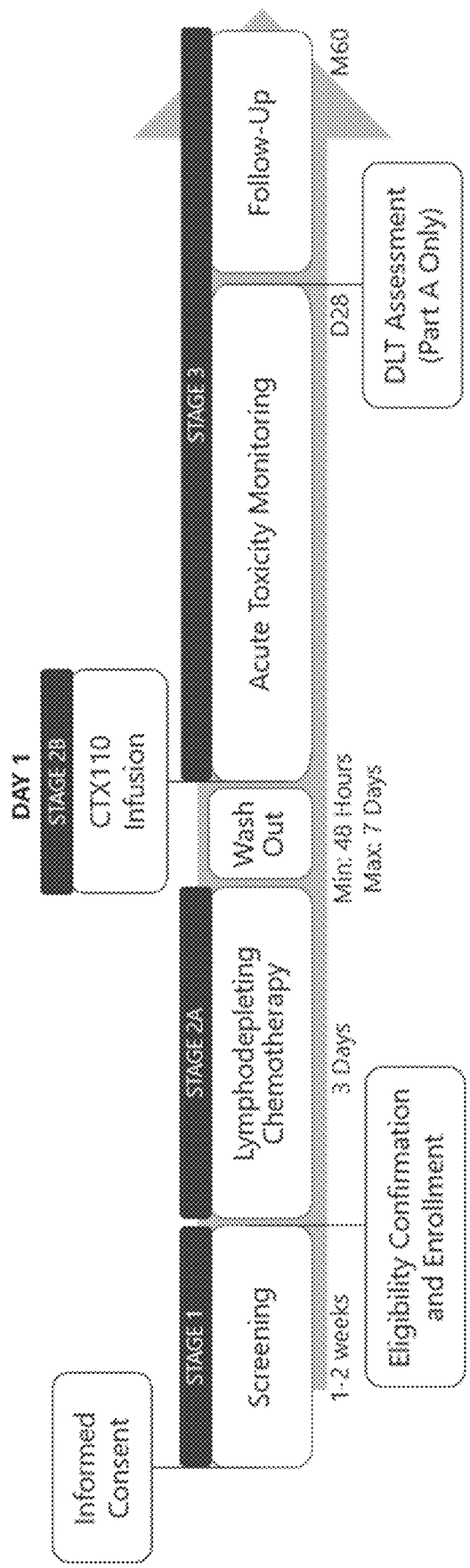
FIG. 21 is a schematic depicting the clinical study design to evaluate CTX110 cells, (a.k.a., TC1 cells) administered after lymphodepletion to human subjects having CD19+ malignancies.

The study is divided into 2 parts: dose escalation (Part A) followed by cohort expansion (Part B). Both parts of the study will consist of 3 main stages: screening, treatment, and follow-up. A schematic depiction of the study schema is shown in FIG. 21.

A schedule of assessments is provided in Table 16 and Table 17.

Stage 1—Screening to determine eligibility for treatment (up to 14 days).

Stage 2—Lymphodepleting (LD) chemotherapy and infusion of CTX110 (1-2 weeks). Prior to both the initiation of LD chemotherapy and infusion of CTX110, the clinical eligibility of subjects must be reconfirmed.

Stage 2A—LD chemotherapy:

Cohort A: Co-administration of fludarabine 30 mg/m$^2$ and cyclophosphamide 500 mg/m$^2$ intravenously (IV) daily for 3 days.

Cohort B: Co-administration of fludarabine 30 mg/m$^2$ and cyclophosphamide 750 mg/m$^2$ intravenously (IV) daily for 3 days.

Stage 2B—CTX110 infusion:

Cohort A (NHL subsets): Lymphodepleting (LD) chemotherapy (fludarabine 30 mg/m$^2$ and cyclophosphamide 500 mg/m$^2$ intravenously [IV] daily for 3 days) completed at least 48 hours (but no more than 7 days) prior to CTX110 infusion (dose escalation from Dose Level [DL] 1).

Cohort B (higher LD chemotherapy dose): LD chemotherapy (fludarabine 30 mg/m$^2$ and cyclophosphamide 750 mg/m$^2$ IV daily for 3 days) completed at least 48 hours (but no more than 7 days) prior to CTX110 infusion (dose escalation from Dose Level [DL]2).

Stage 3—Follow up (5 years after the last CTX110 infusion).

For both dose escalation and cohort expansion, subjects must remain within proximity of the investigative site (i.e., 1-hour transit time) for 28 days after CTX110 infusion. During this acute toxicity monitoring period, subjects will be routinely assessed for adverse events (AEs), including cytokine release syndrome (CRS), neurotoxicity, and GvHD. Toxicity management guidelines are provided in the study protocol. During dose escalation, all subjects will be hospitalized for the first 7 days following CTX110 infusion, or longer if required by local regulation or site practice.

After the acute toxicity monitoring period, subjects will be subsequently followed for up to 5 years after CTX110 infusion with physical exams, regular laboratory and imaging assessments, and AE evaluations. After completion of this study, subjects will be required to participate in a separate long-term follow-up study for an additional 10 years to assess long-term safety and survival.

LD chemotherapy it to be delayed if any of the following signs or symptoms are present:
- Significant worsening of clinical status that, according to the investigator, increases the potential risk of AEs associated with LD chemotherapy.
- Requirement for supplemental oxygen to maintain a saturation level of >91%.
- New uncontrolled cardiac arrhythmia.
- Hypotension requiring vasopressor support.
- Active infection: Positive blood cultures for bacteria, fungus, or virus not responding to treatment.
- Grade ≥2 acute neurological toxicity.

TABLE 16

Schedule of Assessments (Screening to Month 24).

| | Screening [1] (Stage 1) | Treatment (Stage 2) | | | | | | | | | Follow-up (Stage 3) | | | | | | | |
|---|---|---|---|---|---|---|---|---|---|---|---|---|---|---|---|---|---|---|
| | | | | | | | | Day | | | | | | | | | | |
| | D −5 to D −3 | D 1[(2)] | D 2 ± 2 d | D 3 ± 2 d | D 5 ± 2 d | D 8 ± 2 d | D 10 ± 2 d | D 14 ± 2 d | D 21 ± 2 d | D 28 ± 4 d | M 2 ± 7 d | M 3 ± 7 d | M 6 ± 14 d | M 9 ± 14 d | M 12 ± 14 d | M 15 ± 14 d | M 18 ± 14 d | M 24 ± 21 d |
| Informed consent | X | | | | | | | | | | | | | | | | | |
| Medical history[3] | X | | | | | | | | | | | | | | | | | |
| Physical exam | X | X | X | X | X | X | X | X | X | X | X | X | X | X | X | X | X | X |
| Vital signs [4] | X | X | X | X | X | X | X | X | X | X | X | X | X | X | X | X | X | X |
| Height, weight [5] | X | X | X | | | X | | X | | X | X | X | X | X | X | X | X | X |
| Pregnancy test [6] | X | X | | | | | | | | | | | | | | | | |
| ECOG status | X | | X | | | | | | | X | X | | | | | | | |
| Echocardiogram | X | | | | | | | | | | | | | | | | | |
| 12-lead ECG [7] | X | X | X | | | | | | | X | | | | | | | | |
| Brain MRI | X | | | | | | | | | | | | | | | | | |
| Lumbar puncture [8] | X | | | | | | | | | | | | | | | | | |
| ICE assessment [9] | X | | X | X | X | X | X | | | X | | | | | | | | |
| Patient-reported outcome | X | | | | | | | | | | X | X | | X | | | | X |
| Concomitant meds [10] | | | | | | | | | Continuous | | | | | | | | | |
| Adverse events [11] | | | | | | | | | Continuous | | | | | | | | | |
| Hospital utilization | | | | | | | | | Continuous | | | | | | | | | |
| Treatment | | | | | | | | | | | | | | | | | | |
| LD chemotherapy [12] | | X | | | | | | | | | | | | | | | | |
| CTX110 infusion [13] | | | X | | | | | | | | | | | | | | | |
| NHL Disease Response/Assessment (Central and Local) | | | | | | | | | | | | | | | | | | |
| PET/CT scan [14] | X | | | | | | | | | X | | X | X | X | X | | X | X |
| BM biopsy [15] | X | | | | | | | | | X | | | | | | | | |
| Tumor biopsy [16] | | | | | | | | | | X | | | | | | | | |
| Tumor pathology[17] | X | | | | | | | | | | | | | | | | | |
| Adult B Cell ALL Disease Response/Assessment | | | | | | | | | | | | | | | | | | |
| BM biopsy and aspirate (central and local) [14, 15] | X | | | | | | | | | X | X [18] | X [18] | | | | | | |
| Peripheral blood chimerism (local) [19] | X | | | | | | | | | | | | | | | | | |
| Laboratory Assessments (Local) | | | | | | | | | | | | | | | | | | |
| CBC w/differential | X | X | X | X | X | X | X | X | X | X | X | X | X | X | X | X | X | X |
| Serum chemistry | X | X | X | X | X | X | X | X | X | X | X | X | X | X | X | X | X | X |
| Coagulation parameters | X | X | X | X | X | X | X | X | X | | X | | | | | | | |
| Viral serology [20] | X | | | | | | | | | | | | | | | | | |
| Immunoglobulins | X | | X | | | | | | | X | X | X | X | X | X | X | X | X |
| Ferritin, CRP | X | | X | X | X | X | X | X | X | X | | | | | | | | |
| Lymphocyte subsets [21] | X | X | X | | X | X | X | | X | X | X | X | X | X | X | | | |
| B cells (CD 19, CD20) | X | | X | | | | | | | X | X | X | X | X | X | X | X | X |
| Blood type, Ab screen [22] | X | | | | | | | | | | | | | | | | | |
| Biomarkers (Blood, Central) | | | | | | | | | | | | | | | | | | |
| CTX110PK [23, 24] | X | | X [25] pre/post | X | X | X | X | X | X | X | X | X | X | X | X | X | X | X |

TABLE 16-continued

Schedule of Assessments (Screening to Month 24).

| | Study Stage | | | | | | | | | | | | | | | | |
|---|---|---|---|---|---|---|---|---|---|---|---|---|---|---|---|---|---|
| | Screening [1] (Stage 1) | Treatment (Stage 2) | | | | | | | | Follow-up (Stage 3) | | | | | | | |
| | | | | | | | | Day | | | | | | | | | |
| | | D −5 to D −3 | D 1[(2)] | D 2 ± 2 d | D 3 ± 2 d | D 5 ± 2 d | D 8 ± 2 d | D 10 ± 2 d | D 14 ± 2 d | D 21 ± 2 d | D 28 ± 4 d | M 2 ± 7 d | M 3 ± 7 d | M 6 ± 14 d | M 9 ± 14 d | M 12 ± 14 d | M 15 ± 14 d | M 18 ± 14 d | M 24 ± 21 d |
| Cytokines [26] | X | | X | X | X | X | X | X | X | X | X | X | | | | | | | |
| Anti-Cas9 Ab [24] | X | | | | | | | | | | X | | X | | X | | | X |
| Anti-CTX110 Ab [24] | X | | | | | | | | | | X | | X | | X | | | X |
| immunophenotype | X | | X [25] pre/post | | X | X | X | | X | X | X | X | X | X | X | X | X | X | X |
| DNA | X | | | | | | | | | | | | | | | | | | |
| Cell-free DNA | X | | | | | | | | | | X | X | X | X | | X | | X | X |
| PBMCs | X | | | | | | | | | | X | | X | X | X | X | | X | X |
| Exploratory biomarkers [27] | X | X [28] | X | X | X | X | X | X | X | X | X | X | X | X | X | X | X | X | X |

Ab: antibody; AE: adverse event; BM: bone marrow; Cas9: CRISPR-associated protein 9; CBC: complete blood count; CNS: central nervous system; CRISPR: clustered regularly interspaced short palindromic repeats; CRP: C-reactive protein; CT: computed tomography; D or d: day; $EC_{90}$: 90% effective concentration; ECG: electrocardiogram; ECOG: Eastern Cooperative Oncology Group; HBV: hepatitis B virus; HCV: hepatitis C virus; HIV-1/-2: human immunodeficiency virus type 1 or 2; HSCT: hematopoietic stem cell transplant; ICE: immune effector cell-associated encephalopathy; ICF: informed consent form; IPI: International Prognostic Index; LD: lymphodepleting; LP: lumbar puncture; M: month; MRI: magnetic resonance imaging; PBMC: peripheral blood mononuclear cell; PCR: polymerase chain reaction; PET: positron emission tomography; PK: pharmacokinetic(s); Q: every; TBNK: T-, B-, natural killer (cells).

[1] Screening assessments completed within 14 days of informed consent. Subjects allowed 1-time rescreening within 3 months of initial consent.
[(2)] All baseline assessments on Day 1 are to be performed prior to CTX110 infusion unless otherwise specified.
[3] Includes complete surgical and cardiac history.
[4] Includes sitting blood pressure, heart rate, respiratory rate, pulse oximetry, and temperature.
[5] Height at screening only.
[6] For female subjects of childbearing potential. Serum pregnancy test at screening. Serum or urine pregnancy test within 72 hours before start of LD chemotherapy.
[7] Prior to LD chemotherapy, and prior to CTX110 infusion.
[8] LP at screening on subjects with high risk for CNS involvement (e.g., high-grade B cell lymphoma with MYC and BCL2 and/or BCL6 rearrangements, subjects with testicular involvement of lymphoma, or subjects with high-risk CNS IPI score). For LPs performed during neurotoxicity, samples should be sent to central laboratory for CTX110 PK and exploratory biomarkers whenever possible.
[9] On Day 1 prior to CTX110 administration. If CNS symptoms persist after Day 28, ICE assessment should continue to be performed approximately every 2 days until symptom resolution to grade 1 or baseline.
[10] All concomitant medications will be collected ≤3 months post-CTX110, after which only select concomitant medications will be collected.
[11] Collect all AEs from informed consent to Month 3 visit, collect all SAEs and AESIs after Month 3 visit to Month 60 visit. Only SAEs and AESIs should be reported for ≤3 months post-CTX110 if subject begins new anticancer therapy before Month 3 visit. Only AESIs will be reported if subject begins new anticancer therapy after Month 3 visit.
[12] Start LD chemotherapy within 7 days of study enrollment. After completion of LD chemotherapy, ensure washout period of ≥48 hours (but ≤7 days) before CTX110 infusion. Physical exam, weight, and coagulation laboratories performed prior to first dose of LD chemotherapy. Vital signs, CBC, clinical chemistry, and AEs/concomitant medications assessed and recorded daily (i.e., 3 times) during LD chemotherapy.
[13] CTX110 administered 48 hours to 7 days after completion of LD chemotherapy.
[14] Baseline disease assessment (PET/CT for subjects with NHL) to be performed within 28 days prior to CTX110 infusion. MRI with contrast allowed if CT clinically contraindicated, or as required by local regulation.
[15] BM biopsy to confirm complete response as part of disease evaluation. BM biopsy may also be performed at time of disease relapse. Samples from BM aspirate after CTX110 infusion should be sent for CTX110 PK and exploratory biomarkers. To be performed ±5 days of visit date.
[16] Optional: For subjects who have disease amenable to biopsy and who provide separate consent. To be performed ±5 days of visit date.
[17] It is preferred that subjects undergo tumor biopsy during screening. However, if a biopsy of relapsed/refractory disease was performed within 3 months prior to enrollment and after the most recent line of therapy, archival tissue may be used. If relapse occurs on study, every attempt should be made to obtain biopsy of relapsed tumor and send to central pathology. Tumor biopsy refers to tissue other than bone marrow.
[18] Assessments at Months 2 and 3 to confirm CR if not achieved at Month 1.
[19] To be performed only in subjects who have received prior allogeneic HSCT.
[20] Infectious disease testing (HIV-1, HIV-2, HCV antibody/PCR, HBV surface antigen, HBV surface antibody, HBV core antibody) ≤30 days of signing ICF may be considered for subject eligibility.
[21] Lymphocyte subset assessment at screening, before start of first day of LD chemotherapy, before CTX110 infusion, then all listed time points. To include 6-color TBNK panel, or equivalent for T, B, and natural killer cells.
[22] Blood type and antibody screen.
[23] Samples for CTX110 PK should be sent from any LP, BM biopsy, or tissue biopsy performed following CTX110 infusion. If CRS occurs, samples for assessment of CTX110 levels will be collected every 48 hours between scheduled visits until CRS resolves.
[24] Sponsor may request discontinuation of sample collection if consecutive tests are negative. Continue sample collection for all listed time points until otherwise instructed by sponsor.
[25] Two samples collected on Day 1: One pre-CTX110 infusion and one 20 (±5) minutes after the end of CTX110 infusion.
[26] Additional cytokine samples should be collected daily for the duration of CRS. Day 1 samples to be collected prior to CTX110 infusion.
[27] Samples for exploratory biomarkers should be sent from any LP or BM biopsy performed following CTX110 infusion. If CRS occurs, samples for assessment of exploratory biomarkers will be collected every 48 hours between scheduled visits until CRS resolves.
[28] Prior to first day of LD chemotherapy only.

TABLE 17

Schedule of Assessments (Months 30-60).

| Assessments | M 30 (±21 days) | M 36 (±21 days) | M 42 (±21 days) | M 48 (±21 days) | M 54 (±21 days) | M 60 (±21 days) | Progressive Disease | Secondary Follow-Up [1] |
|---|---|---|---|---|---|---|---|---|
| Vital signs [2] | X | X | X | X | X | X | X | X |
| Physical exam | X | X | X | X | X | X | X | X |
| Concomitant medications [3] | X | X | X | X | X | X | X | X |
| Disease assessment [4] | X | X | X | X | X | X | X | |

TABLE 17-continued

Schedule of Assessments (Months 30-60).

| Assessments | M 30 (±21 days) | M 36 (±21 days) | M 42 (±21 days) | M 48 (±21 days) | M 54 (±21 days) | M 60 (±21 days) | Progressive Disease | Secondary Follow-Up [1] |
|---|---|---|---|---|---|---|---|---|
| CBC with differential [5] | X | X | X | X | X | X | X | X |
| Serum chemistry [5] | X | X | X | X | X | X | X | X |
| Immunoglobulins [5, 6] | X | X | X | X | X | X | X | |
| Lymphocyte subsets [5, 6] | X | X | X | X | X | X | X | |
| CTX110 persistence (blood, central) [6, 7] | X | X | X | X | X | X | X | X |
| Exploratory biomarkers (blood, central) | X | X | X | X | X | X | X | X |
| Anti-Cas9 Ab (blood, central) [6] | | X | | X | | X | X | |
| Anti-CTX110, anti-daratumumab Ab (blood, central) [6] | | X | | X | | X | X | |
| Patient-reported outcome | | X | | X | | X | X | |
| Adverse events [8] | X | X | X | X | X | X | X | X |

Ab: antibody; AESI: adverse event of special interest; BM: bone marrow; Cas9: CRISPR-associated protein 9; CBC: complete blood count; CRISPR: clustered regularly interspaced short palindromic repeats; CT: computed tomography; NHL: non-Hodgkin lymphoma; PET: positron emission tomography; PK: pharmacokinetic; SAE: serious adverse event; TBNK: T-, B-, natural killer (cells).
[1] Subjects with progressive disease or who undergo stem cell transplant will discontinue the normal schedule of assessments and attend annual study visits. Visits will occur at 12-month intervals. Subjects who partially withdraw consent will undergo these procedures at minimum.
[2] Includes temperature, blood pressure, pulse rate, and respiratory rate.
[3] Only select concomitant medications will be collected.
[4] Disease assessment will consist of investigator review of physical exam, CBC, clinical chemistry, and lactate dehydrogenase for NHL subjects, and of physical exam, CBC with differential, and clinical chemistry for B cell ALL. NHL subjects with suspected malignancy will undergo PET/CT imaging and/or a BM biopsy to confirm relapse. Every attempt should be made to obtain a biopsy of the relapsed tumor in subjects who progress.
[5] Assessed at local laboratory. To include 6-color TBNK panel, or equivalent for T, B, and natural killer cells.
[6] Sponsor may request discontinuation of sample collection. Continue sample collection for all listed time points until otherwise instructed by sponsor.
[7] Samples for CTX110 PK analysis should be sent to the central laboratory from any lumbar puncture, BM biopsy, or tissue biopsy performed following CTX110 infusion.
[8] SAEs and AESIs should be reported for up to 3 months after CTX110 infusion if a subject begins new anticancer therapy before Month 3 study visit. Only AESIs will be reported if a subject begins new anticancer therapy after Month 3 study visit.

The goal of lymphodepletion is to allow for significant CAR T cell expansion following infusion. LD chemotherapy consisting of fludarabine and cyclophosphamide across different doses has been successfully utilized in several autologous CAR T cell trials. The rationale for the use of LD chemotherapy is to eliminate regulatory T cells and other competing elements of the immune system that act as 'cytokine sinks,' enhancing the availability of cytokines such as interleukin 7 (IL-7) and interleukin 15 (IL-15) (Dummer et al., (2002) *J Clin Invest*, 110, 185-192; Gattinoni et al., (2005) *J Exp Med*, 202, 907-912). Additionally, it is postulated that naïve T cells begin to proliferate and differentiate into memory-like T cells when total numbers of naïve T cells are reduced below a certain threshold (Dummer et al., (2002) *J Clin Invest*, 110, 185-192). Cohort A will use cyclophosphamide (500 mg/m$^2$) and fludarabine (30 mg/m$^2$) at doses that are consistent with doses used in registrational clinical trials of axicabtagene ciloleucel. Cohort B will use a higher dose of cyclophosphamide (750 mg/m$^2$) to evaluate whether increased intensity of lymphodepletion may facilitate expansion of an allogeneic CAR T cell product. Doses of cyclophosphamide within this range (total of >120 mg/kg or 3 g/m$^2$) have been used in prior CAR T cell therapy studies in hematological malignancies (Brentjens et al., (2011) *Blood*, 118, 4817-4828; Kochenderfer et al., (2015) *J Clin Oncol*, 33, 540-549; Turtle et al., (2016) *Sci Transl Med*, 8, 355ra116). When used as a part of higher intensity LD chemotherapy, increased doses of cyclophosphamide are associated with improved efficacy (Hirayama et al., (2019) *Blood*, 133, 1876-1887).

CTX110 infusion is to be delayed if any of the following signs or symptoms are present:
  New active uncontrolled infection.
  Worsening of clinical status compared to prior to start of LD chemotherapy that, in the opinion of the investigator, places the subject at increased risk of toxicity.
  Grade ≥2 acute neurological toxicity.

CTX110 Dose

CTX110 cells are administered IV using a flat dosing schema based on the number of CAR+ T cells. The starting dose is $3 \times 10^7$ CAR+ T cells, which is approximately 1 log lower than the doses of autologous CAR T cells currently approved for NHL including KYMRIAH® ($5 \times 10^8$ total CAR T cells) and YESCARTA® ($2 \times 10^6$ kg, maximum $2 \times 10^8$ CAR T cells).

Dose Escalation

Dose escalation will be performed using a standard 3+3 design. The following doses of CTX110, based on CAR+ T cells, may be evaluated in this study beginning with DL1 for Cohort A. Only after assessment and confirmation of safety of DL2 in Cohort A by the Safety Review Committee (SRC) may subsequent Cohort B be opened/enrolled and begin dose escalation from DL2. Due to the study's dose limit of $7 \times 10^4$ TCR+ cells/kg, the study may proceed with DL4 in Cohort A and/or Cohort B if a subject weighs ≥60 kg (see Table 18).

TABLE 18

Dose Levels.

| Dose Level | Total CAR+ T Cell Dose |
|---|---|
| −1 | $1 \times 10^7$ |
| 1 | $3 \times 10^7$ |
| 2 | $1 \times 10^8$ |
| 3 | $3 \times 10^8$ |
| 4 | $1 \times 10^9$ |

CAR: chimeric antigen receptor.

The DLT evaluation period begins with CTX110 infusion and last for 28 days. The first 3 subjects in each cohort will be treated in a staggered manner, such that the 2$^{nd}$ and 3$^{rd}$ subjects will only receive CTX110 after the previous subject has completed the DLT evaluation period. In subsequent dose levels or expansion of the same dose level, cohorts of up to 3 subjects may be enrolled and dosed concurrently.

Subjects must receive CTX110 to be evaluated for DLT. If a subject discontinues the study any time prior to CTX110 infusion, the subject will not be evaluated for DLT and a replacement subject will be enrolled at the same dose level as the discontinued subject. If a DLT-evaluable subject has signs or symptoms of a potential DLT, the DLT evaluation period will be extended according to the protocol-defined window to allow for improvement or resolution before a DLT is declared.

Toxicities are graded and documented according to National Cancer Institute Common Terminology Criteria for Adverse Events (CTCAE) version 5, except for CRS (Lee criteria), neurotoxicity (ICANS, immune effector cell-associated neurotoxicity syndrome criteria and CTCAE v5.0), and GvHD (Mount Sinai Acute GVHD International Consortium [MAGIC] criteria).

A DLT will be defined as any of the following events occurring during the DLT evaluation period that persists beyond the specified duration (relative to the time of onset):
  Grade ≥2 GvHD that is steroid-refractory (e.g., progressive disease after 3 days of steroid treatment [e.g., 1 mg/kg/day], stable disease after 7 days, or partial response after 14 days of treatment).
  Death during the DLT period (except due to disease progression).
  Any grade 3 or 4 toxicity that is clinically significant according to the investigator's judgement and does not improve within 72 hours.
The following will NOT be considered as DLTs:
  Grade 3 or 4 CRS that improves to grade ≤2 within 72 hours.
  Grade 3 or 4 neurotoxicity (e.g., encephalopathy, confusion) that improves to grade ≤2 within 14 days.
  Grade 3 or 4 fever.
  Bleeding in the setting of thrombocytopenia (platelet count ≤50×10$^9$/L); documented bacterial infections or fever in the setting of neutropenia (absolute neutrophil count <1000/mm$^3$).
  Grade 3 or 4 hypogammaglobulinemia.
  Grade 3 or 4 pulmonary toxicity that resolves to grade ≤2 within 7 days. For subjects intubated due to fluid overload from supportive care, this may be extended to 14 days.
  Grade 3 or 4 liver function studies that improve to grade ≤2 within 14 days.
  Grade 3 or 4 renal insufficiency that improves to grade ≤2 within 21 days.
  Grade 3 or 4 thrombocytopenia or neutropenia will be assessed retrospectively. After at least 6 subjects are infused, if ≥50% of subjects have prolonged cytopenias (i.e., lasting more than 28 days post-infusion), dose escalation will be suspended pending SRC assessment.
AEs that have no plausible causal relationship with CTX110 will not be considered DLTs.

Toxicity Management

Subjects must be closely monitored for at least 28 days after CTX110 infusion. Significant toxicities have been reported with autologous CAR T cell therapies and investigators are required to proactively monitor and treat all adverse events in accordance with protocol guidance.

The following general recommendations are provided based on prior experience with CD19-directed autologous CAR T cell therapies:
  Fever is the most common early manifestation of cytokine release syndrome (CRS); however, subjects may also experience weakness, hypotension, or confusion as first presentation.
  Diagnosis of CRS should be based on clinical symptoms and NOT laboratory values.
  In subjects who do not respond to CRS-specific management, always consider sepsis and resistant infections. Subjects should be continually evaluated for resistant or emergent bacterial infections, as well as fungal or viral infections.
  CRS, hemophagocytic lymphohistiocytosis (HLH), and tumor lysis syndrome (TLS) may occur at the same time following CAR T cell infusion. Subjects should be consistently monitored for signs and symptoms of all the conditions and managed appropriately.
  Neurotoxicity may occur at the time of CRS, during CRS resolution, or following resolution of CRS. Grading and management of neurotoxicity will be performed separately from CRS.
  Tocilizumab must be administered within 2 hours from the time of order.

The safety profile of CTX110 will be continually assessed throughout the study, and investigators will be updated on a regular basis with new information regarding the identification and management of potential CTX110-related toxicity.

Infusion Reactions

Infusion reactions have been reported in autologous CD19-directed CAR T cell trials, including transient fever, chills, and/or nausea. Acetaminophen (paracetamol) and diphenhydramine hydrochloride (or another H1-antihistamine) may be repeated every 6 hours after CTX110 infusion, as needed, if an infusion reaction occurs. Nonsteroidal anti-inflammatory medications may be prescribed, as needed, if the subject continues to have fever not relieved by acetaminophen. Systemic steroids should not be administered except in cases of life-threatening emergency, as this intervention may have a deleterious effect on CAR T cells.

Febrile Reaction and Infection Prophylaxis

Infection prophylaxis should occur according to the institutional standard of care for patients with B cell malignancies in an immunocompromised setting. In the event of febrile reaction, an evaluation for infection should be initiated and the subject managed appropriately with antibiotics, fluids, and other supportive care as medically indicated and determined by the treating physician. Viral and fungal infections should be considered throughout a subject's medical management if fever persists. If a subject develops sepsis or systemic bacteremia following CTX110 infusion, appropriate cultures and medical management should be initiated. Additionally, consideration of CRS should be given in any instances of fever following CTX110 infusion within 30 days post-infusion.

Tumor Lysis Syndrome (TLS)

Subjects receiving CAR T cell therapy are at increased risk of TLS. Subjects should be closely monitored for TLS via laboratory assessments and symptoms from the start of LD chemotherapy until 28 days following CTX110 infusion. All subjects should receive prophylactic allopurinol (or a non-allopurinol alternative, such as febuxostat) and increased oral/IV hydration during screening and before initiation of LD chemotherapy. Prophylaxis can be stopped after 28 days following CTX110 infusion or once the risk of TLS passes.

Sites should monitor and treat TLS as per their institutional standard of care, or according to published guidelines (Cairo and Bishop, (2004) *Br J Haematol*, 127, 3-11). TLS management, including administration of rasburicase, should be instituted promptly when clinically indicated.

Cytokine Release Syndrome (CRS)

CRS is a major toxicity reported with autologous CD19-directed CAR T cell therapy. CRS is due to hyperactivation of the immune system in response to CAR engagement of the target antigen, resulting in multi-cytokine elevation from rapid T cell stimulation and proliferation (Frey et al., (2014) *Blood,* 124, 2296; Maude et al., (2014) *Cancer J,* 20, 119-122). When cytokines are released, a variety of clinical signs and symptoms associated with CRS may occur, including cardiac, gastrointestinal (GI), neurological, respiratory (dyspnea, hypoxia), skin, cardiovascular (hypotension, tachycardia), and constitutional (fever, rigors, sweating, anorexia, headaches, malaise, fatigue, arthralgia, nausea, and vomiting) symptoms, and laboratory (coagulation, renal, and hepatic) abnormalities.

other end organ toxicities should be managed separately with supportive care. Accordingly, in this protocol neurotoxicity will be graded and managed using a different scale (see section entitled "Immune Effector Cell-Associated Neurotoxicity Syndrome (ICANS)"), and end organ toxicity in the context of CRS management refers only to hepatic and renal systems (as in the Penn Grading criteria; (Porter et al., (2018) *J Hematol Oncol,* 11, 35). The sponsor may elect to revise the CRS grading criteria and toxicity management algorithms to reflect the ASBMT consensus proposal based on clinical experience with CTX110 and other CAR T cell therapies.

TABLE 19

Cytokine Release Syndrome Grading and Management Guidance.

| CRS Severity [1] | Tocilizumab | Corticosteroids |
|---|---|---|
| Grade 1<br>Symptoms require symptomatic treatment only (e.g., fever, fatigue, headache, myalgia, malaise). | N/A | N/A |
| Grade 2<br>Symptoms require and respond to moderate intervention. Oxygen requirement <40% FiO$_2$ or hypotension responsive to fluids or low dose of 1 vasopressor or grade 2 organ toxicity.[2] | Administer tocilizumab[3] 8 mg/kg IV over 1 hour (not to exceed 800 mg).<br>Repeat tocilizumab every 8 hours as needed if not responsive to IV fluids or increasing supplemental oxygen.<br>Limit to ≤3 doses in a 24-hour period; maximum total of 4 doses. | Manage per grade 3 if no improvement within 24 hours after starting tocilizumab. |
| Grade 3<br>Symptoms require and respond to aggressive intervention. Oxygen requirement ≥40% FiO$_2$ or hypotension requiring high-dose or multiple vasopressors[4] or grade 3 organ toxicity or grade 4 transaminitis. | Per grade 2. | If no improvement within 24 hours after starting tocilizumab, administer methylprednisolone 1 mg/kg IV twice daily. Continue corticosteroid use until the event is grade ≤1, then taper over 3 days. |
| Grade 4<br>Life-threatening symptoms. Requirements for ventilator support, continuous veno-venous hemodialysis or grade 4 organ toxicity (excluding transaminitis). | Per grade 2.<br>If no response to multiple doses of tocilizumab and steroids, consider using other anti-cytokine therapies (e.g., siltuximab). | Per grade 3. |

CRS: cytokine release syndrome; FiO$_2$: fraction of inspired oxygen; IV: intravenously; N/A: not applicable.
[1]See (Lee et al., (2014) Blood, 124, 188-195).
[2]Refer to entitled "Immune Effector Cell-Associated Neurotoxicity Syndrome (ICANS)" for management of neurologic toxicity. Organ toxicity refers to hepatic and renal systems only.
[3]Refer to tocilizumab prescribing information.
[4]See Table 20 for information on high-dose vasopressors.

The goal of CRS management is to prevent life-threatening sequelae while preserving the potential for the antitumor effects of CTX110. Symptoms usually occur 1 to 14 days after autologous CAR T cell therapy, but the timing of symptom onset has not been fully defined for allogeneic CAR T cells.

CRS should be identified and treated based on clinical presentation and not laboratory cytokine measurements. If CRS is suspected, grading and management should be performed according to the recommendations in Table 19, which are adapted from published guidelines (Lee et al., (2014) *Blood,* 124, 188-195). Since the development of the original Lee CRS grading criteria, physicians using CAR T cell therapies have gained further understanding of the presentation and time course of CRS. The recent American Society for Blood and Marrow Transplantation (ASBMT) consensus criteria (Lee et al., (2018) *Biol Blood Marrow Transplant*) recommend that grading should be based on the presence of fever with hypotension and/or hypoxia, and that

TABLE 20

High-dose Vasopressors.

| Pressor | Dose* |
|---|---|
| Norepinephrine monotherapy | ≥20 µg/min |
| Dopamine monotherapy | ≥10 µg/kg/min |
| Phenylephrine monotherapy | ≥200 µg/min |
| Epinephrine monotherapy | ≥10 µg/min |
| If on vasopressin | Vasopressin + norepinephrine equivalent of ≥10 µg/min** |
| If on combination vasopressors (not vasopressin) | Norepinephrine equivalent of ≥20 µg/min** |

*All doses are required for ≥3 hours.
**VASST Trial vasopressor equivalent equation: norepinephrine equivalent dose = [norepinephrine (µg/min)] + [dopamine (µg/min)/2] + [epinephrine (µg/min)] + [phenylephrine (µg/min)/10]

Throughout the duration of CRS, subjects should be provided with supportive care consisting of antipyretics, IV fluids, and oxygen. Subjects who experience grade 2 CRS (e.g., hypotension, not responsive to fluids, or hypoxia requiring supplemental oxygenation) should be monitored with continuous cardiac telemetry and pulse oximetry. For subjects experiencing grade 3 CRS, consider performing an echocardiogram to assess cardiac function. For grade 3 or 4 CRS, consider intensive care supportive therapy. Intubation for airway protection due to neurotoxicity (e.g., seizure) and not due to hypoxia should not be captured as grade 4 CRS. Similarly, prolonged intubation due to neurotoxicity without other signs of CRS (e.g., hypoxia) is not considered grade 4 CRS. Investigators should always consider the potential of an underlying infection in cases of severe CRS, as the presentation (fever, hypotension, hypoxia) is similar. Resolution of CRS is defined as resolution of fever (temperature ≥38° C.), hypoxia, and hypotension (Lee et al., (2018) *Biol Blood Marrow Transplant*).

Immune Effector Cell-associated Neurotoxicity Syndrome (ICANS)

Neurotoxicity has been observed with autologous CD19-directed CAR T cell therapies. It may occur at the time of CRS, during the resolution of CRS, or following resolution of CRS, and its pathophysiology is unclear. The recent ASBMT consensus further defined neurotoxicity associated with CRS as immune effector cell-associated neurotoxicity syndrome (ICANS), a disorder characterized by a pathologic process involving the CNS following any immune therapy that results in activation or engagement of endogenous or infused T cells and/or other immune effector cells (Lee et al., (2018) *Biol Blood Marrow Transplant*). Signs and symptoms can be progressive and may include aphasia, altered level of consciousness, impairment of cognitive skills, motor weakness, seizures, and cerebral edema. ICANS grading was developed based on CAR T cell-therapy-associated TOXicity (CARTOX) working group criteria used previously in autologous CAR T cell trials (Neelapu et al., (2018) *N Engl J Med*, 377, 2531-2544). ICANS incorporates assessment of level of consciousness, presence/absence of seizures, motor findings, presence/absence of cerebral edema, and overall assessment of neurologic domains by using a modified assessment tool called the ICE (immune effector cell-associated encephalopathy) assessment tool (see Table 21).

Evaluation of any new onset neurotoxicity should include a neurological examination (including ICE assessment tool, Table 22), brain MRI, and examination of the CSF (via lumbar puncture) as clinically indicated. If a brain MRI is not possible, all subjects should receive a non-contrast CT to rule out intracerebral hemorrhage. Electroencephalogram should also be considered as clinically indicated. Endotracheal intubation may be needed for airway protection in severe cases.

Non-sedating, anti-seizure prophylaxis (e.g., levetiracetam) should be considered in all subjects for at least 21 days following CTX110 infusion or upon resolution of neurological symptoms (unless the investigator considers the antiseizure medication to be contributing to the detrimental symptoms). Subjects who experience ICANS grade ≥2 should be monitored with continuous cardiac telemetry and pulse oximetry. For severe or life-threatening neurologic toxicities, intensive care supportive therapy should be provided. Neurology consultation should always be considered. Monitor platelets and for signs of coagulopathy, and transfuse blood products appropriately to diminish risk of intracerebral hemorrhage. Table 21 provides neurotoxicity grading and Table 23 provides management guidance.

For subjects who receive active steroid management for more than 3 days, antifungal and antiviral prophylaxis is recommended to mitigate a risk of severe infection with prolonged steroid use. Consideration for antimicrobial prophylaxis should also be given.

TABLE 21

ICANS Grading.

| Neurotoxicity Domain | Grade 1 | Grade 2 | Grade 3 | Grade 4 |
| --- | --- | --- | --- | --- |
| ICE score [1] | 7-9 | 3-6 | 0-2 | 0 (subject is unarousable and unable to undergo ICE assessment) |
| Depressed level of consciousness [2] | Awakens spontaneously | Awakens to voice | Awakens only to tactile stimulus | Subject is unarousable or requires vigorous or repetitive tactile stimuli to arise; stupor or coma |
| Seizure | N/A | N/A | Any clinical seizure, focal or generalized, that resolves rapidly, or nonconvulsive seizures on EEG that resolve with intervention | Life-threatening prolonged seizure (>5 min) or repetitive clinical or electrical seizures without return to baseline in between |
| Motor findings [3] | N/A | N/A | N/A | Deep focal motor weakness such as hemiparesis or paraparesis |
| Elevated ICP/ cerebral edema | N/A | N/A | Focal/local edema on neuroimaging [4] | Diffuse cerebral edema on neuroimaging, decerebrate or decorticate posturing, cranial nerve VI palsy, papilladema, or Cushing's triad |

CTCAE: Common Terminology Criteria for Adverse Events; EEG: electroencephalogram; ICANS: immune effector cell-associated neurotoxicity syndrome; ICE: immune effector cell-associated encephalopathy (assessment tool); ICP: intracranial pressure; N/A: not applicable.
ICANS grade is determined by the most severe event (ICE score, level of consciousness, seizure, motor findings, raised ICP/cerebral edema) not attributable to any other cause.
[1] A subject with an ICE score of 0 may be classified as grade 3 ICANS if awake with global aphasia, but a subject with an ICE score of 0 may be classified as grade 4 ICANS if unarousable.
[2] Depressed level of consciousness should be attributable to no other cause (e.g., sedating medication).
[3] Tremors and myoclonus associated with immune effector therapies should be graded according to CTCAE v5.0 but do not influence ICANS grading.

TABLE 22

ICE Assessment.

| Domain | Assessment | Maximum Score |
|---|---|---|
| Orientation | Orientation to year, month, city, hospital | 4 points |
| Naming | Name 3 objects (e.g., point to clock, pen, button) | 3 points |
| Following command | Ability to follow commands (e.g., "Show me 2 fingers" or "Close your eyes and stick out your tongue") | 1 point |
| Writing | Ability to write a standard sentence (includes a noun and verb) | 1 point |
| Attention | Ability to count backward from 100 by 10 | 1 point |

ICE score will be reported as the total number of points (0-10) across all assessments.

The ICE assessment will be performed at screening, before administration of CTX110 on Day 1, and on Days 2, 3, 5, 8, and 28. If a subject experiences CNS symptoms, the ICE assessment should continue to be performed approximately every 2 days until resolution of symptoms. To minimize variability, whenever possible the assessment should be performed by the same research staff member who is familiar with or trained in administration of the ICE assessment.

TABLE 23

ICANS Management Guidance.

| Severity | Management |
|---|---|
| Grade 2 | Consider administering dexamethasone 10 mg IV every 6 hours (or equivalent methylprednisolone) unless subject already on equivalent dose of steroids for CRS. Continue dexamethasone use until event is grade ≤1, then taper over 3 days. |
| Grade 3 | Administer dexamethasone 10 mg IV every 6 hours, unless subject already on equivalent dose of steroids for CRS. Continue dexamethasone use until event is grade ≤1, then taper over 3 days. |
| Grade 4 | Administer methylprednisolone 1000 mg IV per day for 3 days; if improves, manage as above. |

CRS: cytokine release syndrome; ICANS: immune effector cell-associated neurotoxicity syndrome; IV: intravenously.

Headache, which may occur in a setting of fever or after chemotherapy, is a nonspecific symptom. Headache alone may not necessarily be a manifestation of ICANS and further evaluation should be performed. Weakness or balance problem resulting from deconditioning and muscle loss are excluded from definition of ICANS. Similarly, intracranial hemorrhage with or without associated edema may occur due to coagulopathies in these subjects and are also excluded from definition of ICANS. These and other neurotoxicities should be captured in accordance with CTCAE v5.0.

B Cell Aplasia

B cell aplasia may occur and will be monitored by following immunoglobulin G blood levels. IV gammaglobulin will be administered for clinically significant hypogammaglobulinemia (systemic infections) according to institutional standard of care.

Hemophagocytic Lymphohistiocytosis (HLH)

HLH has been reported after treatment with autologous CD19-directed CAR T cells (Barrett et al., (2014) *Curr Opin Pediatr,* 26, 43-49; Maude et al., (2014) *N Engl J Med,* 371, 1507-1517; Maude et al., (2015) *Blood,* 125, 4017-4023; Porter et al., (2015) *Sci Transl Med,* 7, 303ra139; Teachey et al., (2013) *Blood,* 121, 5154-5157. HLH is a clinical syndrome that is a result of an inflammatory response following infusion of CAR T cells in which cytokine production from activated T cells leads to excessive macrophage activation. Signs and symptoms of HLH may include fevers, cytopenias, hepatosplenomegaly, hepatic dysfunction with hyperbilirubinemia, coagulopathy with significantly decreased fibrinogen, and marked elevations in ferritin and C-reactive protein (CRP). Neurologic findings have also been observed (Jordan et al., (2011) *Blood,* 118, 4041-4052; La Rosèe, (2015) *Hematology Am Soc Hematol Educ Program,* 190-196.

CRS and HLH may possess similar clinical syndromes with overlapping clinical features and pathophysiology. HLH will likely occur at the time of CRS or as CRS is resolving. HLH should be considered if there are unexplained elevated liver function tests or cytopenias with or without other evidence of CRS. Monitoring of CRP and ferritin may assist with diagnosis and define the clinical course.

If HLH is suspected:
  Frequently monitor coagulation parameters, including fibrinogen. These tests may be done more frequently than indicated in the schedule of assessments, and frequency should be driven based on laboratory findings.
  Fibrinogen should be maintained ≥100 mg/dL to decrease risk of bleeding.
  Coagulopathy should be corrected with blood products.
  Given the overlap with CRS, subjects should also be managed per CRS treatment guidance in Table 19.
Cytopenias
  Grade 3 neutropenia and thrombocytopenia, at times lasting more than 28 days post-infusion, have been reported in subjects treated with autologous CD19-directed CAR T cell products (Kymriah USPI, 2017; Yescarta USPI, 2017). Therefore, subjects receiving CTX110 should be monitored for such toxicities and appropriately supported. Consideration should be given to antimicrobial and antifungal prophylaxis for any subject with prolonged neutropenia.
  G-CSF may be considered in cases of grade 4 neutropenia 21 days post-CTX110 infusion, when the risk of CRS has passed.

Graft Versus Host Disease

GvHD is seen in the setting of allogeneic HSCT and is the result of immunocompetent donor T cells (the graft) recognizing the recipient (the host) as foreign. The subsequent immune response activates donor T cells to attack the recipient to eliminate foreign antigen-bearing cells. GvHD is divided into acute, chronic, and overlap syndromes based on both the time from allogeneic HSCT and clinical manifestations. Signs of acute GvHD may include a maculopapular rash; hyperbilirubinemia with jaundice due to damage to the small bile ducts, leading to cholestasis; nausea, vomiting, and anorexia; and watery or bloody diarrhea and cramping abdominal pain (Zeiser and Blazar, (2017) *N Engl J Med*, 377, 2167-2179.

To support the proposed clinical study, a nonclinical Good Laboratory Practice (GLP)-compliant GvHD and tolerability study was performed in immunocompromised mice at 2 doses that exceed all proposed clinical dose levels by at least 10-fold. Further, due to the specificity of CAR insertion at the TRAC locus, it is highly unlikely for a T cell to be both CAR+ and TCR+. Remaining TCR+ cells are removed during the manufacturing process by immunoaffinity chromatography on an anti-TCR antibody column to achieve <0.5% TCR+ cells in the final product. A dose limit of $7 \times 10^4$ TCR+ cells/kg will be imposed for all dose levels. This limit is lower than the limit of $1 \times 10^5$ TCR+ cells/kg based on published reports on the number of allogeneic cells capable of causing severe GvHD during SCT with haploidentical donors (Bertaina et al., (2014) *Blood*, 124, 822-826. Through this specific editing, purification, and strict product release criteria, the risk of GvHD following CTX110 should be low, although the true incidence is unknown. Subjects should be monitored closely for signs of acute GvHD following infusion of CTX110. The timing of potential symptoms is unknown. However, given that CAR T cell expansion is antigen-driven and will likely occur only in TCR− cells, it is unlikely that the number of TCR+ cells will appreciably increase above the number infused.

Diagnosis and grading of GvHD should be based on published criteria (Harris et al., (2016) *Biol Blood Marrow Transplant*, 22, 4-10), as outlined in Table 24.

TABLE 24

Criteria for Grading Acute GvHD

| Stage | Skin (active erythema only) | Liver (bilirubin mg/dL) | Upper GI | Lower GI (stool output/day) |
|---|---|---|---|---|
| 0 | No active (erythematous) GvHD rash | <2 | No or intermittent nausea, vomiting, or anorexia | <500 ml/day or <3 episodes/day |
| 1 | Maculopapular rash <25% BSA | 2-3 | Persistent nausea, vomiting, or anorexia | 500-999 ml/day or 3-4 episodes/day |
| 2 | Maculopapular rash 25-50% BSA | 3.1-6 | — | 1000-1500 ml/day or 5-7 episodes/day |
| 3 | Maculopapular rash >50% BSA | 6.1-15 | — | >1500 ml/day or >7 episodes/day |
| 4 | Generalized erythroderma (>50% BSA) plus bullous formation and desquamation >5% BSA | >15 | — | Severe abdominal pain with or without ileus, or grossly bloody stool (regardless of stool volume) |

BSA: body surface area; GI: gastrointestinal; GvHD: graft versus host disease.

Overall GvHD grade will be determined based on most severe target organ involvement.

Grade 0: No stage 1-4 of any organ.
Grade 1: Stage 1-2 skin without liver, upper GI, or lower GI involvement.
Grade 2: Stage 3 rash and/or stage 1 liver and/or stage 1 upper GI and/or stage 1 lower GI.
Grade 3: Stage 2-3 liver and/or stage 2-3 lower GI, with stage 0-3 skin and/or stage 0-1 upper GI.
Grade 4: Stage 4 skin, liver, or lower GI involvement, with stage 0-1 upper GI.

Potential confounding factors that may mimic GvHD such as infections and reactions to medications should be ruled out. Skin and/or GI biopsy should be obtained for confirmation before or soon after treatment has been initiated. In instance of liver involvement, liver biopsy should be attempted if clinically feasible. Sample(s) of all biopsies will also be sent to a central laboratory for pathology assessment. Details of sample preparation and shipment are contained in the Laboratory Manual.

Recommendations for management of acute GvHD are outlined in Table 25. To allow for intersubject comparability at the end of the trial, investigators should follow these recommendations except in specific clinical scenarios in which following them could put the subject at risk.

TABLE 25

Acute GvHD Management

| Grade | Management |
|---|---|
| 1 | Skin: Topical steroids or immunosuppressants; if stage 2: prednisone 1 mg/kg (or equivalent dose). |
| 2-4 | Initiate prednisone 2 mg/kg daily (or equivalent dose). IV form of steroid such as methylprednisolone should be considered if there are concerns with malabsorption. Steroid taper may begin after improvement is seen after ≥3 days of steroids. Taper should be 50% decrease of total daily steroid dose every 5 days. GI: In addition to steroids, start anti-diarrheal agents per standard practice. |

GI: gastrointestinal; IV: intravenous.

Decisions to initiate second-line therapy should be made sooner for subjects with more severe GvHD. For example, secondary therapy may be indicated after 3 days with progressive manifestations of GvHD, after 1 week with persistent grade 3 GvHD, or after 2 weeks with persistent grade 2 GvHD. Second-line systemic therapy may be indicated earlier in subjects who cannot tolerate high-dose glucocorticoid treatment (Martin et al., (2012) *Biol Blood Marrow Transplant*, 18, 1150-1163). Choice of secondary therapy and when to initiate will be based on the treating investigator's clinical judgement and local practice.

Management of refractory acute GvHD or chronic GvHD will be per institutional guidelines. Anti-infective prophylaxis measures should be instituted per local guidelines when treating subjects with immunosuppressive agents (including steroids).

Hypotension and Renal Insufficiency

Hypotension and renal insufficiency have been reported with CAR T cell therapy and should be treated with IV administration of normal saline boluses according to institutional practice guidelines. Dialysis should be considered when appropriate.

Study Eligibility

Inclusion Criteria

To be considered eligible to participate in this study, a subject must meet the inclusion criteria listed below (unless indicated as optional):

1. ≥18 years of age and weight >50 kg (optional).
2. Able to understand and comply with protocol-required study procedures and voluntarily sign a written informed consent document.
3. Diagnosed with 1 of the following B cell malignancies:
    Histologically confirmed B cell NHLs: DLBCL NOS, high grade B cell lymphoma with MYC and BCL2 and/or BCL6 rearrangements, transformed FL, or grade 3b FL.
    Confirmation of tumor histology from local pathology lab (archival tissue from last relapse/progression [within 3 months of enrollment] or biopsy during screening).
    At least 1 measurable lesion that is fluorodeoxyglucose positron emission tomography (PET)-positive, as defined by Lugano criteria (score of 4 or 5 on Lugano criteria 5-point scale). Previously irradiated lesions will be considered measurable only if progression is documented following completion of radiation therapy.
4. Refractory or relapsed disease, as evidenced by the following cohort-specific criteria:
    Two or more lines of prior therapy, including an anti-CD20 monoclonal antibody and an anthracycline-containing regimen, and have failed prior autologous hematopoietic stem cell transplantation (HSCT) or ineligible for or refused prior autologous HSCT. Subjects who have received autologous HSCT must have recovered from HSCT-related toxicities.
    For refractory disease, subjects must have progressive disease on last therapy, or have stable disease following at least 2 cycles of therapy with duration of stable disease of up to 6 months.
    For subjects with transformed FL, subjects must have received at least 1 line of chemotherapy for disease after transformation to DLBCL.
5. Eastern Cooperative Oncology Group (ECOG) performance status 0 or 1.
6. Meets criteria to undergo LD chemotherapy and CAR T cell infusion.
7. Adequate organ function:
    Renal: Estimated glomerular filtration rate >50 mL/min/1.73 m$^2$.
    Liver: Aspartate transaminase or alanine transaminase <3× upper limit of normal (ULN); total bilirubin <1.5× ULN (for subjects with Gilbert's syndrome, total bilirubin <2 mg/dL).
    Cardiac: Hemodynamically stable and left ventricle ejection fraction ≥45% by echocardiogram.
    Pulmonary: Oxygen saturation level on room air >91% per pulse oximetry.
8. Female subjects of childbearing potential (postmenarcheal with an intact uterus and at least 1 ovary, who are less than 1 year postmenopausal) must agree to use acceptable method(s) of contraception from enrollment through at least 12 months after CTX110 infusion.
9. Male subjects must agree to use effective contraception from enrollment through at least 12 months after CTX110 infusion.
10. Agree to participate in an additional long-term follow-up study after completion of this study.

Exclusion Criteria

To be eligible for entry into the study, the subject must not meet any of the exclusion criteria listed below:

1. Eligible for and agrees to autologous HSCT.
2. Treatment with the following therapies as described below:
    Prior treatment with any gene therapy or genetically modified cell therapy, including CAR T cells.
    Prior treatment with a CD19-directed antibody, bispecific T cell engager, or antibody-drug conjugate, unless there is confirmed CD19 expression (by immunohistochemistry or flow cytometry) after progression or relapse following most recent CD19-directed treatment.
3. Prior allogeneic HSCT.
4. Known contraindication to cyclophosphamide, fludarabine, or any of the excipients of CTX110 product.
5. Detectable malignant cells from cerebrospinal fluid (CSF) or magnetic resonance imaging (MRI) indicating brain metastases during screening, or a history of central nervous system (CNS) involvement by malignancy (CSF or imaging).
6. History of a seizure disorder, cerebrovascular ischemia/hemorrhage, dementia, cerebellar disease, or any autoimmune disease with CNS involvement.
7. Unstable angina, clinically significant arrhythmia, or myocardial infarction within 6 months prior to screening.
8. Uncontrolled, acute life-threatening bacterial, viral, or fungal infection.
9. Positive for presence of human immunodeficiency virus (HIV) type 1 or 2, or active hepatitis B virus (HBV) or hepatitis C virus (HCV) infection. Subjects with prior history of HBV or HBC infection who have documented undetectable viral load (by quantitative polymerase chain reaction [PCR] or nucleic acid testing) are permitted. Infectious disease testing (HIV-1, HIV-2, HCV antibody and PCR, HBV surface antigen, HBV surface antibody, HBV core antibody) performed within 30 days of signing the informed consent form may be considered for subject eligibility.
10. Previous or concurrent malignancy, except basal cell or squamous cell skin carcinoma, adequately resected and in situ carcinoma of cervix, or a previous malignancy that was completely resected and has been in remission for ≥5 years.
11. Radiation therapy within 14 days of enrollment.
12. Use of systemic antitumor therapy or investigational agent within 14 days or 5 half-lives, whichever is longer, of enrollment. Exceptions are made for 1) prior inhibitory/stimulatory immune checkpoint molecule therapy, which is prohibited within 3 half-lives of enrollment, and 2) rituximab use within 30 days prior to screening is prohibited.
13. Primary immunodeficiency disorder or active autoimmune disease requiring steroids and/or other immunosuppressive therapy.
14. Diagnosis of significant psychiatric disorder or other medical condition that could impede the subject's ability to participate in the study.
15. Women who are pregnant or breastfeeding.

Statistical Methods

Sample Size

The sample size in the dose escalation part of the study will be approximately 6 to 54 subjects, depending on the number of dose levels and cohorts evaluated, and the occurrence of DLTs.

If the study proceeds to cohort expansion, an optimal Simon 2-stage design will be employed. The sample size for each cohort will depend on the assumption of effect size for the specific indication.

For expansion of Cohort A, in the first stage, up to 30 subjects will be enrolled. If 10 or more of the first 30 subjects in the full analysis set achieve an objective response, the study will expand enrollment to include an additional 47 subjects (77 total) in the second stage. A final sample size of 77 subjects will have 90% power ($\alpha=0.05$, 2-sided test) to test for a difference between a ORR of 45% with CTX110 and an ORR of 26%, the estimated ORR to standard salvage therapy in patients with relapsed/refractory DLBCL.

As in Cohort A, upon completion of the dose escalation part of the study, Cohort B may go on to cohort expansion after a protocol amendment.

To date, all subjects that participated in this study have completed Stage 1 (eligibility screening) within 14 days. One subject completed Stage 1 within 2 days. A subject who met the eligibility criteria started lymphodepleting therapy within 24 hours of completing Stage 1. All eligible subjects have completed the screening period (stage 1) and received LD chemotherapy in less than 15 days, with one patient completing screening and starting an LD chemo dose within 72 hrs. Some of the eligible subjects have DLBCL (e.g., NOS, high grade); others have transformed FL and Richter's transformation.

All subjects receiving LD chemotherapy have progressed to receiving the DL1 or DL2 dose of CTX110 within 2-7 days following completion of the LD chemotherapy. Results obtained from these patients to date are summarized below.

Subjects in both DL1 and DL2 doses experienced decreased tumor metabolic activity (FDG uptake on PET scan) and/or decrease in tumor size. A dose dependent response has been observed, including a complete and durable response for >60 days at DL2. None of the treated patients exhibited any DLTs so far. Further, the allogeneic CAR-T cell therapy exhibited desired pharmacokinetic features in the treated human subjects, including CAR-T cell expansion and persistence after infusion. A dose dependent effect has also been observed in both CTX110 expansion and persistence. All subjects in DL2 have exhibited CTX110 expansion and persistence. Up to 90-fold expansion of CTX110 in peripheral blood has been observed in one subject. Further, persistence of CTX110 cells can be detected in DL2 subjects at least 8-10 days following treatment and has been detected up to 28 days post-infusion.

SEQUENCE TABLE

| SEQ ID NO | Description | Sequence |
|---|---|---|
| 1 | TRAC gene-edit | AAGAGCAACAAATCTGACT |
| 2 | TRAC gene-edit | AAGAGCAACAGTGCTGTGCCTGGAGCAACAAATCTGACT AAGAGCAACAAATCTGACT |
| 3 | TRAC gene-edit | AAGAGCAACAGTGCTGGAGCAACAAATCTGACT AAGAGCAACAAATCTGACT |
| 4 | TRAC gene-edit | AAGAGCAACAGTGCCTGGAGCAACAAATCTGACT AAGAGCAACAAATCTGACT |
| 5 | TRAC gene-edit | AAGAGCAACAGTGCTGACTAAGAGCAACAAATCTGACT |
| 6 | TRAC gene-edit | AAGAGCAACAGTGCTGTGGGCCTGGAGCAACAAATCTGACT AAGAGCAACAAATCTGACT |
| 7 | TRAC gene-edit | AAGAGCAACAGTGCTGGCCTGGAGCAACAAATCTGACT AAGAGCAACAAATCTGACT |
| 8 | TRAC gene-edit | AAGAGCAACAGTGCTGTGTGCCTGGAGCAACAAATCTGACT AAGAGCAACAAATCTGACT |
| 9 | B2M gene-edit | CGTGGCCTTAGCTGTGCTCGCGCTACTCTCTCTTTCTGCCT GGAGGCTATCCAGCGTGAGTCTCTCCTACCCTCCCGCT |
| 10 | B2M gene-edit | CGTGGCCTTAGCTGTGCTCGCGCTACTCTCTCTTTCGCCTG GAGGCTATCCAGCGTGAGTCTCTCCTACCCTCCCGCT |
| 11 | B2M gene-edit | CGTGGCCTTAGCTGTGCTCGCGCTACTCTCTCTTTCTGGA GGCTATCCAGCGTGAGTCTCTCCTACCCTCCCGCT |
| 12 | B2M gene-edit | CGTGGCCTTAGCTGTGCTCGCGCTACTCTCTCTTTCTGGAT AGCCTGGAGGCTATCCAGCGTGAGTCTCTCCTACCCTCCC GCT |
| 13 | B2M gene-edit | CGTGGCCTTAGCTGTGCTCGCGCTATCCAGCGTGAGTCTC TCCTACCCTCCCGCT |
| 14 | B2M gene-edit | CGTGGCCTTAGCTGTGCTCGCGCTACTCTCTCTTTCTGTGG CCTGGAGGCTATCCAGCGTGAGTCTCTCCTACCCTCCCGC T |
| 15 | sgRNA | nnnnnnnnnnnnnnnnnnnnguuuuagagcuagaaauagcaaguuaaaauaaggcu aguccguuaucaacuugaaaaaguggcaccgagucggugcuuuu |
| 16 | sgRNA | nnnnnnnnnnnnnnnnnnnnguuuuagagcuagaaauagcaaguuaaaauaaggcu aguccguuaucaacuugaaaaaguggcaccgagucggugc |

-continued

| SEQUENCE TABLE | | |
|---|---|---|
| SEQ ID NO | Description | Sequence |
| 17 | sgRNA | n(17-30)guuuuagagcuagaaauagcaaguuaaaauaaggcuaguccguuauc aacuugaaaaaguggcaccgagucggugcu(1-8) |
| 18 | TRAC sgRNA (TA-1) unmodified | AGAGCAACAGUGCUGUGGCCguuuuagagcuagaaauagcaaguuaaa auaaggcuaguccguuaucaacuugaaaaaguggcaccgagucggugcUUUU |
| 19 | TRAC sgRNA spacer unmodified | AGAGCAACAGUGCUGUGGCC |
| 20 | B2M sgRNA unmodified | GCUACUCUCUCUUUCUGGCCguuuuagagcuagaaauagcaaguuaaa auaaggcuaguccguuaucaacuugaaaaaguggcaccgagucggugcUUUU |
| 21 | B2M sgRNA spacer unmodified | GCUACUCUCUCUUUCUGGCC |
| 22 | TRAC sgRNA (TA-1) modified *: 2'-O-methyl phosphorothioate residue | A*G*A*GCAACAGUGCUGUGGCCguuuuagagcuagaaauagcaagu uaaaauaaggcuaguccguuaucaacuugaaaaaguggcaccgagucggugcU*U* U*U |
| 23 | TRAC sgRNA spacer modified *: 2'-O-methyl phosphorothioate residue | A*G*A*GCAACAGUGCUGUGGCC |
| 24 | B2M sgRNA modified *: 2'-O-methyl phosphorothioate residue | G*C*U*ACUCUCUCUUUCUGGCCguuuuagagcuagaaauagcaagu uaaaauaaggcuaguccguuaucaacuugaaaaaguggcaccgagucggugcU*U* U*U |
| 25 | B2M sgRNA spacer modified *: 2'-O-methyl phosphorothioate residue | G*C*U*ACUCUCUCUUUCUGGCC |
| 26 | TRAC target sequence | AGAGCAACAGTGCTGTGGCC |
| 27 | B2M target sequence | GCTACTCTCTCTTTCTGGCC |
| 28 | TRAC target sequence with (PAM) | AGAGCAACAGTGCTGTGGCC(TGG) |
| 29 | B2M target sequence with (PAM) | GCTACTCTCTCTTTCTGGCC(TGG) |
| 30 | signal peptide | MLLLVTSLLLCELPHPAFLLIP |
| 31 | signal peptide | MALPVTALLLPLALLLHAARP |
| 32 | CD8a transmembrane domain | IYIWAPLAGTCGVLLLSLVITLY |
| 33 | 4-1BB nucleotide sequence | AAACGGGGCAGAAAGAAACTCCTGTATATATTCAAACAA CCATTTATGAGACCAGTACAAACTACTCAAGAGGAAGAT GGCTGTAGCTGCCGATTTCCAGAAGAAGAAGAAGGAGGA TGTGAACTG |
| 34 | 4-1BB amino acid sequence | KRGRKKLLYIFKQPFMRPVQTTQEEDGCSCRFPEEEEGGCEL |
| 35 | CD28 nucleotide sequence | TCAAAGCGGAGTAGGTTGTTGCATTCCGATTACATGAATA TGACTCCTCGCCGGCCTGGGCCGACAAGAAAACATTACC AACCCTATGCCCCCCCACGAGACTTCGCTGCGTACAGGTC C |
| 36 | CD28 amino acid sequence | SKRSRLLHSDYMNMTPRRPGPTRKHYQPYAPPRDFAAYRS |

SEQUENCE TABLE

| SEQ ID NO | Description | Sequence |
|---|---|---|
| 37 | CD3-zeta nucleotide sequence | CGAGTGAAGTTTTCCCGAAGCGCAGACGCTCCGGCATAT<br>CAGCAAGGACAGAATCAGCTGTATAACGAACTGAATTTG<br>GGACGCCGCGAGGAGTATGACGTGCTTGATAAACGCCGG<br>GGGAGAGACCCGGAAATGGGGGGTAAACCCCGAAGAAA<br>GAATCCCCAAGAAGGACTCTACAATGAACTCCAGAAGGA<br>TAAGATGGCGGAGGCCTACTCAGAAATAGGTATGAAGGG<br>CGAACGACGACGGGAAAAGGTCACGATGGCCTCTACCA<br>AGGGTTGAGTACGGCAACCAAAGATACGTACGATGCACT<br>GCATATGCAGGCCCTGCCTCCCAGA |
| 38 | CD3-zeta amino acid sequence | RVKFSRSADAPAYQQGQNQLYNELNLGRREEYDVLDKRRG<br>RDPEMGGKPRRKNPQEGLYNELQKDKMAEAYSEIGMKGER<br>RRGKGHDGLYQGLSTATKDTYDALHMQALPPR |
| 39 | FMC63-28Z (FMC63-CD8[tm]-CD28[co-stimulatory domain]-CD3z) | ATGCTTCTTTTGGTTACGTCTCTGTTGCTTTGCGAACTTCC<br>TCATCCAGCGTTCTTGCTGATCCCCGATATTCAGATGACT<br>CAGACCACCAGTAGCTTGTCTGCCTCACTGGGAGACCGA<br>GTAACAATCTCCTGCAGGGCAAGTCAAGACATTAGCAAA<br>TACCTCAATTGGTACCAGCAGAAGCCCGACGGAACGGTA<br>AAACTCCTCATCTATCATACGTCAAGGTTGCATTCCGGAG<br>TACCGTCACGATTTTCAGGTTCTGGGAGCGGAACTGACTA<br>TTCCTTGACTATTTCAAACCTCGAGCAGGAGGACATTGCG<br>ACATATTTTTGTCAACAAGGTAATACCCTCCCTTACACTT<br>TCGGAGGAGGAACCAAACTCGAAATTACCGGGTCCACCA<br>GTGGCTCTGGGAAGCCTGGCAGTGGAGAAGGTTCCACTA<br>AAGGCGAGGTGAAGCTCCAGGAGAGCGGCCCCGGTCTCG<br>TTGCCCCCAGTCAAAGCCTCTCTGTAACGTGCACAGTGAG<br>TGGTGTATCATTGCCTGATTATGGCGTCTCCTGGATAAGG<br>CAGCCCCCGCGAAAGGGTCTTGAATGGCTTGGGGTAATA<br>TGGGGCTCAGAGACAACGTATTATAACTCCGCTCTCAAA<br>AGTCGCTTGACGATAATAAAAGATAACTCCAAGAGTCAA<br>GTTTTCCTTAAAATGAACAGTTTGCAGACTGACGATACCG<br>CTATATATTATTGTGCTAAACATTATTACTACGGCGGTAG<br>TTACGCGATGGATTATTGGGGGCAGGGGACTTCTGTCAC<br>AGTCAGTAGTGCTGCTGCCTTTGTCCCGGTATTTCTCCCA<br>GCCAAACCGACCACGACTCCCGCCCCGCGCCCTCCGACA<br>CCCGCTCCCACCATCGCCTCTCAACCTCTTAGTCTTCGCC<br>CCGAGGCATGCCGACCCGCCGCCGGGGTGCTGTTCATA<br>CGAGGGGCTTGGACTTCGCTTGTGATATTTACATTTGGGC<br>TCCGTTGGCGGGTACGTGCGGCGTCCTTTTGTTGTCACTC<br>GTTATTACTTTGTATTGTAATCACAGGAATCGCTCAAAGC<br>GGAGTAGGTTGTTGCATTCCGATTACATGAATATGACTCC<br>TCGCCGGCCTGGGCCGACAAGAAAACATTACCAACCCTA<br>TGCCCCCCCACGAGACTTCGCTGCGTACAGGTCCCGAGTG<br>AAGTTTTCCCGAAGCGCAGACGCTCCGGCATATCAGCAA<br>GGACAGAATCAGCTGTATAACGAACTGAATTTGGGACGC<br>CGCGAGGAGTATGACGTGCTTGATAAACGCCGGGGGAGA<br>GACCCGGAAATGGGGGGTAAACCCCGAAGAAGAATCC<br>CCAAGAAGGACTCTACAATGAACTCCAGAAGGATAAGAT<br>GGCGGAGGCCTACTCAGAAATAGGTATGAAGGGCGAACG<br>ACGACGGGAAAAGGTCACGATGGCCTCTACCAAGGGTT<br>GAGTACGGCAACCAAAGATACGTACGATGCACTGCATAT<br>GCAGGCCCTGCCTCCCAGA |
| 40 | FMC63-28Z (FMC63-CD8[tm]-CD28[co-stimulatory domain]-CD3z) Amino Acid | MLLLVTSLLLCELPHPAFLLIPDIQMTQTTSSLSASLGDRVTI<br>SCRASQDISKYLNWYQQKPDGTVKLLIYHTSRLHSGVPSRFS<br>GSGSGTDYSLTISNLEQEDIATYFCQQGNTLPYTFGGGTKLEI<br>TGSTSGSGKPGSGEGSTKGEVKLQESGPGLVAPSQSLSVTCT<br>VSGVSLPDYGVSWIRQPPRKGLEWLGVIVVGSETTYYNSALK<br>SRLTIIKDNSKSQVFLKMNSLQTDDTAIYYCAKHYYYGGSY<br>AMDYWGQGTSVTVSSAAAFVPVFLPAKPTTTPAPRPPTPAP<br>TIASQPLSLRPEACRPAAGGAVHTRGLDFACDIYIVVAPLAGT<br>CGVLLLSLVITLYCNHRNRSKRSLLHSDYMNMTPRRPGPT<br>RKHYQPYAPPRDFAAYRSRVKFSRSADAPAYQQGQNQLYN<br>ELNLGRREEYDVLDKRRGRDPEMGGKPRRKNPQEGLYNEL<br>QKDKMAEAYSEIGMKGERRRGKGHDGLYQGLSTATKDTY<br>DALHMQALPPR |
| 41 | TRAC-LHA (800 bp) | GAGATGTAAGGAGCTGCTGTGACTTGCTCAAGGCCTTAT<br>ATCGAGTAAACGGTAGTGCTGGGGCTTAGACGCAGGTGT<br>TCTGATTTATAGTTCAAAACCTCTATCAATGAGAGAGCAA<br>TCTCCTGGTAATGTGATAGATTTCCCAACTTAATGCCAAC<br>ATACCATAAACCTCCCATTCTGCTAATGCCCAGCCTAAGT<br>TGGGGAGACCACTCCAGATTCCAAGATGTACAGTTTGCTT |

SEQUENCE TABLE

| SEQ ID NO | Description | Sequence |
|---|---|---|
| | | TGCTGGGCCTTTTTCCCATGCCTGCCTTTACTCTGCCAGA |
| | | GTTATATTGCTGGGGTTTTGAAGAAGATCCTATTAAATAA |
| | | AAGAATAAGCAGTATTATTAAGTAGCCCTGCATTTCAGGT |
| | | TTCCTTGAGTGGCAGGCCAGGCCTGGCCGTGAACGTTCAC |
| | | TGAAATCATGGCCTCTTGGCCAAGATTGATAGCTTGTGCC |
| | | TGTCCCTGAGTCCCAGTCCATCACGAGCAGCTGGTTTCTA |
| | | AGATGCTATTTCCCGTATAAAGCATGAGACCGTGACTTGC |
| | | CAGCCCCACAGAGCCCCGCCCTTGTCCATCACTGGCATCT |
| | | GGACTCCAGCCTGGGTTGGGGCAAAGAGGGAAATGAGAT |
| | | CATGTCCTAACCCTGATCCTCTTGTCCCACAGATATCCAG |
| | | AACCCTGACCCTGCCGTGTACCAGCTGAGAGACTCTAAA |
| | | TCCAGTGACAAGTCTGTCTGCCTATTCACCGATTTTGATT |
| | | CTCAAACAAATGTGTCACAAAGTAAGGATTCTGATGTGT |
| | | ATATCACAGACAAAACTGTGCTAGACATGAGGTCTATGG |
| | | ACTTCA |
| 42 | TRAC-RHA (800 bp) | TGGAGCAACAAATCTGACTTTGCATGTGCAAACGCCTTCA |
| | | ACAACAGCATTATTCCAGAAGACACCTTCTTCCCCAGCCC |
| | | AGGTAAGGGCAGCTTTGGTGCCTTCGCAGGCTGTTTCCTT |
| | | GCTTCAGGAATGGCCAGGTTCTGCCCAGAGCTCTGGTCA |
| | | ATGATGTCTAAAACTCCTCTGATTGGTGGTCTCGGCCTTA |
| | | TCCATTGCCACCAAAACCCTCTTTTTACTAAGAAACAGTG |
| | | AGCCTTGTTCTGGCAGTCCAGAGAATGACACGGGAAAAA |
| | | AGCAGATGAAGAGAAGGTGGCAGGAGAGGGCACGTGGC |
| | | CCAGCCTCAGTCTCTCCAACTGAGTTCCTGCCTGCCTGCC |
| | | TTTGCTCAGACTGTTTGCCCCTTACTGCTCTTCTAGGCCTC |
| | | ATTCTAAGCCCCTTCTCCAAGTTGCCTCTCCTTATTTCTCC |
| | | CTGTCTGCCAAAAAATCTTTCCCAGCTCACTAAGTCAGTC |
| | | TCACGCAGTCACTCATTAACCCACCAATCACTGATTGTGC |
| | | CGGCACATGAATGCACCAGGTGTTGAAGTGGAGGAATTA |
| | | AAAAGTCAGATGAGGGGTGTGCCCAGAGGAAGCACCATT |
| | | CTAGTTGGGGGAGCCCATCTGTCAGCTGGGAAAAGTCCA |
| | | AATAACTTCAGATTGGAATGTGTTTTAACTCAGGGTTGAG |
| | | AAAACAGCTACCTTCAGGACAAAAGTCAGGGAAGGGCTC |
| | | TCTGAAGAAATGCTACTTGAAGATACCAGCCCTACCAAG |
| | | GGCAGGGAGAGGACCCTATAGAGGCCTGGGACAGGAGC |
| | | TCAATGAGAAAGG |
| 43 | EF1a | GGCTCCGGTGCCCGTCAGTGGGCAGAGCGCACATCGCCC |
| | | ACAGTCCCCGAGAAGTTGGGGGGAGGGGTCGGCAATTGA |
| | | ACCGGTGCCTAGAGAAGGTGGCGCGGGGTAAACTGGGAA |
| | | AGTGATGTCGTGTACTGGCTCCGCCTTTTTCCCGAGGGTG |
| | | GGGGAGAACCGTATATAAGTGCAGTAGTCGCCGTGAACG |
| | | TTCTTTTTCGCAACGGGTTTGCCGCCAGAACACAGGTAAG |
| | | TGCCGTGTGTGGTTCCCGCGGGCCTGGCCTCTTTACGGGT |
| | | TATGGCCCTTGCGTGCCTTGAATTACTTCCACTGGCTGCA |
| | | GTACGTGATTCTTGATCCCGAGCTTCGGGTTGGAAGTGGG |
| | | TGGGAGAGTTCGAGGCCTTGCGCTTAAGGAGCCCCTTCG |
| | | CCTCGTGCTTGAGTTGAGGCCTGGCCTGGGCGCTGGGGCC |
| | | GCCGCGTGCGAATCTGGTGGCACCTTCGCGCCTGTCTCGC |
| | | TGCTTTCGATAAGTCTCTAGCCATTTAAAATTTTTGATGA |
| | | CCTGCTGCGACGCTTTTTTTCTGGCAAGATAGTCTTGTAA |
| | | ATGCGGGCCAAGATCTGCACACTGGTATTTCGGTTTTTGG |
| | | GGCCGCGGGCGGCGACGGGGCCCGTGCGTCCCAGCGCAC |
| | | ATGTTCGGCGAGGCGGGGCCTGCGAGCGCGGCCACCGAG |
| | | AATCGGACGGGGGTAGTCTCAAGCTGGCCGGCCTGCTCT |
| | | GGTGCCTGGCCTCGCGCCGCCGTGTATCGCCCCGCCCTGG |
| | | GCGGCAAGGCTGGCCCGGTCGGCACCAGTTGCGTGAGCG |
| | | GAAAGATGGCCGCTTCCCGGCCCTGCTGCAGGGAGCTCA |
| | | AAATGGAGGACGCGGCGCTCGGGAGAGCGGGCGGGTGA |
| | | GTCACCCACACAAAGGAAAAGGGCCTTTCCGTCCTCAGC |
| | | CGTCGCTTCATGTGACTCCACGGAGTACCGGGCGCCGTCC |
| | | AGGCACCTCGATTAGTTCTCGAGCTTTTGGAGTACGTCGT |
| | | CTTTAGGTTGGGGGGAGGGGTTTTATGCGATGGAGTTTCC |
| | | CCACACTGAGTGGGTGGAGACTGAAGTTAGGCCAGCTTG |
| | | GCACTTGATGTAATTCTCCTTGGAATTTGCCCTTTTTGAGT |
| | | TTGGATCTTGGTTCATTCTCAAGCCTCAGACAGTGGTTCA |
| | | AAGTTTTTTTCTTCCATTTCAGGTGTCGTGA |
| 44 | GM-CSF signal peptide | ATGCTTCTTTTGGTTACGTCTCTGTTGCTTTGCGAACTTCC TCATCCAGCGTTCTTGCTGATCCCC |
| 45 | GM-CSF signal peptide | MLLLVTSLLLCELPHPAFLLIP |

SEQUENCE TABLE

| SEQ ID NO | Description | Sequence |
|---|---|---|
| 46 | Anti-CD19 scFv | GATATTCAGATGACTCAGACCACCAGTAGCTTGTCTGCCT CACTGGGAGACCGAGTAACAATCTCCTGCAGGGCAAGTC AAGACATTAGCAAATACCTCAATTGGTACCAGCAGAAGC CCGACGGAACGGTAAAACTCCTCATCTATCATACGTCAA GGTTGCATTCCGGAGTACCGTCACGATTTTCAGGTTCTGG GAGCGGAACTGACTATTCCTTGACTATTTCAAACCTCGAG CAGGAGGACATTGCGACATATTTTGTCAACAAGGTAAT ACCCTCCCTTACACTTTCGGAGGAGGAACCAAACTCGAA ATTACCGGGTCCACCAGTGGCTCTGGGAAGCCTGGCAGT GGAGAAGGTTCCACTAAAGGCGAGGTAAGCTCCAGGAG AGCGGCCCCGGTCTCGTTGCCCCCAGTCAAAGCCTCTCTG TAACGTGCACAGTGAGTGGTGTATCATTGCCTGATTATGG CGTCTCCTGGATAAGGCAGCCCCCGCGAAAGGGTCTTGA ATGGCTTGGGGTAATATGGGGCTCAGAGACAACGTATTA TAACTCCGCTCTCAAAAGTCGCTTGACGATAATAAAGA TAACTCCAAGAGTCAAGTTTTCCTTAAAATGAACAGTTTG CAGACTGACGATACCGCTATATATTATTGTGCTAAACATT ATTACTACGGCGGTAGTTACGCGATGGATTATTGGGGGC AGGGGACTTCTGTCACAGTCAGTAGT |
| 47 | CD19 scFv amino acid sequence Linker underlined | DIQMTQTTSSLSASLGDRVTISCRASQDISKYLNWYQQKPD GTVKLLIYHTSRLHSGVPSRFSGSGSGTDYSLTISNLEQEDIA TYFCQQGNTLPYTFGGGTKLEIT<u>GSTSGSGKPGSGEGSTKGE</u> VKLQESGPGLVAPSQSLSVTCTVSGVSLPDYGVSWIRQPPRK GLEWLGVIVVGSETTYYNSALKSRLTIIKDNSKSQVFLKMNS LQTDDTAIYYCAKHYYYGGSYAMDYWGQGTSVTVSS |
| 48 | CD8a extracellular + CD8a transmembrane + 5' Linker (underlined) | <u>GCTGCTGCC</u>TTTGTCCCGGTATTTCTCCCAGCCAAACCGA CCACGACTCCCGCCCCGCCCCTCCGACACCCGCTCCCAC CATCGCCTCTCAACCTCTTAGTCTTCGCCCCGAGGCATGC CGACCCGCCGCCGGGGGTGCTGTTCATACGAGGGGCTTG GACTTCGCTTGTGATATTTACATTTGGGCTCCGTTGGCGG GTACGTGCGGCGTCCTTTTGTTGTCACTCGTTATTACTTTG TATTGTAATCACAGGAATCGC |
| 49 | CD8a extracellular + CD8a transmembrane (without linker) | TTTGTCCCGGTATTTCTCCCAGCCAAACCGACCACGACTC CCGCCCCGCCCCTCCGACACCCGCTCCCACCATCGCCTC TCAACCTCTTAGTCTTCGCCCCGAGGCATGCCGACCCGCC GCCGGGGGTGCTGTTCATACGAGGGGCTTGGACTTCGCTT GTGATATTTACATTTGGGCTCCGTTGGCGGGTACGTGCGG CGTCCTTTTGTTGTCACTCGTTATTACTTTGTATTGTAATC ACAGGAATCGC |
| 50 | CD8a extracellular + CD8a transmembrane | FVPVFLPAKPTTTPAPRPPTPAPTIASQPLSLRPEACRPAAGG AVHTRGLDFACDIYIVVAPLAGTCGVLLLSLVITLYCNHRNR |
| 51 | CD19 VH | EVKLQESGPGLVAPSQSLSVTCTVSGVSLPDYGVSWIRQPPR KGLEWLGVIWGSETTYYNSALKSRLTIIKDNSKSQVFLKMN SLQTDDTAIYYCAKHYYYGGSYAMDYWGQGTSVTVSS |
| 52 | CD19 VL | DIQMTQTTSSLSASLGDRVTISCRASQDISKYLNWYQQKPD GTVKLLIYHTSRLHSGVPSRFSGSGSGTDYSLTISNLEQEDIA TYFCQQGNTLPYTFGGGTKLEIT |
| 53 | CD19 linker | GSTSGSGKPGSGEGSTKG |
| 54 | LHA to RHA | GAGATGTAAGGAGCTGCTGTGACTTGCTCAAGGCCTTAT ATCGAGTAAACGGTAGTGCTGGGGCTTAGACGCAGGTGT TCTGATTTATAGTTCAAAACCTCTATCAATGAGAGAGCAA TCTCCTGGTAATGTGATAGATTTCCCAACTTAATGCCAAC ATACCATAAACCTCCCATTCTGCTAATGCCCAGCCTAAGT TGGGGAGACCACTCCAGATTCCAAGATGTACAGTTTGCTT TGCTGGGCCTTTTTCCCATGCCTGCCTTTACTCTGCCAGA GTTATATTGCTGGGGTTTTGAAGAAGATCCTATTAAATAA AAGAATAAGCAGTATTATTAAGTAGCCCTGCATTTCAGGT TTCCTTGAGTGGCAGGCCAGGCCTGGCCGTGAACGTTCAC TGAAATCATGGCCTCTTGGCCAAGATTGATAGCTTGTGCC TGTCCCTGAGTCCCAGTCCATCACGAGCAGCTGGTTTCTA AGATGCTATTTCCCGTATAAAGCATGAGACCGTGACTTGC CAGCCCCACAGAGCCCCGCCCTTGTCCATCACTGGCATCT GGACTCCAGCCTGGGTTGGGGCAAAGAGGGAAATGAGAT CATGTCCTAACCCTGATCCTCTTGTCCCACAGATATCCAG AACCCTGACCCTGCCGTGTACCAGCTGAGAGACTCTAAA TCCAGTGACAAGTCTGTCTGCCTATTCACCGATTTTGATT |

SEQUENCE TABLE

| SEQ ID NO | Description | Sequence |
|---|---|---|
| | | CTCAAACAAATGTGTCACAAAGTAAGGATTCTGATGTGT |
| | | ATATCACAGACAAAACTGTGCTAGACATGAGGTCTATGG |
| | | ACTTCAGGCTCCGGTGCCCGTCAGTGGGCAGAGCGCACA |
| | | TCGCCCACAGTCCCCGAGAAGTTGGGGGGAGGGGTCGGC |
| | | AATTGAACCGGTGCCTAGAGAAGGTGGCGCGGGGTAAAC |
| | | TGGGAAAGTGATGTCGTGTACTGGCTCCGCCTTTTTCCCG |
| | | AGGGTGGGGGAGAACCGTATATAAGTGCAGTAGTCGCCG |
| | | TGAACGTTCTTTTTCGCAACGGGTTTGCCGCCAGAACACA |
| | | GGTAAGTGCCGTGTGTGGTTCCCGCGGGCCTGGCCTCTTT |
| | | ACGGGTTATGGCCCTTGCGTGCCTTGAATTACTTCCACTG |
| | | GCTGCAGTACGTGATTCTTGATCCCGAGCTTCGGGTTGGA |
| | | AGTGGGTGGGAGAGTTCGAGGCCTTGCGCTTAAGGAGCC |
| | | CCTTCGCCTCGTGCTTGAGTTGAGGCCTGGCCTGGGCGCT |
| | | GGGGCCGCCGCGTGCGAATCTGGTGGCACCTTCGCGCCT |
| | | GTCTCGCTGCTTTCGATAAGTCTCTAGCCATTTAAAATTTT |
| | | TGATGACCTGCTGCGACGCTTTTTTTCTGGCAAGATAGTC |
| | | TTGTAAATGCGGGCCAAGATCTGCACACTGGTATTTCGGT |
| | | TTTTGGGGCCGCGGGCGGCGACGGGGCCCGTGCGTCCCA |
| | | GCGCACATGTTCGGCGAGGCGGGGCCTGCGAGCGCGGCC |
| | | ACCGAGAATCGGACGGGGGTAGTCTCAAGCTGGCCGGCC |
| | | TGCTCTGGTGCCTGGCCTCGCGCCGCCGTGTATCGCCCCG |
| | | CCCTGGGCGGCAAGGCTGGCCCGGTCGGCACCAGTTGCG |
| | | TGAGCGGAAAGATGGCCGCTTCCCGGCCCTGCTGCAGGG |
| | | AGCTCAAAATGGAGGACGCGGCGCTCGGGAGAGCGGGC |
| | | GGGTGAGTCACCCACACAAAGGAAAAGGGCCTTTCCGTC |
| | | CTCAGCCGTCGCTTCATGTGACTCCACGGAGTACCGGGCG |
| | | CCGTCCAGGCACCTCGATTAGTTCTCGAGCTTTTGGAGTA |
| | | CGTCGTCTTTAGGTTGGGGGGAGGGGTTTTATGCGATGGA |
| | | GTTTCCCCACACTGAGTGGGTGGAGACTGAAGTTAGGCC |
| | | AGCTTGGCACTTGATGTAATTCTCCTTGGAATTTGCCCTTT |
| | | TTGAGTTTGGATCTTGGTTCATTCTCAAGCCTCAGACAGT |
| | | GGTTCAAAGTTTTTTTCTTCCATTTCAGGTGTCGTGACCAC |
| | | CATGCTTCTTTTGGTTACGTCTCTGTTGCTTTGCGAACTTC |
| | | CTCATCCAGCGTTCTTGCTGATCCCCGATATTCAGATGAC |
| | | TCAGACCACCAGTAGCTTGTCTGCCTCACTGGGAGACCG |
| | | AGTAACAATCTCCTGCAGGGCAAGTCAAGACATTAGCAA |
| | | ATACCTCAATTGGTACCAGCAGAAGCCCGACGGAACGGT |
| | | AAAACTCCTCATCTATCATACGTCAAGGTTGCATTCCGGA |
| | | GTACCGTCACGATTTTCAGGTTCTGGGAGCGGAACTGACT |
| | | ATTCCTTGACTATTTCAAACCTCGAGCAGGAGGACATTGC |
| | | GACATATTTTTGTCAACAAGGTAATACCCTCCCTTACACT |
| | | TTCGGAGGAGGAACCAAACTCGAAATTACCGGGTCCACC |
| | | AGTGGCTCTGGGAAGCCTGGCAGTGGAGAAGGTTCCACT |
| | | AAAGGCGAGGTGAAGCTCCAGGAGAGCGGCCCCGGTCTC |
| | | GTTGCCCCCAGTCAAAGCCTCTCTGTAACGTGCACAGTGA |
| | | GTGGTGTATCATTGCCTGATTATGGCGTCTCCTGGATAAG |
| | | GCAGCCCCCGCGAAAGGGTCTTGAATGGCTTGGGGTAAT |
| | | ATGGGGCTCAGAGACAACGTATTATAACTCCGCTCTCAA |
| | | AAGTCGCTTGACGATAATAAAAGATAACTCCAAGAGTCA |
| | | AGTTTTCCTTAAAATGAACAGTTTGCAGACTGACGATACC |
| | | GCTATATATTATTGTGCTAAACATTATTACTACGGCGGTA |
| | | GTTACGCGATGGATTATTGGGGGCAGGGGACTTCTGTCA |
| | | CAGTCAGTAGTGCTGCTGCCTTTGTCCCGGTATTTCTCCC |
| | | AGCCAAACCGACCACGACTCCCGCCCCGCGCCCTCCGAC |
| | | ACCCGCTCCCACCATCGCCTCTCAACCTCTTAGTCTTCGC |
| | | CCCGAGGCATGCCGACCCGCCGCCGGGGGTGCTGTTCAT |
| | | ACGAGGGGCTTGGACTTCGCTTGTGATATTTACATTTGGG |
| | | CTCCGTTGGCGGGTACGTGCGGCGTCCTTTTGTTGTCACT |
| | | CGTTATTACTTTGTATTGTAATCACAGGAATCGCTCAAAG |
| | | CGGAGTAGGTTGTTGCATTCCGATTACATGAATATGACTC |
| | | CTCGCCGGCCTGGGCCGACAAGAAAACATTACCAACCCT |
| | | ATGCCCCCCACGAGACTTCGCTGCGTACAGGTCCCGAGT |
| | | GAAGTTTTCCCGAAGCGCAGACGCTCCGGCATATCAGCA |
| | | AGGACAGAATCAGCTGTATAACGAACTGAATTTGGGACG |
| | | CCGCGAGGAGTATGACGTGCTTGATAAACGCCGGGGGAG |
| | | AGACCCGGAAATGGGGGGTAAACCCCGAAGAAAGAATC |
| | | CCCAAGAAGGACTCTACAATGAACTCCAGAAGGATAAGA |
| | | TGGCGGAGGCCTACTCAGAAATAGGTATGAAGGGCGAAC |
| | | GACGACGGGGAAAAGGTCACGATGGCCTCTACCAAGGGT |
| | | TGAGTACGGCAACCAAAGATACGTACGATGCACTGCATA |
| | | TGCAGGCCCTGCCTCCCAGATAATAATAAAATCGCTATCC |
| | | ATCGAAGATGGATGTGTGTTGGTTTTTTGTGTGTGGAGCA |
| | | ACAAATCTGACTTTGCATGTGCAAACGCCTTCAACAACA |
| | | GCATTATTCCAGAAGACACCTTCTTCCCCAGCCCAGGTAA |

| SEQ ID NO | Description | Sequence |
|---|---|---|
| | | GGGCAGCTTTGGTGCCTTCGCAGGCTGTTTCCTTGCTTCA<br>GGAATGGCCAGGTTCTGCCCAGAGCTCTGGTCAATGATG<br>TCTAAAACTCCTCTGATTGGTGGTCTCGGCCTTATCCATT<br>GCCACCAAAACCCTCTTTTTACTAAGAAACAGTGAGCCTT<br>GTTCTGGCAGTCCAGAGAATGACACGGGAAAAAAGCAGA<br>TGAAGAGAAGGTGGCAGGAGAGGGCACGTGGCCCAGCC<br>TCAGTCTCTCCAACTGAGTTCCTGCCTGCCTGCCTTTGCTC<br>AGACTGTTTGCCCCTTACTGCTCTTCTAGGCCTCATTCTAA<br>GCCCCTTCTCCAAGTTGCCTCTCCTTATTTCTCCCTGTCTG<br>CCAAAAAATCTTTCCCAGCTCACTAAGTCAGTCTCACGCA<br>GTCACTCATTAACCCACCAATCACTGATTGTGCCGGCACA<br>TGAATGCACCAGGTGTTGAAGTGGAGGAATTAAAAAGTC<br>AGATGAGGGGTGTGCCCAGAGGAAGCACCATTCTAGTTG<br>GGGGAGCCCATCTGTCAGCTGGGAAAAGTCCAAATAACT<br>TCAGATTGGAATGTGTTTTAACTCAGGGTTGAGAAAACA<br>GCTACCTTCAGGACAAAAGTCAGGGAAGGGCTCTCTGAA<br>GAAATGCTACTTGAAGATACCAGCCCTACCAAGGGCAGG<br>GAGAGGACCCTATAGAGGCCTGGGACAGGAGCTCAATGA<br>GAAAGG |
| 55 | spCas9 | MDKKYSIGLDIGTNSVGWAVITDEYKVPSKKFKVLGNTDR<br>HSIKKNLIGALLFDSGETAEATRLKRTARRRYTRRKNRICYL<br>QEIFSNEMAKVDDSFFHRLEESFLVEEDKKHERHPIFGNIVD<br>EVAYHEKYPTIYHLRKKLVDSTDKADLRLIYLALAHMIKFR<br>GHFLIEGDLNPDNSDVDKLFIQLVQTYNQLFEENPINASGVD<br>AKAILSARLSKSRRLENLIAQLPGEKKNGLFGNLIALSLGLTP<br>NFKSNFDLAEDAKLQLSKDTYDDDLDNLLAQIGDQYADLF<br>LAAKNLSDAILLSDILRVNTEITKAPLSASMIKRYDEHHQDL<br>TLLKALVRQQLPEKYKEIFFDQSKNGYAGYIDGGASQEEFY<br>KFIKPILEKMDGTEELLVKLNREDLLRKQRTFDNGSIPHQIHL<br>GELHAILRRQEDFYPFLKDNREKIEKILTFRIPYYVGPLARGN<br>SRFAWMTRKSEETITPWNFEEVVDKGASAQSFIERMTNFDK<br>NLPNEKVLPKHSLLYEYFTVYNELTKVKYVTEGMRKPAFLS<br>GEQKKAIVDLLFKTNRKVTVKQLKEDYFKKIECFDSVEISGV<br>EDRFNASLGTYHDLLKIIKDKDFLDNEENEDILEDIVLTLTLF<br>EDREMIEERLKTYAHLFDDKVMKQLKRRRYTGWGRLSRKL<br>INGIRDKQSGKTILDFLKSDGFANRNFMQLIHDDSLTFKEDIQ<br>KAQVSGQGDSLHEHIANLAGSPAIKKGILQTVKVVDELVKV<br>MGRHKPENIVIEMARENQTTQKGQKNSRERMKRIEEGIKEL<br>GSQILKEHPVENTQLQNEKLYLYYLQNGRDMYVDQELDIN<br>RLSDYDVDHIVPQSFLKDDSIDNKVLTRSDKNRGKSDNVPS<br>EEVVKKMKNYWRQLLNAKLITQRKFDNLTKAERGGLSELD<br>KAGFTKRQLVETRQITKHVAQILDSRMNTKYDENDKLIREV<br>KVITLKSKLVSDFRKDFQFYKVREINNYHHAHDAYLNAVV<br>GTALIKKYPKLESEFVYGDYKVYDVRKMIAKSEQEIGKATA<br>KYFFYSNIMNFFKTEITLANGEIRKRPLIETNGETGEIVWDKG<br>RDFATVRKVLSMPQVNIVKKTEVQTGGFSKESILPKRNSDK<br>LIARKKDWDPKKYGGFDSPTVAYSVLVVAKVEKGKSKKLK<br>SVKELLGITIMERSSFEKNPIDFLEAKGYKEVKKDLIIKLPKY<br>SLFELENGRKRMLASAGELQKGNELALPSKYVNFLYLASHY<br>EKLKGSPEDNEQKQLFVEQHKHYLDEIIEQISEFSKRVILADA<br>NLDKVLSAYNKHRDKPIREQAENIIHLFTLTNLGAPAAFKYF<br>DTTIDRKRYTSTKEVLDATLIHQSITGLYETRIDLSQLGGD |
| 56 | rAAV | CCTGCAGGCAGCTGCGCGCTCGCTCGCTCACTGAGGCCG<br>CCCGGGCGTCGGGCGACCTTTGGTCGCCCGGCCTCAGTG<br>AGCGAGCGAGCGCGCAGAGAGGGAGTGGCCAACTCCATC<br>ACTAGGGGTTCCTGCGGCCGCACGCGTGAGATGTAAGGA<br>GCTGCTGTGACTTGCTCAAGGCCTTATATCGAGTAAACGG<br>TAGTGCTGGGGCTTAGACGCAGGTGTTCTGATTTATAGTT<br>CAAAACCTCTATCAATGAGAGAGCAATCTCCTGGTAATG<br>TGATAGATTTCCCAACTTAATGCCAACATACCATAAACCT<br>CCCATTCTGCTAATGCCCAGCCTAAGTTGGGGAGACCACT<br>CCAGATTCCAAGATGTACAGTTTGCTTTGCTGGGCCTTTT<br>TCCCATGCCTGCCTTTACTCTGCCAGAGTTATATTGCTGG<br>GGTTTTGAAGAAGATCCTATTAAATAAAAGAATAAGCAG<br>TATTATTAAGTAGCCCTGCATTTCAGGTTTCCTTGAGTGG<br>CAGGCCAGGCCTGGCCGTGAACGTTCACTGAAATCATGG<br>CCTCTTGGCCAAGATTGATAGCTTGTGCCTGTCCCTGAGT<br>CCCAGTCCATCACGAGCAGCTGGTTTCTAAGATGCTATTT<br>CCCGTATAAAGCATGAGACCGTGACTTGCCAGCCCCACA<br>GAGCCCCGCCCTTGTCCATCACTGGCATCTGGACTCCAGC<br>CTGGGTTGGGGCAAAGAGGGAAATGAGATCATGTCCTAA<br>CCCTGATCCTCTTGTCCCACAGATATCCAGAACCCTGACC |

SEQUENCE TABLE

| SEQ ID NO | Description | Sequence |
|---|---|---|
| | | CTGCCGTGTACCAGCTGAGAGACTCTAAATCCAGTGACA |
| | | AGTCTGTCTGCCTATTCACCGATTTTGATTCTCAAACAAA |
| | | TGTGTCACAAAGTAAGGATTCTGATGTGTATATCACAGAC |
| | | AAAACTGTGCTAGACATGAGGTCTATGGACTTCAGGCTC |
| | | CGGTGCCCGTCAGTGGGCAGAGCGCACATCGCCCACAGT |
| | | CCCCGAGAAGTTGGGGGAGGGGTCGGCAATTGAACCGG |
| | | TGCCTAGAGAAGGTGGCGCGGGGTAAACTGGGAAAGTGA |
| | | TGTCGTGTACTGGCTCCGCCTTTTTCCCGAGGGTGGGGGA |
| | | GAACCGTATATAAGTGCAGTAGTCGCCGTGAACGTTCTTT |
| | | TTCGCAACGGGTTTGCCGCCAGAACACAGGTAAGTGCCG |
| | | TGTGTGGTTCCCGCGGGCCTGGCCTCTTTACGGGTTATGG |
| | | CCCTTGCGTGCCTTGAATTACTTCCACTGGCTGCAGTACG |
| | | TGATTCTTGATCCCGAGCTTCGGGTTGGAAGTGGGTGGGA |
| | | GAGTTCGAGGCCTTGCGCTTAAGGAGCCCCTTCGCCTCGT |
| | | GCTTGAGTTGAGGCCTGGCCTGGGCGCTGGGGCCGCCGC |
| | | GTGCGAATCTGGTGGCACCTTCGCGCCTGTCTCGCTGCTT |
| | | TCGATAAGTCTCTAGCCATTTAAAATTTTTGATGACCTGC |
| | | TGCGACGCTTTTTTTCTGGCAAGATAGTCTTGTAAATGCG |
| | | GGCCAAGATCTGCACACTGGTATTTCGGTTTTTGGGGCCG |
| | | CGGGCGGCGACGGGCCCGTGCGTCCCAGCGCACATGTT |
| | | CGGCGAGGCGGGGCCTGCGAGCGCGGCCACCGAGAATCG |
| | | GACGGGGGTAGTCTCAAGCTGGCCGGCCTGCTCTGGTGC |
| | | CTGGCCTCGCGCCGCCGTGTATCGCCCCGCCCTGGGCGGC |
| | | AAGGCTGGCCCGGTCGGCACCAGTTGCGTGAGCGGAAAG |
| | | ATGGCCGCTTCCCGGCCCTGCTGCAGGGAGCTCAAAATG |
| | | GAGGACGCGGCGCTCGGGAGAGCGGGCGGGTGAGTCAC |
| | | CCACACAAAGGAAAAGGGCCTTTCCGTCCTCAGCCGTCG |
| | | CTTCATGTGACTCCACGGAGTACCGGGCGCCGTCCAGGC |
| | | ACCTCGATTAGTTCTCGAGCTTTTGGAGTACGTCGTCTTT |
| | | AGGTTGGGGGGAGGGGTTTTATGCGATGGAGTTTCCCCA |
| | | CACTGAGTGGGTGGAGACTGAAGTTAGGCCAGCTTGGCA |
| | | CTTGATGTAATTCTCCTTGGAATTTGCCCTTTTTGAGTTTG |
| | | GATCTTGGTTCATTCTCAAGCCTCAGACAGTGGTTCAAAG |
| | | TTTTTTTCTTCCATTTCAGGTGTCGTGACCACCATGCTTCT |
| | | TTTGGTTACGTCTCTGTTGCTTTGCGAACTTCCTCATCCAG |
| | | CGTTCTTGCTGATCCCCGATATTCAGATGACTCAGACCAC |
| | | CAGTAGCTTGTCTGCCTCACTGGGAGACCGAGTAACAAT |
| | | CTCCTGCAGGGCAAGTCAAGACATTAGCAAATACCTCAA |
| | | TTGGTACCAGCAGAAGCCCGACGGAACGGTAAAACTCCT |
| | | CATCTATCATACGTCAAGGTTGCATTCCGGAGTACCGTCA |
| | | CGATTTTCAGGTTCTGGGAGCGGAACTGACTATTCCTTGA |
| | | CTATTTCAAACCTCGAGCAGGAGGACATTGCGACATATTT |
| | | TTGTCAACAAGGTAATACCCTCCCTTACACTTTCGGAGGA |
| | | GGAACCAAACTCGAAATTACCGGGTCCACCAGTGGCTCT |
| | | GGGAAGCCTGGCAGTGGAGAAGGTTCCACTAAAGGCGAG |
| | | GTGAAGCTCCAGGAGAGCGGCCCCGGTCTCGTTGCCCCC |
| | | AGTCAAAGCCTCTCTGTAACGTGCACAGTGAGTGGTGTAT |
| | | CATTGCCTGATTATGGCGTCTCCTGGATAAGGCAGCCCCC |
| | | GCGAAAGGGTCTTGAATGGCTTGGGGTAATATGGGGCTC |
| | | AGAGACAACGTATTATAACTCCGCTCTCAAAAGTCGCTTG |
| | | ACGATAATAAAAGATAACTCCAAGAGTCAAGTTTTCCTT |
| | | AAAATGAACAGTTTGCAGACTGACGATACCGCTATATAT |
| | | TATTGTGCTAAACATTATTACTACGGCGGTAGTTACGCGA |
| | | TGGATTATTGGGGCAGGGGACTTCTGTCACAGTCAGTA |
| | | GTGCTGCTGCCTTTGTCCCGGTATTTCTCCCAGCCAAACC |
| | | GACCACGACTCCCGCCCCGCGCCCTCCGACACCCGCTCCC |
| | | ACCATCGCCTCTCAACCTCTTAGTCTTCGCCCCGAGGCAT |
| | | GCCGACCCGCCGCCGGGGGTGCTGTTCATACGAGGGGCT |
| | | TGGACTTCGCTTGTGATATTTACATTTGGGCTCCGTTGGC |
| | | GGGTACGTGCGGCGTCCTTTTGTTGTCACTCGTTATTACTT |
| | | TGTATTGTAATCACAGGAATCGCTCAAAGCGGAGTAGGT |
| | | TGTTGCATTCCGATTACATGAATATGACTCCTCGCCGGCC |
| | | TGGGCCGACAAGAAAACATTACCAACCCTATGCCCCCCC |
| | | ACGAGACTTCGCTGCGTACAGGTCCCGAGTGAAGTTTTCC |
| | | CGAAGCGCAGACGCTCCGGCATATCAGCAAGGACAGAAT |
| | | CAGCTGTATAACGAACTGAATTTGGGACGCCGCGAGGAG |
| | | TATGACGTGCTTGATAAACGCCGGGGAGAGACCCGGAA |
| | | ATGGGGGGTAAACCCCGAAGAAGAATCCCCAAGAAGG |
| | | ACTCTACAATGAACTCCAGAAGGATAAGATGGCGGAGGC |
| | | CTACTCAGAAATAGGTATGAAGGGCGAACGACGACGGGG |
| | | AAAAGGTCACGATGGCCTCTACCAAGGGTTGAGTACGGC |
| | | AACCAAAGATACGTACGATGCACTGCATATGCAGGCCCT |
| | | GCCTCCCAGATAATAATAAAATCGCTATCCATCGAAGAT |
| | | GGATGTGTGTTGGTTTTTTGTGTGTGGAGCAACAAATCTG |

SEQUENCE TABLE

| SEQ ID NO | Description | Sequence |
|---|---|---|
| | | ACTTTGCATGTGCAAACGCCTTCAACAACAGCATTATTCC |
| | | AGAAGACACCTTCTTCCCCAGCCCAGGTAAGGGCAGCTT |
| | | TGGTGCCTTCGCAGGCTGTTTCCTTGCTTCAGGAATGGCC |
| | | AGGTTCTGCCCAGAGCTCTGGTCAATGATGTCTAAAACTC |
| | | CTCTGATTGGTGGTCTCGGCCTTATCCATTGCCACCAAAA |
| | | CCCTCTTTTTACTAAGAAACAGTGAGCCTTGTTCTGGCAG |
| | | TCCAGAGAATGACACGGGAAAAAAGCAGATGAAGAGAA |
| | | GGTGGCAGGAGAGGGCACGTGGCCCAGCCTCAGTCTCTC |
| | | CAACTGAGTTCCTGCCTGCCTGCCTTTGCTCAGACTGTTT |
| | | GCCCCTTACTGCTCTTCTAGGCCTCATTCTAAGCCCCTTCT |
| | | CCAAGTTGCCTCTCCTTATTTCTCCCTGTCTGCCAAAAAA |
| | | TCTTTCCCAGCTCACTAAGTCAGTCTCACGCAGTCACTCA |
| | | TTAACCCACCAATCACTGATTGTGCCGGCACATGAATGCA |
| | | CCAGGTGTTGAAGTGGAGGAATTAAAAAGTCAGATGAGG |
| | | GGTGTGCCCAGAGGAAGCACCATTCTAGTTGGGGGAGCC |
| | | CATCTGTCAGCTGGGAAAAGTCCAAATAACTTCAGATTG |
| | | GAATGTGTTTTAACTCAGGGTTGAGAAAACAGCTACCTTC |
| | | AGGACAAAAGTCAGGGAAGGGCTCTCTGAAGAAATGCTA |
| | | CTTGAAGATACCAGCCCTACCAAGGGCAGGGAGAGGACC |
| | | CTATAGAGGCCTGGGACAGGAGCTCAATGAGAAAGGTAA |
| | | CCACGTGCGGACCGAGGCTGCAGCGTCGTCCTCCCTAGG |
| | | AACCCCTAGTGATGGAGTTGGCCACTCCCTCTCTGCGCGC |
| | | TCGCTCGCTCACTGAGGCCGGGCGACCAAAGGTCGCCCG |
| | | ACGCCCGGGCTTTGCCCGGGCGGCCTCAGTGAGCGAGCG |
| | | AGCGCGCAGCTGCCTGCAGG |

\* indicates a nucleotide with a 2'-O-methyl phosphorothioate modification.
"n" refers to the spacer sequence at the 5' end.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

What is claimed is:

1. A method for treating a B-cell malignancy in a human patient, the method comprising:
   (i) subjecting the human patient having a B-cell malignancy to a lymphodepletion treatment; and
   (ii) administering to the human patient a population of genetically engineered primary T cells after step (i), wherein the genetically engineered T cells comprise:
      (a) a disrupted T cell receptor alpha constant (TRAC) gene comprising a deletion of the nucleotide sequence of SEQ ID NO: 26;
      (b) a nucleic acid coding for a chimeric antigen receptor (CAR) that binds CD19, wherein the CAR comprises an anti-CD19 single chain variable fragment (scFv) that comprises a heavy chain variable region set forth in SEQ ID NO: 51, and a light chain variable region set forth in SEQ ID NO: 52, and wherein the nucleic acid is inserted in the disrupted TRAC gene, and
      (c) a disrupted beta 2-microglobulin (β2M) gene;
   wherein the population of genetically engineered primary T cells is administered to the human patient at a dose of about $1\times10^7$ to about $1\times10^9$ CAR$^+$ T cells; and
   wherein the population of genetically engineered primary T cells is allogeneic to the human patient.

2. The method of claim 1, wherein the disrupted TRAC gene comprises the deletion of SEQ ID NO: 26, which is replaced by the nucleic acid encoding the CAR.

3. The method of claim 1, wherein the lymphodepletion treatment in step (i) comprises co-administration to the human patient fludarabine at about 30 mg/m$^2$ and cyclophosphamide at about 500-750 mg/m$^2$ per day for three days.

4. The method of claim 3, wherein the lymphodepletion treatment in step (i) comprises co-administration to the human patient fludarabine at about 30 mg/m$^2$ and cyclophosphamide at about 500 mg/m$^2$ per day for three days, or fludarabine at about 30 mg/m$^2$ and cyclophosphamide at about 750 mg/m$^2$ per day for three days.

5. The method of claim 1, wherein the population of genetically engineered primary T cells is administered to the human patient at a dose of about 1×10⁷, about 3×10⁷, about 1×10⁸, about 3×10⁸, or about 1×10⁹ CAR⁺ T cells.

6. The method of claim 1, wherein step (i) is performed about 2-7 days prior to step (ii).

7. The method of claim 1, further comprising (iii) monitoring the human patient for development of acute toxicity after step (ii); and (iv) managing the acute toxicity if occurs; wherein the acute toxicity comprises tumor lysis syndrome (TLS), cytokine release syndrome (CRS), immune effector cell-associated neurotoxicity syndrome (ICANS), B cell aplasia, hemophagocytic lymphohistiocytosis (HLH), cytopenia, graft-versus-host disease (GvHD), hypertension, renal insufficiency, or a combination thereof.

8. The method of claim 7, wherein step (iii) is performed for at least 28 days after administration of the population of genetically engineered primary T cells.

9. The method of claim 1, wherein the B cell malignancy is non-Hodgkin lymphoma.

10. The method of claim 9, wherein the B cell malignancy is diffuse large B cell lymphoma (DLBCL), high grade B cell lymphoma with MYC and BCL2 and/or BCL6 rearrangement, transformed follicular lymphoma (FL), or grade 3b FL.

11. The method of claim 1, wherein the B cell malignancy is refractory and/or relapsed.

12. The method of claim 1, wherein the human patient has undergone one or more lines of prior anti-cancer therapies.

13. The method of claim 12, wherein the prior anti-cancer therapies comprise an anti-CD20 antibody, an anthracycline-containing regimen, or a combination thereof.

14. The method of claim 12,
wherein the human patient has refractory or relapsed transformed FL and has undergone at least one line of chemotherapy for disease after transformation to DLBCL;
wherein the B cell malignancy is refractory, and the human patient has progressive disease on last therapy, or has stable disease following at least two cycles of therapy with duration of stable disease of up to 6 months; or
wherein the human patient has failed prior autologous hematopoietic stem cell transplantation (HSCT) or ineligible for prior autologous HSCT.

15. The method of claim 1, wherein the anti-CD19 scFv comprises the amino acid sequence of SEQ ID NO: 47; or wherein the CAR that binds CD19 comprises the amino acid sequence of SEQ ID NO: 40.

16. The method of claim 1, wherein the nucleic acid encoding the anti-CD19 CAR is inserted at the site of deletion in the disrupted TRAC gene.

17. The method of claim 1, wherein the disrupted TRAC gene comprises the nucleotide sequence of SEQ ID NO: 54.

18. The method of claim 1, wherein the disrupted β2M gene in the population of genetically engineered primary T cells comprises at least one of the nucleotide sequences set forth in SEQ ID NOs: 9-14.

19. The method of claim 1, wherein at least 70% of the T cells in the population of genetically engineered primary T cells do not express a detectable level of TCR surface protein, wherein at least 50% of the T cells in the population of genetically engineered primary T cells do not express a detectable level of B2M surface protein; and/or wherein at least 30% of the T cells in the population of genetically engineered primary T cells express a detectable level of the CAR.

20. The method of claim 1, wherein the population of genetically engineered primary T cells are administered to the human patient via intravenous infusion.

* * * * *

SEQUENCE LISTING

<160> NUMBER OF SEQ ID NOS: 56

<210> SEQ ID NO 1
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 1
aagagcaaca aatctgact                                                    19

<210> SEQ ID NO 2
<211> LENGTH: 58
<212> TYPE: DNA
<213> ORGANISM: Artificial Sequence
<220> FEATURE:
<223> OTHER INFORMATION: Synthetic Polynucleotide

<400> SEQUENCE: 2
aagagcaaca gtgctgtgcc tggagcaaca aatctgacta agagcaacaa atctgact        58

<210> SEQ ID NO 3
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 3
aagagcaaca gtgctggagc aacaaatctg actaagagca acaaatctga ct              52

<210> SEQ ID NO 4
<211> LENGTH: 53
<212> TYPE: DNA
<213> ORGANISM: Artificial Sequence
<220> FEATURE:
<223> OTHER INFORMATION: Synthetic Polynucleotide

<400> SEQUENCE: 4
aagagcaaca gtgcctggag caacaaatct gactaagagc aacaaatctg act             53

<210> SEQ ID NO 5
<211> LENGTH: 38
<212> TYPE: DNA
<213> ORGANISM: Artificial Sequence
<220> FEATURE:
<223> OTHER INFORMATION: Synthetic Polynucleotide

<400> SEQUENCE: 5
aagagcaaca gtgctgacta agagcaacaa atctgact                    38

<210> SEQ ID NO 6
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 6
aagagcaaca gtgctgtggg cctggagcaa caaatctgac taagagcaac aaatctgact    60

<210> SEQ ID NO 7
<211> LENGTH: 57
<212> TYPE: DNA
<213> ORGANISM: Artificial Sequence
<220> FEATURE:
<223> OTHER INFORMATION: Synthetic Polynucleotide

<400> SEQUENCE: 7
aagagcaaca gtgctggcct ggagcaacaa atctgactaa gagcaacaaa tctgact       57

<210> SEQ ID NO 8
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 8
aagagcaaca gtgctgtgtg cctggagcaa caaatctgac taagagcaac aaatctgact    60

<210> SEQ ID NO 9
<211> LENGTH: 79
<212> TYPE: DNA
<213> ORGANISM: Artificial Sequence
<220> FEATURE:
<223> OTHER INFORMATION: Synthetic Polynucleotide

<400> SEQUENCE: 9
cgtggcctta gctgtgctcg cgctactctc tctttctgcc tggaggctat ccagcgtgag    60
tctctcctac cctcccgct                                                 79

<210> SEQ ID NO 10
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 10
cgtggcctta gctgtgctcg cgctactctc tctttcgcct ggaggctatc cagcgtgagt    60
ctctcctacc ctcccgct                                                  78

```
<210> SEQ ID NO 11
<211> LENGTH: 75
<212> TYPE: DNA
<213> ORGANISM: Artificial Sequence
<220> FEATURE:
<223> OTHER INFORMATION: Synthetic Polynucleotide

<400> SEQUENCE: 11
cgtggcctta gctgtgctcg cgctactctc tctttctgga ggctatccag cgtgagtctc    60
tcctaccctc ccgct                                                     75

<210> SEQ ID NO 12
<211> LENGTH: 84
<212> TYPE: DNA
<213> ORGANISM: Artificial Sequence
<220> FEATURE:
<223> OTHER INFORMATION: Synthetic Polynucleotide

<400> SEQUENCE: 12
cgtggcctta gctgtgctcg cgctactctc tctttctgga tagcctggag gctatccagc    60
gtgagtctct cctaccctcc cgct                                           84

<210> SEQ ID NO 13
<211> LENGTH: 55
<212> TYPE: DNA
<213> ORGANISM: Artificial Sequence
<220> FEATURE:
<223> OTHER INFORMATION: Synthetic Polynucleotide

<400> SEQUENCE: 13
cgtggcctta gctgtgctcg cgctatccag cgtgagtctc tcctaccctc ccgct         55

<210> SEQ ID NO 14
<211> LENGTH: 82
<212> TYPE: DNA
<213> ORGANISM: Artificial Sequence
<220> FEATURE:
<223> OTHER INFORMATION: Synthetic Polynucleotide

<400> SEQUENCE: 14
cgtggcctta gctgtgctcg cgctactctc tctttctgtg gcctggaggc tatccagcgt    60
gagtctctcc taccctcccg ct                                             82

<210> SEQ ID NO 15
<211> LENGTH: 100
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(20)
<223> OTHER INFORMATION: n is a, c, g, or u

<400> SEQUENCE: 15
nnnnnnnnnn nnnnnnnnnn guuuuagagc uagaaauagc aaguuaaaau aaggcuaguc    60
cguuaucaac uugaaaaagu ggcaccgagu cggugcuuuu                         100

<210> SEQ ID NO 16
<211> LENGTH: 96
<212> TYPE: RNA
<213> ORGANISM: Artificial Sequence
<220> FEATURE:
<223> OTHER INFORMATION: Synthetic Polynucleotide
```

```
<220> FEATURE:
<221> NAME/KEY: misc_feature
<222> LOCATION: (1)..(20)
<223> OTHER INFORMATION: n is a, c, g, or u

<400> SEQUENCE: 16
nnnnnnnnnn nnnnnnnnnn guuuuagagc uagaaauagc aaguuaaaau aaggcuaguc    60
cguuaucaac uugaaaaagu ggcaccgagu cggugc                              96

<210> SEQ ID NO 17
<211> LENGTH: 114
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(30)
<223> OTHER INFORMATION: n is a, c, g, or u
<220> FEATURE:
<221> NAME/KEY: misc_feature
<222> LOCATION: (18)..(30)
<223> OTHER INFORMATION: n at positions 18 to 30 is optional
<220> FEATURE:
<221> NAME/KEY: misc_feature
<222> LOCATION: (107)..(114)
<223> OTHER INFORMATION: u at positions 2 to 8 is optional

<400> SEQUENCE: 17
nnnnnnnnnn nnnnnnnnnn nnnnnnnnnn guuuuagagc uagaaauagc aaguuaaaau    60
aaggcuaguc cguuaucaac uugaaaaagu ggcaccgagu cggugcuuuu uuuu         114

<210> SEQ ID NO 18
<211> LENGTH: 100
<212> TYPE: RNA
<213> ORGANISM: Artificial Sequence
<220> FEATURE:
<223> OTHER INFORMATION: Synthetic Polynucleotide

<400> SEQUENCE: 18
agagcaacag ugcuguggcc guuuuagagc uagaaauagc aaguuaaaau aaggcuaguc    60
cguuaucaac uugaaaaagu ggcaccgagu cggugcuuuu                         100

<210> SEQ ID NO 19
<211> LENGTH: 20
<212> TYPE: RNA
<213> ORGANISM: Artificial Sequence
<220> FEATURE:
<223> OTHER INFORMATION: Synthetic Polynucleotide

<400> SEQUENCE: 19
agagcaacag ugcuguggcc                                                20

<210> SEQ ID NO 20
<211> LENGTH: 100
<212> TYPE: RNA
<213> ORGANISM: Artificial Sequence
<220> FEATURE:
<223> OTHER INFORMATION: Synthetic Polynucleotide

<400> SEQUENCE: 20
gcuacucucu cuuucuggcc guuuuagagc uagaaauagc aaguuaaaau aaggcuaguc    60
cguuaucaac uugaaaaagu ggcaccgagu cggugcuuuu                         100
```

```
<210> SEQ ID NO 21
<211> LENGTH: 20
<212> TYPE: RNA
<213> ORGANISM: Artificial Sequence
<220> FEATURE:
<223> OTHER INFORMATION: Synthetic Polynucleotide

<400> SEQUENCE: 21
gcuacucucu cuuucuggcc                                              20

<210> SEQ ID NO 22
<211> LENGTH: 100
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(3)
<223> OTHER INFORMATION: nucleotide with a 2'-O-methyl phosphorothioate
      modification
<220> FEATURE:
<221> NAME/KEY: misc_feature
<222> LOCATION: (97)..(99)
<223> OTHER INFORMATION: nucleotide with a 2'-O-methyl phosphorothioate
      modification

<400> SEQUENCE: 22
agagcaacag ugcuguggcc guuuuagagc uagaaauagc aaguuaaaau aaggcuaguc     60
cguuaucaac uugaaaaagu ggcaccgagu cggugcuuuu                         100

<210> SEQ ID NO 23
<211> LENGTH: 20
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(3)
<223> OTHER INFORMATION: nucleotide with a 2'-O-methyl phosphorothioate
      modification

<400> SEQUENCE: 23
agagcaacag ugcuguggcc                                              20

<210> SEQ ID NO 24
<211> LENGTH: 100
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(3)
<223> OTHER INFORMATION: nucleotide with a 2'-O-methyl phosphorothioate
      modification
<220> FEATURE:
<221> NAME/KEY: misc_feature
<222> LOCATION: (97)..(99)
<223> OTHER INFORMATION: nucleotide with a 2'-O-methyl phosphorothioate
      modification

<400> SEQUENCE: 24
gcuacucucu cuuucuggcc guuuuagagc uagaaauagc aaguuaaaau aaggcuaguc     60
cguuaucaac uugaaaaagu ggcaccgagu cggugcuuuu                         100
```

-continued

```
<210> SEQ ID NO 25
<211> LENGTH: 20
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(3)
<223> OTHER INFORMATION: nucleotide with a 2'-O-methyl phosphorothioate
      modification

<400> SEQUENCE: 25
gcuacucucu cuuucuggcc                                             20

<210> SEQ ID NO 26
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 26
agagcaacag tgctgtggcc                                             20

<210> SEQ ID NO 27
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 27
gctactctct ctttctggcc                                             20

<210> SEQ ID NO 28
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 28
agagcaacag tgctgtggcc tgg                                         23

<210> SEQ ID NO 29
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 29
gctactctct ctttctggcc tgg                                         23

<210> SEQ ID NO 30
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 30

Met Leu Leu Leu Val Thr Ser Leu Leu Leu Cys Glu Leu Pro His Pro
1               5                   10                  15

Ala Phe Leu Leu Ile Pro
            20
```

```
<210> SEQ ID NO 31
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 31

Met Ala Leu Pro Val Thr Ala Leu Leu Leu Pro Leu Ala Leu Leu Leu
1               5                   10                  15

His Ala Ala Arg Pro
            20

<210> SEQ ID NO 32
<211> LENGTH: 23
<212> TYPE: PRT
<213> ORGANISM: Artificial Sequence
<220> FEATURE:
<223> OTHER INFORMATION: Synthetic Polypeptide

<400> SEQUENCE: 32

Ile Tyr Ile Trp Ala Pro Leu Ala Gly Thr Cys Gly Val Leu Leu Leu
1               5                   10                  15

Ser Leu Val Ile Thr Leu Tyr
            20

<210> SEQ ID NO 33
<211> LENGTH: 126
<212> TYPE: DNA
<213> ORGANISM: Artificial Sequence
<220> FEATURE:
<223> OTHER INFORMATION: Synthetic Polynucleotide

<400> SEQUENCE: 33
aaacggggca gaaagaaact cctgtatata ttcaaacaac catttatgag accagtacaa      60
actactcaag aggaagatgg ctgtagctgc cgatttccag aagaagaaga aggaggatgt     120
gaactg                                                                126

<210> SEQ ID NO 34
<211> LENGTH: 42
<212> TYPE: PRT
<213> ORGANISM: Artificial Sequence
<220> FEATURE:
<223> OTHER INFORMATION: Synthetic Polypeptide

<400> SEQUENCE: 34

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 35
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 35
tcaaagcgga gtaggttgtt gcattccgat tacatgaata tgactcctcg ccggcctggg      60
ccgacaagaa aacattacca accctatgcc ccccacgag acttcgctgc gtacaggtcc      120
```

<210> SEQ ID NO 36
<211> LENGTH: 40
<212> TYPE: PRT
<213> ORGANISM: Artificial Sequence
<220> FEATURE:
<223> OTHER INFORMATION: Synthetic Polypeptide

<400> SEQUENCE: 36

```
Ser Lys Arg Ser Arg Leu Leu His Ser Asp Tyr Met Asn Met Thr Pro
1               5                   10                  15

Arg Arg Pro Gly Pro Thr Arg Lys His Tyr Gln Pro Tyr Ala Pro Pro
            20                  25                  30

Arg Asp Phe Ala Ala Tyr Arg Ser
        35                  40
```

<210> SEQ ID NO 37
<211> LENGTH: 336
<212> TYPE: DNA
<213> ORGANISM: Artificial Sequence
<220> FEATURE:
<223> OTHER INFORMATION: Synthetic Polynucleotide

<400> SEQUENCE: 37

```
cgagtgaagt tttcccgaag cgcagacgct ccggcatatc agcaaggaca gaatcagctg      60
tataacgaac tgaatttggg acgccgcgag gagtatgacg tgcttgataa acgccggggg     120
agagacccgg aaatggggg  taaacccga  agaaagaatc cccaagaagg actctacaat    180
gaactccaga aggataagat ggcggaggcc tactcagaaa taggtatgaa gggcgaacga     240
cgacggggaa aagtcacga  tggcctctac caagggttga gtacggcaac caaagatacg    300
tacgatgcac tgcatatgca ggccctgcct cccaga                              336
```

<210> SEQ ID NO 38
<211> LENGTH: 112
<212> TYPE: PRT
<213> ORGANISM: Artificial Sequence
<220> FEATURE:
<223> OTHER INFORMATION: Synthetic Polypeptide

<400> SEQUENCE: 38

```
Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110
```

<210> SEQ ID NO 39
<211> LENGTH: 1518
<212> TYPE: DNA
<213> ORGANISM: Artificial Sequence
<220> FEATURE:
<223> OTHER INFORMATION: Synthetic Polynucleotide

<400> SEQUENCE: 39

```
atgcttcttt tggttacgtc tctgttgctt tgcgaacttc ctcatccagc gttcttgctg      60
atccccgata ttcagatgac tcagaccacc agtagcttgt ctgcctcact gggagaccga     120
gtaacaatct cctgcaggc aagtcaagac attagcaaat acctcaattg gtaccagcag     180
aagcccgacg gaacggtaaa actcctcatc tatcatacgt caaggttgca ttccggagta     240
ccgtcacgat tttcaggttc tgggagcgga actgactatt ccttgactat ttcaaacctc     300
gagcaggagg acattgcgac atattttgt caacaaggta ataccctccc ttacactttc     360
ggaggaggaa ccaaactcga aattaccggg tccaccagtg gctctgggaa gcctggcagt     420
ggagaaggtt ccactaaagg cgaggtgaag ctccaggaga gcggcccgg tctcgttgcc     480
cccagtcaaa gcctctctgt aacgtgcaca gtgagtggtg tatcattgcc tgattatggc     540
gtctcctgga taaggcagcc cccgcgaaag ggtcttgaat ggcttggggt aatatggggc     600
tcagagacaa cgtattataa ctccgctctc aaaagtcgct tgacgataat aaaagataac     660
tccaagagtc aagttttcct aaaatgaac agtttgcaga ctgacgatac cgctatatat     720
tattgtgcta acattatta ctacggcggt agttacgcga tggattattg ggggcagggg     780
acttctgtca cagtcagtag tgctgctgcc tttgtcccgg tatttctccc agccaaaccg     840
accacgactc ccgccccgcg ccctccgaca cccgctccca ccatcgcctc tcaacctctt     900
agtcttcgcc ccgaggcatg ccgacccgcc gccggggtg ctgttcatac gaggggcttg     960
gacttcgctt gtgatattta catttgggct ccgttggcgg gtacgtgcgg cgtccttttg    1020
ttgtcactcg ttattacttt gtattgtaat cacaggaatc gctcaaagcg gagtaggttg    1080
ttgcattccg attacatgaa tatgactcct cgccggcctg ggccgacaag aaaacattac    1140
caaccctatg ccccccacg agacttcgct gcgtacaggt cccgagtgaa gtttcccga    1200
agcgcagacg ctccggcata tcagcaagga cagaatcagc tgtataacga actgaatttg    1260
ggacgccgcg aggagtatga cgtgcttgat aaacgccggg ggagagaccc ggaaatgggg    1320
ggtaaacccc gaagaaagaa tccccaagaa ggactctaca atgaactcca gaggataag    1380
atggcggagg cctactcaga aataggtatg aagggcgaac gacgacgggg aaaaggtcac    1440
gatggcctct accaagggtt gagtacggca accaaagata cgtacgatgc actgcatatg    1500
caggccctgc ctcccaga                                                  1518
```

<210> SEQ ID NO 40
<211> LENGTH: 506
<212> TYPE: PRT
<213> ORGANISM: Artificial Sequence
<220> FEATURE:
<223> OTHER INFORMATION: Synthetic Polypeptide

<400> SEQUENCE: 40

```
Met Leu Leu Leu Val Thr Ser Leu Leu Cys Glu Leu Pro His Pro
1               5                  10                  15

Ala Phe Leu Leu Ile Pro Asp Ile Gln Met Thr Gln Thr Thr Ser Ser
            20                  25                  30

Leu Ser Ala Ser Leu Gly Asp Arg Val Thr Ile Ser Cys Arg Ala Ser
        35                  40                  45

Gln Asp Ile Ser Lys Tyr Leu Asn Trp Tyr Gln Gln Lys Pro Asp Gly
    50                  55                  60

Thr Val Lys Leu Leu Ile Tyr His Thr Ser Arg Leu His Ser Gly Val
65                  70                  75                  80
```

-continued

```
Pro Ser Arg Phe Ser Gly Ser Gly Ser Gly Thr Asp Tyr Ser Leu Thr
                85                  90                  95

Ile Ser Asn Leu Glu Gln Glu Asp Ile Ala Thr Tyr Phe Cys Gln Gln
            100                 105                 110

Gly Asn Thr Leu Pro Tyr Thr Phe Gly Gly Gly Thr Lys Leu Glu Ile
        115                 120                 125

Thr Gly Ser Thr Ser Gly Ser Gly Lys Pro Gly Ser Gly Glu Gly Ser
130                 135                 140

Thr Lys Gly Glu Val Lys Leu Gln Glu Ser Gly Pro Gly Leu Val Ala
145                 150                 155                 160

Pro Ser Gln Ser Leu Ser Val Thr Cys Thr Val Ser Gly Val Ser Leu
                165                 170                 175

Pro Asp Tyr Gly Val Ser Trp Ile Arg Gln Pro Pro Arg Lys Gly Leu
            180                 185                 190

Glu Trp Leu Gly Val Ile Trp Gly Ser Glu Thr Thr Tyr Tyr Asn Ser
        195                 200                 205

Ala Leu Lys Ser Arg Leu Thr Ile Ile Lys Asp Asn Ser Lys Ser Gln
210                 215                 220

Val Phe Leu Lys Met Asn Ser Leu Gln Thr Asp Asp Thr Ala Ile Tyr
225                 230                 235                 240

Tyr Cys Ala Lys His Tyr Tyr Gly Gly Ser Tyr Ala Met Asp Tyr
                245                 250                 255

Trp Gly Gln Gly Thr Ser Val Thr Val Ser Ser Ala Ala Ala Phe Val
            260                 265                 270

Pro Val Phe Leu Pro Ala Lys Pro Thr Thr Thr Pro Ala Pro Arg Pro
        275                 280                 285

Pro Thr Pro Ala Pro Thr Ile Ala Ser Gln Pro Leu Ser Leu Arg Pro
290                 295                 300

Glu Ala Cys Arg Pro Ala Ala Gly Gly Ala Val His Thr Arg Gly Leu
305                 310                 315                 320

Asp Phe Ala Cys Asp Ile Tyr Ile Trp Ala Pro Leu Ala Gly Thr Cys
                325                 330                 335

Gly Val Leu Leu Leu Ser Leu Val Ile Thr Leu Tyr Cys Asn His Arg
            340                 345                 350

Asn Arg Ser Lys Arg Ser Arg Leu Leu His Ser Asp Tyr Met Asn Met
        355                 360                 365

Thr Pro Arg Arg Pro Gly Pro Thr Arg Lys His Tyr Gln Pro Tyr Ala
370                 375                 380

Pro Pro Arg Asp Phe Ala Ala Tyr Arg Ser Arg Val Lys Phe Ser Arg
385                 390                 395                 400

Ser Ala Asp Ala Pro Ala Tyr Gln Gln Gly Gln Asn Gln Leu Tyr Asn
                405                 410                 415

Glu Leu Asn Leu Gly Arg Arg Glu Glu Tyr Asp Val Leu Asp Lys Arg
            420                 425                 430

Arg Gly Arg Asp Pro Glu Met Gly Gly Lys Pro Arg Arg Lys Asn Pro
        435                 440                 445

Gln Glu Gly Leu Tyr Asn Glu Leu Gln Lys Asp Lys Met Ala Glu Ala
450                 455                 460

Tyr Ser Glu Ile Gly Met Lys Gly Glu Arg Arg Arg Gly Lys Gly His
465                 470                 475                 480
```

Asp Gly Leu Tyr Gln Gly Leu Ser Thr Ala Thr Lys Asp Thr Tyr Asp
            485                 490                 495

Ala Leu His Met Gln Ala Leu Pro Pro Arg
            500                 505

<210> SEQ ID NO 41
<211> LENGTH: 800
<212> TYPE: DNA
<213> ORGANISM: Artificial Sequence
<220> FEATURE:
<223> OTHER INFORMATION: Synthetic Polynucleotide

<400> SEQUENCE: 41

| | |
|---|---|
| gagatgtaag gagctgctgt gacttgctca aggccttata tcgagtaaac ggtagtgctg | 60 |
| gggcttagac gcaggtgttc tgatttatag ttcaaaacct ctatcaatga gagagcaatc | 120 |
| tcctggtaat gtgatagatt tcccaactta atgccaacat accataaacc tcccattctg | 180 |
| ctaatgccca gcctaagttg gggagaccac tccagattcc aagatgtaca gtttgctttg | 240 |
| ctgggccttt ttcccatgcc tgcctttact ctgccagagt tatattgctg gggttttgaa | 300 |
| gaagatccta ttaaataaaa gaataagcag tattattaag tagccctgca tttcaggttt | 360 |
| ccttgagtgg caggccaggc ctggccgtga acgttcactg aaatcatggc ctcttggcca | 420 |
| agattgatag cttgtgcctg tccctgagtc ccagtccatc acgagcagct ggtttctaag | 480 |
| atgctatttc ccgtataaag catgagaccg tgacttgcca gccccacaga gccccgccct | 540 |
| tgtccatcac tggcatctgg actccagcct gggttggggc aaagagggaa atgagatcat | 600 |
| gtcctaaccc tgatcctctt gtcccacaga tatccagaac cctgaccctg ccgtgtacca | 660 |
| gctgagagac tctaaatcca gtgacaagtc tgtctgccta ttcaccgatt ttgattctca | 720 |
| aacaaatgtg tcacaaagta aggattctga tgtgtatatc acagacaaaa ctgtgctaga | 780 |
| catgaggtct atggacttca | 800 |

<210> SEQ ID NO 42
<211> LENGTH: 804
<212> TYPE: DNA
<213> ORGANISM: Artificial Sequence
<220> FEATURE:
<223> OTHER INFORMATION: Synthetic Polynucleotide

<400> SEQUENCE: 42

| | |
|---|---|
| tggagcaaca aatctgactt tgcatgtgca acgccttca acaacagcat tattccagaa | 60 |
| gacaccttct tcccccagccc aggtaagggc agctttggtg ccttcgcagg ctgtttcctt | 120 |
| gcttcaggaa tggccaggtt ctgcccagag ctctggtcaa tgatgtctaa aactcctctg | 180 |
| attggtggtc tcggccttat ccattgccac caaaaccctc tttttactaa gaaacagtga | 240 |
| gccttgttct ggcagtccag agaatgcacg gggaaaaaag cagatgaaga aaggtggca | 300 |
| ggagagggca cgtggcccag cctcagtctc tccaactgag ttcctgcctg cctgcctttg | 360 |
| ctcagactgt ttgcccctta ctgctcttct aggcctcatt ctaagcccct tctccaagtt | 420 |
| gcctctcctt atttctccct gtctgccaaa aaatctttcc cagctcacta agtcagtctc | 480 |
| acgcagtcac tcattaaccc accaatcact gattgtgccg gcacatgaat gcaccaggtg | 540 |
| ttgaagtgga ggaattaaaa agtcagatga ggggtgtgcc cagaggaagc accattctag | 600 |
| ttgggggagc ccatctgtca gctgggaaaa gtccaaataa cttcagattg gaatgtgttt | 660 |
| taactcaggg ttgagaaaac agctaccttc aggacaaaag tcagggaagg gctctctgaa | 720 |

```
gaaatgctac ttgaagatac cagccctacc aagggcaggg agaggaccct atagaggcct    780
gggacaggag ctcaatgaga aagg                                           804
```

<210> SEQ ID NO 43
<211> LENGTH: 1178
<212> TYPE: DNA
<213> ORGANISM: Artificial Sequence
<220> FEATURE:
<223> OTHER INFORMATION: Synthetic Polynucleotide

<400> SEQUENCE: 43

```
ggctccggtg cccgtcagtg gcagagcgc acatcgccca cagtcccga gaagttgggg      60 ggaggggtcg gcaattgaac cggtgcctag agaaggtggc gcggggtaaa ctgggaaagt   120
gatgtcgtgt actggctccg cctttttccc gagggtgggg gagaaccgta tataagtgca   180
gtagtcgccg tgaacgttct ttttcgcaac gggtttgccg ccagaacaca ggtaagtgcc   240
gtgtgtggtt cccgcgggcc tggcctcttt acgggttatg cccttgcgt gccttgaatt    300 acttccactg gctgcagtac gtgattcttg atcccgagct tcgggttgga agtgggtggg   360
agagttcgag gccttgcgct taaggagccc cttcgcctcg tgcttgagtt gaggcctggc   420
ctgggcgctg gggccgccgc gtgcgaatct ggtggcacct tcgcgcctgt ctcgctgctt   480
tcgataagtc tctagccatt taaaattttt gatgacctgc tgcgacgctt ttttctggc    540 aagatagtct tgtaaatgcg ggccaagatc tgcacactgg tatttcggtt tttggggccg   600
cgggcggcga cggggcccgt gcgtcccagc gcacatgttc ggcgaggcgg ggcctgcgag   660
cgcggccacc gagaatcgga cgggggtagt ctcaagctgg ccggcctgct ctggtgcctg   720
gcctcgcgcc gccgtgtatc gccccgccct gggcggcaag gctggcccgg tcggcaccag   780
ttgcgtgagc ggaaagatgg ccgcttcccg gccctgctgc agggagctca aaatggagga   840
cgcggcgctc gggagagcgg gcgggtgagt cacccacaca aaggaaaagg gcctttccgt   900
cctcagccgt cgcttcatgt gactccacgg agtaccgggc gccgtccagg cacctcgatt   960
agttctcgag cttttggagt acgtcgtctt taggttgggg ggaggggttt tatgcgatgg  1020
agtttcccca cactgagtgg gtggagactg aagttaggcc agcttggcac ttgatgtaat  1080
tctccttgga atttgccctt tttgagtttg gatcttggtt cattctcaag cctcagacag  1140
tggttcaaag ttttttctt ccatttcagg tgtcgtga                            1178
```

<210> SEQ ID NO 44
<211> LENGTH: 66
<212> TYPE: DNA
<213> ORGANISM: Artificial Sequence
<220> FEATURE:
<223> OTHER INFORMATION: Synthetic Polynucleotide

<400> SEQUENCE: 44

```
atgcttcttt tggttacgtc tctgttgctt tgcgaacttc ctcatccagc gttcttgctg    60
atcccc                                                               66
```

<210> SEQ ID NO 45
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 45

Met Leu Leu Leu Val Thr Ser Leu Leu Cys Glu Leu Pro His Pro
1               5                   10                  15

Ala Phe Leu Leu Ile Pro
            20

<210> SEQ ID NO 46
<211> LENGTH: 735
<212> TYPE: DNA
<213> ORGANISM: Artificial Sequence
<220> FEATURE:
<223> OTHER INFORMATION: Synthetic Polynucleotide

<400> SEQUENCE: 46

| gatattcaga tgactcagac caccagtagc ttgtctgcct cactgggaga ccgagtaaca | 60 |
| atctcctgca gggcaagtca agacattagc aaatacctca attggtacca gcagaagccc | 120 |
| gacggaacgg taaaactcct catctatcat acgtcaaggt tgcattccgg agtaccgtca | 180 |
| cgattttcag gttctgggag cggaactgac tattccttga ctatttcaaa cctcgagcag | 240 |
| gaggacattg cgacatattt ttgtcaacaa ggtaataccc tcccttacac tttcggagga | 300 |
| ggaaccaaac tcgaaattac cgggtccacc agtggctctg gaagcctggc agtggagaa | 360 |
| ggttccacta aggcgaggt gaagctccag gagagcggcc ccggtctcgt tgcccccagt | 420 |
| caaagcctct ctgtaacgtg cacagtgagt ggtgtatcat tgcctgatta tggcgtctcc | 480 |
| tggataaggc agcccccgcg aaagggtctt gaatggcttg gggtaatatg gggctcagag | 540 |
| acaacgtatt ataactccgc tctcaaaagt cgcttgacga taataaaaga taactccaag | 600 |
| agtcaagttt tccttaaaat gaacagtttg cagactgacg ataccgctat atattattgt | 660 |
| gctaaacatt attactacgg cggtagttac gcgatggatt attgggggca ggggacttct | 720 |
| gtcacagtca gtagt | 735 |

<210> SEQ ID NO 47
<211> LENGTH: 245
<212> TYPE: PRT
<213> ORGANISM: Artificial Sequence
<220> FEATURE:
<223> OTHER INFORMATION: Synthetic Polypeptide

<400> SEQUENCE: 47

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr Gly Ser Thr Ser Gly
            100                 105                 110

Ser Gly Lys Pro Gly Ser Gly Glu Gly Ser Thr Lys Gly Glu Val Lys
        115                 120                 125

| | | | | | | | | | | | | |
|---|---|---|---|---|---|---|---|---|---|---|---|---|
|Leu|Gln|Glu|Ser|Gly|Pro|Gly|Leu|Val|Ala|Pro|Ser|Gln|Ser|Leu|Ser|
| |130| | | | |135| | | | |140| | | | |

Val Thr Cys Thr Val Ser Gly Val Ser Leu Pro Asp Tyr Gly Val Ser
145                 150                 155                 160

Trp Ile Arg Gln Pro Pro Arg Lys Gly Leu Glu Trp Leu Gly Val Ile
                165                 170                 175

Trp Gly Ser Glu Thr Thr Tyr Tyr Asn Ser Ala Leu Lys Ser Arg Leu
            180                 185                 190

Thr Ile Ile Lys Asp Asn Ser Lys Ser Gln Val Phe Leu Lys Met Asn
        195                 200                 205

Ser Leu Gln Thr Asp Asp Thr Ala Ile Tyr Tyr Cys Ala Lys His Tyr
    210                 215                 220

Tyr Tyr Gly Gly Ser Tyr Ala Met Asp Tyr Trp Gly Gln Gly Thr Ser
225                 230                 235                 240

Val Thr Val Ser Ser
            245

<210> SEQ ID NO 48
<211> LENGTH: 261
<212> TYPE: DNA
<213> ORGANISM: Artificial Sequence
<220> FEATURE:
<223> OTHER INFORMATION: Synthetic Polynucleotide

<400> SEQUENCE: 48
gctgctgcct ttgtcccggt atttctccca gccaaaccga ccacgactcc cgccccgcgc      60
cctccgacac ccgctcccac catcgcctct caacctctta gtcttcgccc cgaggcatgc     120
cgacccgccg ccgggggtgc tgttcatacg aggggcttgg acttcgcttg tgatatttac     180
atttgggctc cgttggcggg tacgtgcggc gtccttttgt tgtcactcgt tattactttg     240
tattgtaatc acaggaatcg c                                               261

<210> SEQ ID NO 49
<211> LENGTH: 252
<212> TYPE: DNA
<213> ORGANISM: Artificial Sequence
<220> FEATURE:
<223> OTHER INFORMATION: Synthetic Polynucleotide

<400> SEQUENCE: 49
tttgtcccgg tatttctccc agccaaaccg accacgactc cgccccgcg ccctccgaca       60 cccgctccca ccatcgcctc tcaacctctt agtcttcgcc cgaggcatg ccgacccgcc      120 gccgggggtg ctgttcatac gaggggcttg gacttcgctt gtgatattta catttgggct     180
ccgttggcgg gtacgtgcgg cgtccttttg ttgtcactcg ttattacttt gtattgtaat     240
cacaggaatc gc                                                         252

<210> SEQ ID NO 50
<211> LENGTH: 84
<212> TYPE: PRT
<213> ORGANISM: Artificial Sequence
<220> FEATURE:
<223> OTHER INFORMATION: Synthetic Polypeptide

<400> SEQUENCE: 50

Phe Val Pro Val Phe Leu Pro Ala Lys Pro Thr Thr Thr Pro Ala Pro
1               5                   10                  15

Arg Pro Pro Thr Pro Ala Pro Thr Ile Ala Ser Gln Pro Leu Ser Leu
            20                  25                  30

```
Arg Pro Glu Ala Cys Arg Pro Ala Ala Gly Gly Ala Val His Thr Arg
            35                  40                  45

Gly Leu Asp Phe Ala Cys Asp Ile Tyr Ile Trp Ala Pro Leu Ala Gly
    50                  55                  60

Thr Cys Gly Val Leu Leu Leu Ser Leu Val Ile Thr Leu Tyr Cys Asn
65                  70                  75                  80

His Arg Asn Arg

<210> SEQ ID NO 51
<211> LENGTH: 120
<212> TYPE: PRT
<213> ORGANISM: Artificial Sequence
<220> FEATURE:
<223> OTHER INFORMATION: Synthetic Polypeptide

<400> SEQUENCE: 51

Glu Val Lys Leu Gln Glu Ser Gly Pro Gly Leu Val Ala Pro Ser Gln
1               5                   10                  15

Ser Leu Ser Val Thr Cys Thr Val Ser Gly Val Ser Leu Pro Asp Tyr
            20                  25                  30

Gly Val Ser Trp Ile Arg Gln Pro Pro Arg Lys Gly Leu Glu Trp Leu
        35                  40                  45

Gly Val Ile Trp Gly Ser Glu Thr Thr Tyr Tyr Asn Ser Ala Leu Lys
    50                  55                  60

Ser Arg Leu Thr Ile Ile Lys Asp Asn Ser Lys Ser Gln Val Phe Leu
65                  70                  75                  80

Lys Met Asn Ser Leu Gln Thr Asp Asp Thr Ala Ile Tyr Tyr Cys Ala
                85                  90                  95

Lys His Tyr Tyr Tyr Gly Gly Ser Tyr Ala Met Asp Tyr Trp Gly Gln
            100                 105                 110

Gly Thr Ser Val Thr Val Ser Ser
        115                 120

<210> SEQ ID NO 52
<211> LENGTH: 107
<212> TYPE: PRT
<213> ORGANISM: Artificial Sequence
<220> FEATURE:
<223> OTHER INFORMATION: Synthetic Polypeptide

<400> SEQUENCE: 52

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr
            100                 105
```

```
<210> SEQ ID NO 53
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 53

Gly Ser Thr Ser Gly Ser Gly Lys Pro Gly Ser Gly Glu Gly Ser Thr
1               5                   10                  15

Lys Gly

<210> SEQ ID NO 54
<211> LENGTH: 4358
<212> TYPE: DNA
<213> ORGANISM: Artificial Sequence
<220> FEATURE:
<223> OTHER INFORMATION: Synthetic Polynucleotide

<400> SEQUENCE: 54
gagatgtaag gagctgctgt gacttgctca aggccttata tcgagtaaac ggtagtgctg      60
gggcttagac gcaggtgttc tgatttatag ttcaaaacct ctatcaatga gagagcaatc     120
tcctggtaat gtgatagatt tcccaactta atgccaacat accataaacc tcccattctg     180
ctaatgccca gcctaagttg gggagaccac tccagattcc aagatgtaca gtttgctttg     240
ctgggccttt ttcccatgcc tgcctttact ctgccagagt tatattgctg ggttttgaa      300 gaagatccta ttaaataaaa gaataagcag tattattaag tagccctgca tttcaggttt     360
ccttgagtgg caggccaggc ctggccgtga acgttcactg aaatcatggc ctcttggcca     420
agattgatag cttgtgcctg tccctgagtc ccagtccatc acgagcagct ggtttctaag     480
atgctatttc ccgtataaag catgagaccg tgacttgcca gccccacaga gccccgccct     540
tgtccatcac tggcatctgg actccagcct gggttggggc aaagagggaa atgagatcat     600
gtcctaaccc tgatcctctt gtcccacaga tatccagaac cctgaccctg ccgtgtacca     660
gctgagagac tctaaatcca gtgacaagtc tgtctgccta ttcaccgatt tgattctca     720 aacaaatgtg tcacaaagta aggattctga tgtgtatatc acagacaaaa ctgtgctaga     780
catgaggtct atggacttca ggctccggtg cccgtcagtg ggcagagcgc acatcgccca     840
cagtccccga gaagttgggg gaggggtcg gcaattgaac cggtgcctag agaaggtggc     900
gcggggtaaa ctgggaaagt gatgtcgtgt actggctccg ccttttttccc gagggtgggg     960 gagaaccgta taagtgcaga gtagtcgccg tgaacgttct ttttcgcaac gggtttgccg    1020
ccagaacaca ggtaagtgcc gtgtgtggtt cccgcgggcc tggcctcttt acgggttatg    1080
gcccttgcgt gccttgaatt acttccactg gctgcagtac gtgattcttg atcccgagct    1140
tcgggttgga agtgggtggg agagttcgag gccttgcgct taaggagccc cttcgcctcg    1200
tgcttgagtt gaggcctggc ctgggcgctg gggccgccgc gtgcgaatct ggtggcacct    1260
tcgcgcctgt ctcgctgctt tcgataagtc tctagccatt taaaattttt gatgacctgc    1320
tgcgacgctt tttttctggc aagatagtct tgtaaatgcg gccaagatc tgcacactgg    1380 tatttcggtt tttggggccg cggcggcga cggggcccgt gcgtcccagc gcacatgttc    1440
ggcgaggcgg ggcctgcgag cgcggccacc gagaatcgga cggggtagt ctcaagctgg    1500 ccggcctgct ctggtgcctg gcctcgcgcc gccgtgtatc gccccgccct gggcggcaag    1560
gctggcccgg tcggcaccag ttgcgtgagc ggaaagatgg ccgcttccg gccctgctgc    1620 agggagctca aaatggagga cgcggcgctc gggagagcgg gcgggtgagt cacccacaca    1680
```

```
aaggaaaagg gcctttccgt cctcagccgt cgcttcatgt gactccacgg agtaccgggc    1740
gccgtccagg cacctcgatt agttctcgag cttttggagt acgtcgtctt taggttgggg    1800
ggagggtttt tatgcgatgg agtttcccca cactgagtgg gtggagactg aagttaggcc    1860
agcttggcac ttgatgtaat tctccttgga atttgcccct tttgagtttg gatcttggtt    1920
cattctcaag cctcagacag tggttcaaag tttttttctt ccatttcagg tgtcgtgacc    1980
accatgcttc ttttggttac gtctctgttg ctttgcgaac ttcctcatcc agcgttcttg    2040
ctgatccccg atattcagat gactcagacc accagtagct tgtctgcctc actgggagac    2100
cgagtaacaa tctcctgcag ggcaagtcaa gacattagca aatacctcaa ttggtaccag    2160
cagaagcccg acggaacggt aaaactcctc atctatcata cgtcaaggtt gcattccgga    2220
gtaccgtcac gattttcagg ttctgggagc ggaactgact attccttgac tatttcaaac    2280
ctcgagcagg aggacattgc gacatatttt tgtcaacaag gtaatacccT cccttacact    2340
ttcggaggag gaaccaaact cgaaattacc gggtccacca gtggctctgg gaagcctggc    2400
agtggagaag gttccactaa aggcgaggtg aagctccagg agagcggccc cggtctcgtt    2460
gcccccagtc aaagcctctc tgtaacgtgc acagtgagtg gtgtatcatt gcctgattat    2520
ggcgtctcct ggataaggca gccccgcgca aagggtcttg aatggcttgg ggtaatatgg    2580
ggctcagaga caacgtatta taactccgct ctcaaaagtc gcttgacgat aataaaagat    2640
aactccaaga gtcaagtttt ccttaaaatg aacagtttgc agactgacga taccgctata    2700
tattattgtg ctaaacatta ttactacggc ggtagttacg cgatggatta ttgggggcag    2760
gggacttctg tcacagtcag tagtgctgct gcctttgtcc cggtatttct cccagccaaa    2820
ccgaccacga ctcccgcccc cgcgcctccg acacccgctc ccaccatcgc ctctcaacct    2880
cttagtcttc gccccgaggc atgccgaccc gccgccgggg tgctgttcac acgaggggc    2940 ttggacttcg cttgtgatat ttacatttgg gctccgttgg cgggtacgtg cggcgtcctt    3000
ttgttgtcac tcgttattac tttgtattgt aatcacagga atcgctcaaa gcggagtagg    3060
ttgttgcatt ccgattacat gaatatgact cctcgccggc ctgggccgac aagaaaacat    3120
taccaaccct atgcccccc acgagacttc gctgcgtaca ggtcccgagt gaagttttcc    3180
cgaagcgcag acgctccggc atatcagcaa ggacagaatc agctgtataa cgaactgaat    3240
ttgggacgcc gcgaggagta tgacgtgctt gataaacgcc gggggagaga cccggaaatg    3300
gggggtaaac cccgaagaaa gaatccccaa gaaggactct acaatgaact ccagaaggat    3360
aagatggcgg aggcctactc agaaataggt atgaagggcg aacgacgacg gggaaaaggt    3420
cacgatggcc tctaccaagg gttgagtacg gcaaccaaag atacgtacga tgcactgcat    3480
atgcaggccc tgcctcccag ataataataa aatcgctatc catcgaagat ggatgtgtgt    3540 tggtttttg tgtgtggagc aacaaatctg actttgcatg tgcaaacgcc ttcaacaaca    3600
gcattattcc agaagacacc ttcttcccca gcccaggtaa gggcagcttt ggtgccttcg    3660
caggctgttt ccttgcttca ggaatggcca ggttctgccc agagctctgg tcaatgatgt    3720
ctaaaactcc tctgattggt ggtctcggcc ttatccattg ccaccaaaac cctctttta    3780 ctaagaaaca gtgagcctcg ttctggcagt ccagagaatg acacgggaaa aaagcagatg    3840
aagagaaggt ggcaggagag ggcacgtggc ccagcctcag tctctccaac tgagttcctg    3900
cctgcctgcc tttgctcaga ctgtttgccc cttactgctc ttctaggcct cattctaagc    3960
cccttctcca agttgcctct ccttatttct ccctgtctgc caaaaatct ttcccagctc    4020 actaagtcag tctcacgcag tcactcatta acccaccaat cactgattgt gccggcacat    4080
```

```
gaatgcacca ggtgttgaag tggaggaatt aaaaagtcag atgagggtg tgcccagagg    4140 aagcaccatt ctagttgggg gagcccatct gtcagctggg aaaagtccaa ataacttcag    4200
attggaatgt gttttaactc agggttgaga aaacagctac cttcaggaca aaagtcaggg    4260
aagggctctc tgaagaaatg ctacttgaag ataccagccc taccaagggc agggagagga    4320
ccctatagag gcctgggaca ggagctcaat gagaaagg                             4358
```

<210> SEQ ID NO 55
<211> LENGTH: 1368
<212> TYPE: PRT
<213> ORGANISM: Artificial Sequence
<220> FEATURE:
<223> OTHER INFORMATION: Synthetic Polypeptide

<400> SEQUENCE: 55

```
Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320
```

```
Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
        515                 520                 525

Tyr Val Thr Glu Gly Met Arg Lys Pro Ala Phe Leu Ser Gly Glu Gln
    530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
        595                 600                 605

Asn Glu Glu Asn Glu Asp Ile Leu Glu Asp Ile Val Leu Thr Leu Thr
    610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
        675                 680                 685

Ala Asn Arg Asn Phe Met Gln Leu Ile His Asp Ser Leu Thr Phe
            690                 695                 700                 Phe

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735
```

```
Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
            755                 760             765

Thr Thr Gln Lys Gly Gln Lys Asn Ser Arg Glu Arg Met Lys Arg Ile
    770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                  815

Gln Asn Gly Arg Asp Met Tyr Val Asp Gln Glu Leu Asp Ile Asn Arg
            820                 825                 830

Leu Ser Asp Tyr Asp Val Asp His Ile Val Pro Gln Ser Phe Leu Lys
            835                 840                 845

Asp Asp Ser Ile Asp Asn Lys Val Leu Thr Arg Ser Asp Lys Asn Arg
            850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
            915                 920                 925

Lys His Val Ala Gln Ile Leu Asp Ser Arg Met Asn Thr Lys Tyr Asp
    930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
            980                 985                 990

Val Gly Thr Ala Leu Ile Lys Lys Tyr Pro Lys Leu Glu Ser Glu Phe
            995                1000                1005

Val Tyr Gly Asp Tyr Lys Val Tyr Asp Val Arg Lys Met Ile Ala
1010                1015                1020

Lys Ser Glu Gln Glu Ile Gly Lys Ala Thr Ala Lys Tyr Phe Phe
1025                1030                1035

Tyr Ser Asn Ile Met Asn Phe Phe Lys Thr Glu Ile Thr Leu Ala
1040                1045                1050

Asn Gly Glu Ile Arg Lys Arg Pro Leu Ile Glu Thr Asn Gly Glu
1055                1060                1065

Thr Gly Glu Ile Val Trp Asp Lys Gly Arg Asp Phe Ala Thr Val
1070                1075                1080

Arg Lys Val Leu Ser Met Pro Gln Val Asn Ile Val Lys Lys Thr
1085                1090                1095

Glu Val Gln Thr Gly Gly Phe Ser Lys Glu Ser Ile Leu Pro Lys
1100                1105                1110

Arg Asn Ser Asp Lys Leu Ile Ala Arg Lys Lys Asp Trp Asp Pro
1115                1120                1125

Lys Lys Tyr Gly Gly Phe Asp Ser Pro Thr Val Ala Tyr Ser Val
1130                1135                1140
```

Leu Val Val Ala Lys Val Glu Lys Gly Lys Ser Lys Lys Leu Lys
    1145                1150                1155

Ser Val Lys Glu Leu Leu Gly Ile Thr Ile Met Glu Arg Ser Ser
    1160                1165                1170

Phe Glu Lys Asn Pro Ile Asp Phe Leu Glu Ala Lys Gly Tyr Lys
    1175                1180                1185

Glu Val Lys Lys Asp Leu Ile Ile Lys Leu Pro Lys Tyr Ser Leu
    1190                1195                1200

Phe Glu Leu Glu Asn Gly Arg Lys Arg Met Leu Ala Ser Ala Gly
    1205                1210                1215

Glu Leu Gln Lys Gly Asn Glu Leu Ala Leu Pro Ser Lys Tyr Val
    1220                1225                1230

Asn Phe Leu Tyr Leu Ala Ser His Tyr Glu Lys Leu Lys Gly Ser
    1235                1240                1245

Pro Glu Asp Asn Glu Gln Lys Gln Leu Phe Val Glu Gln His Lys
    1250                1255                1260

His Tyr Leu Asp Glu Ile Ile Glu Gln Ile Ser Glu Phe Ser Lys
    1265                1270                1275

Arg Val Ile Leu Ala Asp Ala Asn Leu Asp Lys Val Leu Ser Ala
    1280                1285                1290

Tyr Asn Lys His Arg Asp Lys Pro Ile Arg Glu Gln Ala Glu Asn
    1295                1300                1305

Ile Ile His Leu Phe Thr Leu Thr Asn Leu Gly Ala Pro Ala Ala
    1310                1315                1320

Phe Lys Tyr Phe Asp Thr Thr Ile Asp Arg Lys Arg Tyr Thr Ser
    1325                1330                1335

Thr Lys Glu Val Leu Asp Ala Thr Leu Ile His Gln Ser Ile Thr
    1340                1345                1350

Gly Leu Tyr Glu Thr Arg Ile Asp Leu Ser Gln Leu Gly Gly Asp
    1355                1360                1365

<210> SEQ ID NO 56
<211> LENGTH: 4682
<212> TYPE: DNA
<213> ORGANISM: Artificial Sequence
<220> FEATURE:
<223> OTHER INFORMATION: Synthetic Polynucleotide

<400> SEQUENCE: 56
cctgcaggca gctgcgcgct cgctcgctca ctgaggccgc ccgggcgtcg ggcgaccttt      60
ggtcgcccgg cctcagtgag cgagcgagcg cgcagagagg gagtggccaa ctccatcact     120 agggggttcct gcgccgcac gcgtgagatg taaggagctg ctgtgacttg ctcaaggcct     180
tatatcgagt aaacggtagt gctggggctt agacgcaggt gttctgattt atagttcaaa     240
acctctatca atgagagagc aatctcctgg taatgtgata gatttcccaa cttaatgcca     300
acataccata aacctcccat tctgctaatg cccagcctaa gttggggaga ccactccaga     360
ttccaagatg tacagtttgc tttgctgggc ctttttccca tgcctgcctt tactctgcca     420
gagttatatt gctggggttt tgaagaagat cctattaaat aaaagaataa gcagtattat     480
taagtagccc tgcatttcag gtttccttga gtggcaggcc aggcctggcc gtgaacgttc     540
actgaaatca tggcctcttg gccaagattg atagcttgtg cctgtccctg agtcccagtc     600
catcacgagc agctggtttc taagatgcta tttcccgtat aaagcatgag accgtgactt     660
gccagcccca cagagccccg cccttgtcca tcactggcat ctggactcca gcctgggttg     720

```
gggcaaagag ggaaatgaga tcatgtccta accctgatcc tcttgtccca cagatatcca   780
gaaccctgac cctgccgtgt accagctgag agactctaaa tccagtgaca agtctgtctg   840
cctattcacc gattttgatt ctcaaacaaa tgtgtcacaa agtaaggatt ctgatgtgta   900
tatcacagac aaaactgtgc tagacatgag gtctatggac ttcaggctcc ggtgcccgtc   960
agtgggcaga gcgcacatcg cccacagtcc ccgagaagtt ggggggaggg gtcggcaatt  1020
gaaccggtgc ctagagaagg tggcgcgggg taaactggga aagtgatgtc gtgtactggc  1080
tccgcctttt tcccgagggt ggggagaac cgtatataag tgcagtagtc gccgtgaacg  1140
ttcttttttcg caacgggttt gccgccagaa cacaggtaag tgccgtgtgt ggttcccgcg  1200
ggcctggcct ctttacgggt tatggccctt gcgtgccttg aattacttcc actggctgca  1260
gtacgtgatt cttgatcccg agcttcgggt tggaagtggg tgggagagtt cgaggccttg  1320
cgcttaagga gccccttcgc ctcgtgcttg agttgaggcc tggcctgggc gctggggccg  1380
ccgcgtgcga atctggtggc accttcgcgc ctgtctcgct gctttcgata agtctctagc  1440
catttaaaat ttttgatgac ctgctgcgac gcttttttttc tggcaagata gtcttgtaaa  1500
tgcgggccaa gatctgcaca ctggtatttc ggttttttggg gccgcgggcg gcgacggggc  1560
ccgtgcgtcc cagcgcacat gttcggcgag gcggggcctg cgagcgcggc caccgagaat  1620
cggacggggg tagtctcaag ctggccggcc tgctctggtg cctggcctcg cgccgccgtg  1680
tatcgccccg ccctgggcgg caaggctggc ccggtcggca ccagttgcgt gagcggaaag  1740
atggccgctt cccggccctg ctgcaggagc tcaaaatgg aggacgcggc gctcgggaga  1800
gcgggcgggt gagtcaccca cacaaaggaa aagggccttt ccgtcctcag ccgtcgcttc  1860
atgtgactcc acggagtacc gggcgccgtc caggcacctc gattagttct cgagcttttg  1920
gagtacgtcg tctttaggtt gggggagggg gttttatgcg atggagtttc cccacactga  1980
gtgggtggag actgaagtta ggccagcttg gcacttgatg taattctcct tggaatttgc  2040
cctttttgag tttggatctt ggttcattct caagcctcag acagtggttc aaagtttttt  2100
tcttccattt caggtgtcgt gaccaccatg cttctttttgg ttacgtctct gttgctttgc  2160
gaacttcctc atccagcgtt cttgctgatc cccgatattc agatgactca gaccaccagt  2220
agcttgtctg cctcactggg agaccgagta acaatctcct gcagggcaag tcaagacatt  2280
agcaaatacc tcaattggta ccagcagaag cccgacggaa cggtaaaact cctcatctat  2340
catacgtcaa ggttgcattc cggagtaccg tcacgatttt caggttctgg gagcggaact  2400
gactattcct tgactatttc aaacctcgag caggaggaca ttgcgacata ttttttgtcaa  2460
caaggtaata ccctccctta cactttcgga ggaggaacca aactcgaaat taccgggtcc  2520
accagtggct ctgggaagcc tggcagtgga aaggttcca ctaaaggcga ggtgaagctc  2580
caggagagcg gccccggtct cgttgccccc agtcaaagcc tctctgtaac gtgcacagtg  2640
agtggtgtat cattgcctga ttatggcgtc tcctggataa ggcagcccc gcgaaagggt  2700
cttgaatggc ttgggtaat atgggctca gagacaacgt attataactc cgctctcaaa  2760
agtcgcttga cgataataaa agataactcc aagagtcaag ttttccttaa aatgaacagt  2820
ttgcagactg acgataccgc tatatattat tgtgctaaac attattacta cggcggtagt  2880
tacgcgatgg attattgggg gcaggggact tctgtcacag tcagtagtgc tgctgccttt  2940
gtcccggtat ttctcccagc caaaccgacc acgactcccg ccccgcgccc tccgacaccc  3000
gctcccacca tcgcctctca acctcttagt cttgccccg aggcatgccg acccgccgcc  3060
gggggtgctg ttcatacgag gggcttggac ttcgcttgtg atatttacat ttgggctccg  3120
```

```
ttggcgggta cgtgcggcgt cctttgttg tcactcgtta ttactttgta ttgtaatcac    3180
aggaatcgct caaagcggag taggttgttg cattccgatt acatgaatat gactcctcgc   3240
cggcctgggc cgacaagaaa acattaccaa ccctatgccc cccacgaga cttcgctgcg    3300 tacaggtccc gagtgaagtt ttcccgaagc gcagacgctc cggcatatca gcaaggacag   3360
aatcagctgt ataacgaact gaatttggga cgccgcgagg agtatgacgt gcttgataaa   3420
cgccggggga gagacccgga aatgggggt aaacccgaa gaaagaatcc caagaagga     3480 ctctacaatg aactccagaa ggataagatg gcggaggcct actcagaaat aggtatgaag   3540
ggcgaacgac gacggggaaa aggtcacgat ggcctctacc aagggttgag tacggcaacc   3600
aaagatacgt acgatgcact gcatatgcag gccctgcctc ccagataata ataaaatcgc   3660
tatccatcga agatggatgt gtgttggttt tttgtgtgtg gagcaacaaa tctgactttg   3720
catgtgcaaa cgccttcaac aacagcatta ttccagaaga caccttcttc cccagcccag   3780
gtaagggcag ctttggtgcc ttcgcaggct gtttccttgc ttcaggaatg gccaggttct   3840
gcccagagct ctggtcaatg atgtctaaaa ctcctctgat tggtggtctc ggccttatcc   3900
attgccacca aaaccctctt tttactaaga aacagtgagc cttgttctgg cagtccagag   3960
aatgacacgg gaaaaagca gatgaagaga aggtggcagg agagggcacg tggcccagcc   4020
tcagtctctc caactgagtt cctgcctgcc tgcctttgct cagactgttt gccccttact   4080
gctcttctag gcctcattct aagcccttc tccaagttgc ctctccttat ttctccctgt    4140
ctgccaaaaa atctttccca gctcactaag tcagtctcac gcagtcactc attaacccac   4200
caatcactga ttgtgccggc acatgaatgc accaggtgtt gaagtggagg aattaaaaag   4260
tcagatgagg ggtgtgccca gaggaagcac cattctagtt gggggagccc atctgtcagc   4320
tgggaaaagt ccaaataact tcagattgga atgtgtttta actcagggtt gagaaaacag   4380
ctaccttcag gacaaaagtc agggaagggc tctctgaaga aatgctactt gaagatacca   4440
gccctaccaa gggcagggag aggaccctat agaggcctgg gacaggagct caatgagaaa   4500
ggtaaccacg tgcggaccga ggctgcagcg tcgtcctccc taggaacccc tagtgatgga   4560
gttggccact ccctctctgc gcgctcgctc gctcactgag gccgggcgac caaaggtcgc   4620
ccgacgcccg ggctttgccc gggcggcctc agtgagcgag cgagcgcgca gctgcctgca   4680
gg                                                                  4682
```